United States Patent
Lee et al.

(10) Patent No.: US 11,041,842 B2
(45) Date of Patent: Jun. 22, 2021

(54) CULTURING PATCH, CULTURING METHOD, CULTURE TEST METHOD, CULTURE TEST DEVICE, DRUG TEST METHOD, AND DRUG TEST DEVICE

(71) Applicant: NOUL CO., LTD., Gyeonggi-do (KR)

(72) Inventors: Dong Young Lee, Gyeonggi-do (KR); Chan Yang Lim, Gyeonggi-do (KR); Kyung Hwan Kim, Gyeonggi-do (KR)

(73) Assignee: NOUL CO., LTD.

( * ) Notice: Subject to any disclaimer, the term of this patent is extended or adjusted under 35 U.S.C. 154(b) by 0 days.

(21) Appl. No.: 16/079,299

(22) PCT Filed: Feb. 23, 2017

(86) PCT No.: PCT/KR2017/002031
§ 371 (c)(1),
(2) Date: Aug. 23, 2018

(87) PCT Pub. No.: WO2017/146507
PCT Pub. Date: Aug. 31, 2017

(65) Prior Publication Data
US 2019/0049426 A1 Feb. 14, 2019

Related U.S. Application Data

(60) Provisional application No. 62/298,959, filed on Feb. 23, 2016.

(30) Foreign Application Priority Data

Jun. 4, 2016 (KR) .................. 10-2016-0069936
Jun. 4, 2016 (KR) .................. 10-2016-0069937
Jun. 4, 2016 (KR) .................. 10-2016-0069938
Jul. 27, 2016 (KR) .................. 10-2016-0095739
Sep. 13, 2016 (KR) .................. 10-2016-0118462
Nov. 1, 2016 (KR) .................. 10-2016-0144551
Feb. 23, 2017 (KR) .................. 10-2017-0024392

(51) Int. Cl.
| | |
|---|---|
| *G01N 33/49* | (2006.01) |
| *G01N 33/483* | (2006.01) |
| *G01N 1/30* | (2006.01) |
| *C12Q 1/6844* | (2018.01) |
| *C12Q 1/6848* | (2018.01) |
| *G01N 33/50* | (2006.01) |
| *G01N 21/77* | (2006.01) |
| *G01N 33/558* | (2006.01) |
| *B01L 3/00* | (2006.01) |
| *G01N 15/06* | (2006.01) |
| *G01N 33/52* | (2006.01) |
| *G01N 33/574* | (2006.01) |

(Continued)

(52) U.S. Cl.
CPC ............ *G01N 33/4833* (2013.01); *B01L 3/00* (2013.01); *C07K 16/3061* (2013.01); *C12Q 1/686* (2013.01); *C12Q 1/6844* (2013.01); *C12Q 1/6848* (2013.01); *C12Q 1/701* (2013.01); *G01N 1/30* (2013.01); *G01N 1/31* (2013.01); *G01N 1/312* (2013.01); *G01N 15/06* (2013.01); *G01N 15/14* (2013.01); *G01N 21/77* (2013.01); *G01N 33/49* (2013.01); *G01N 33/5082* (2013.01); *G01N 33/52* (2013.01); *G01N 33/533* (2013.01); *G01N 33/5304* (2013.01); *G01N 33/558* (2013.01); *G01N 33/574* (2013.01); *G01N 33/60* (2013.01); *G06T 7/0012* (2013.01); *G06T 7/0014* (2013.01); *B01L 3/505* (2013.01); *B01L 7/52* (2013.01); *G01N 2001/302* (2013.01); *G01N 2015/0065* (2013.01); *G01N 2015/0693* (2013.01); *G01N 2021/7723* (2013.01); *G01N 2021/7786* (2013.01)

(58) Field of Classification Search
None
See application file for complete search history.

(56) References Cited

U.S. PATENT DOCUMENTS 555,270 A 2/1896 Taylor
3,870,146 A 3/1975 Greenfield et al.
(Continued)

FOREIGN PATENT DOCUMENTS

CN 1034617 A 8/1989
CN 1207171 A 2/1999
(Continued)

OTHER PUBLICATIONS

Zhu et al., 2015, "Microbiology Experiment and Learning Guide—Experiment 6 In Vitro Antibacterial Test of Drug," Fourth Force Medical University Press, pp. 24-26 (in Chinese with English translation), 11 pages.
Becton, Dickinson and Company, 2013, "BD™ EMB Agar (Eosin Methylene Blue Agar), Modified Intended Use," retreived from the internet: URL: https://legacy.bd.com/RESOURCE.ASPX?IDX=8973 [retreived on Apr. 2, 2020] (3 pages).
(Continued)

*Primary Examiner* — Heidi Reese
(74) *Attorney, Agent, or Firm* — Jones Day

(57) ABSTRACT

The present disclosure relates to a culturing patch, culturing method, culture test method, culture test device, drug test method, and drug test device, and the culturing patch according to an aspect of the present disclosure includes component required for growth of an object to be cultured, and a mesh structural body provided in a mesh structure forming micro-cavities in which the component required for growth are contained that is configured to come into contact with a reaction region in which the object to be cultured is placed and provide some of the contained component required for growth to the reaction region.

21 Claims, 59 Drawing Sheets

(51) Int. Cl.
- *G01N 15/14* (2006.01)
- *G01N 33/60* (2006.01)
- *C12Q 1/686* (2018.01)
- *C07K 16/30* (2006.01)
- *G01N 1/31* (2006.01)
- *C12Q 1/70* (2006.01)
- *G06T 7/00* (2017.01)
- *G01N 33/53* (2006.01)
- *G01N 33/533* (2006.01)
- *B01L 7/00* (2006.01)
- *G01N 15/00* (2006.01)

(56) References Cited

U.S. PATENT DOCUMENTS

| | | |
|---|---|---|
| 4,250,257 A | 2/1981 | Lee et al. |
| 4,839,297 A | 6/1989 | Freitag et al. |
| 4,938,593 A | 7/1990 | Morris et al. |
| 5,143,714 A | 9/1992 | Cosgrove et al. |
| 5,552,270 A | 9/1996 | Khrapko et al. |
| 5,552,279 A | 9/1996 | Weisburg et al. |
| 5,776,684 A | 7/1998 | Chirikjian et al. |
| 5,779,982 A | 7/1998 | Aota et al. |
| 5,928,879 A | 7/1999 | Dumler et al. |
| 6,063,029 A | 5/2000 | Saita et al. |
| 6,174,683 B1 | 1/2001 | Hahn et al. |
| 7,261,800 B1 | 8/2007 | Nakazato |
| 7,767,414 B1 | 8/2010 | Smith et al. |
| 8,293,487 B1 | 10/2012 | Zhang |
| 8,305,579 B2 | 11/2012 | Treynor et al. |
| 8,409,849 B2 | 4/2013 | Yamasaki |
| 8,628,787 B2 * | 1/2014 | Soldani ............... A61L 31/046 424/400 |
| 8,809,027 B1 | 8/2014 | Lynch et al. |
| 8,936,912 B2 | 1/2015 | Mitra et al. |
| 10,234,447 B2 | 3/2019 | Manaresi et al. |
| 10,254,286 B2 | 4/2019 | Pirie-Shepherd et al. |
| 10,345,204 B2 | 7/2019 | Lee et al. |
| 10,371,610 B2 | 8/2019 | Lee et al. |
| 2002/0055126 A1 | 5/2002 | Schaffler et al. |
| 2003/0083294 A1 | 5/2003 | Sullenger et al. |
| 2003/0124619 A1 | 7/2003 | Weigl et al. |
| 2003/0211507 A1 | 11/2003 | Hatch et al. |
| 2004/0038306 A1 | 2/2004 | Agnew et al. |
| 2004/0126826 A1 | 7/2004 | Yusuf et al. |
| 2004/0175710 A1 | 9/2004 | Haushalter |
| 2005/0139511 A1 | 6/2005 | Burns et al. |
| 2005/0175987 A1 | 8/2005 | Jansen et al. |
| 2005/0175997 A1 | 8/2005 | Ono et al. |
| 2005/0202567 A1 | 9/2005 | Zanzucchi et al. |
| 2005/0244976 A1 | 11/2005 | Gee et al. |
| 2006/0088847 A1 | 4/2006 | Gu et al. |
| 2006/0111331 A1 | 5/2006 | Eishingdrelo et al. |
| 2006/0115905 A1 | 6/2006 | Hatch et al. |
| 2006/0121474 A1 | 6/2006 | Kim et al. |
| 2006/0172278 A1 | 8/2006 | Bonner et al. |
| 2007/0117177 A1 | 5/2007 | Luo et al. |
| 2007/0128073 A1 | 6/2007 | Tappen |
| 2007/0224701 A1 | 9/2007 | Rosenstein |
| 2008/0090267 A1 | 4/2008 | Komatsu et al. |
| 2008/0138842 A1 | 6/2008 | Boehringer et al. |
| 2008/0182287 A1 | 7/2008 | Smith et al. |
| 2009/0098165 A1 | 4/2009 | Arulanandam et al. |
| 2009/0220968 A1 | 9/2009 | Issadore et al. |
| 2010/0047790 A1 | 2/2010 | Southern et al. |
| 2010/0168390 A1 | 7/2010 | Brix et al. |
| 2011/0041978 A1 | 2/2011 | Wallace et al. |
| 2011/0070606 A1 | 3/2011 | Winkelman et al. |
| 2011/0257666 A1 | 10/2011 | Ladet et al. |
| 2012/0040397 A1 | 2/2012 | Luo et al. |
| 2012/0064041 A1 | 3/2012 | Alexanian |
| 2012/0171290 A1 | 7/2012 | Coursaget et al. |
| 2013/0213811 A1 | 8/2013 | Kennedy et al. |
| 2013/0288273 A1 | 10/2013 | Takagi et al. |
| 2013/0296761 A1 | 11/2013 | Goto et al. |
| 2013/0338016 A1 | 12/2013 | McDonough et al. |
| 2014/0004527 A1 | 1/2014 | Oka et al. |
| 2014/0038230 A1 | 2/2014 | Beck et al. |
| 2014/0073063 A1 | 3/2014 | Lieber et al. |
| 2014/0242607 A1 | 8/2014 | Sogabe et al. |
| 2014/0273088 A1 | 9/2014 | Winther |
| 2015/0080252 A1 | 3/2015 | Godwin et al. |
| 2015/0139511 A1 | 5/2015 | Yoon et al. |
| 2016/0265028 A1 | 9/2016 | Kim et al. |
| 2019/0025281 A1 | 1/2019 | Lee et al. |
| 2019/0048395 A1 | 2/2019 | Lee et al. |
| 2019/0049349 A1 | 2/2019 | Lee et al. |
| 2019/0056296 A1 | 2/2019 | Lee et al. |
| 2019/0056298 A1 | 2/2019 | Lee et al. |
| 2019/0064140 A1 | 2/2019 | Lee et al. |
| 2019/0316995 A1 | 10/2019 | Lee et al. |
| 2020/0011772 A1 | 1/2020 | Lee et al. |
| 2020/0240882 A1 | 7/2020 | Lee et al. |
| 2020/0249134 A1 | 8/2020 | Lee et al. |

FOREIGN PATENT DOCUMENTS

| | | |
|---|---|---|
| CN | 1363006 A | 8/2002 |
| CN | 1409110 A | 4/2003 |
| CN | 1561202 A | 1/2005 |
| CN | 1747703 A | 3/2006 |
| CN | 1971276 A | 5/2007 |
| CN | 101004377 A | 7/2007 |
| CN | 101225430 A | 7/2008 |
| CN | 101464237 A | 6/2009 |
| CN | 101598731 A | 12/2009 |
| CN | 101610847 A | 12/2009 |
| CN | 102245305 A | 11/2011 |
| CN | 102245755 A | 11/2011 |
| CN | 102272595 A | 12/2011 |
| CN | 102665917 A | 9/2012 |
| CN | 103038639 A | 4/2013 |
| CN | 103261872 A | 8/2013 |
| CN | 103328651 A | 9/2013 |
| CN | 103800040 A | 5/2014 |
| CN | 103808551 A | 5/2014 |
| CN | 104271191 A | 1/2015 |
| CN | 104349769 A | 2/2015 |
| CN | 104651473 A | 5/2015 |
| CN | 105122034 A | 12/2015 |
| CN | 105136795 A | 12/2015 |
| CN | 105259095 A | 1/2016 |
| EP | 2072993 A2 | 6/2009 |
| EP | 2072993 A3 | 6/2009 |
| EP | 2206462 A1 | 4/2010 |
| EP | 2940474 A1 | 11/2015 |
| JP | S 63-281050 A | 11/1988 |
| JP | H 08-271390 A | 10/1996 |
| JP | S 52-89375 A | 7/1997 |
| JP | 2003344394 A | 12/2003 |
| JP | 2004077387 A | 3/2004 |
| JP | 2008518662 A | 6/2008 |
| JP | 2008164520 A | 7/2008 |
| JP | 2009518651 A | 5/2009 |
| JP | 2012515931 A | 7/2012 |
| JP | 5198399 B2 | 5/2013 |
| JP | 2013515235 A | 5/2013 |
| JP | 2013515955 A | 5/2013 |
| KR | 10-0601831 B1 | 7/2006 |
| KR | 10-2006-0112258 A | 10/2006 |
| KR | 10-2011-0084636 A | 7/2011 |
| KR | 10-2011-0136782 A | 12/2011 |
| KR | 10-2013-0138153 A | 12/2013 |
| KR | 10-2014-0082757 A | 7/2014 |
| KR | 10-2014-0100580 A | 8/2014 |
| KR | 10-2014-0103350 A | 8/2014 |
| KR | 10-1453796 B1 | 10/2014 |
| KR | 10-2015-0048964 A | 5/2015 |
| KR | 10-1540845 B1 | 7/2015 |
| WO | WO 2000077293 A1 | 12/2000 |
| WO | WO 2002072081 A1 | 9/2002 |
| WO | WO 2004024955 A1 | 3/2004 |
| WO | WO 2004071469 A2 | 8/2004 |

(56) References Cited

FOREIGN PATENT DOCUMENTS

| WO | WO 2004071469 A3 | 8/2004 |
| WO | WO 2006050032 A2 | 5/2006 |
| WO | WO 2006050032 A3 | 5/2006 |
| WO | WO 2006053770 A1 | 5/2006 |
| WO | WO 2006108087 A2 | 10/2006 |
| WO | WO 2006108087 A3 | 10/2006 |
| WO | WO 2007067847 A2 | 6/2007 |
| WO | WO 2007067847 A3 | 6/2007 |
| WO | WO 2008075086 A1 | 6/2008 |
| WO | WO 2010039627 A2 | 4/2010 |
| WO | WO 2010039627 A3 | 4/2010 |
| WO | WO 2010041088 A1 | 4/2010 |
| WO | WO 2010052543 A1 | 5/2010 |
| WO | WO 2010052543 A8 | 5/2010 |
| WO | WO 2010082820 A2 | 7/2010 |
| WO | WO 2010082820 A3 | 7/2010 |
| WO | WO 2011066449 A1 | 6/2011 |
| WO | WO 2011076705 A1 | 6/2011 |
| WO | WO 2011080539 A1 | 7/2011 |
| WO | WO 2011143075 A2 | 11/2011 |
| WO | WO 2011143075 A3 | 11/2011 |
| WO | WO 2012003579 A1 | 1/2012 |
| WO | WO 2012030313 A1 | 3/2012 |
| WO | WO 2012048154 A1 | 4/2012 |
| WO | WO 2012072980 A1 | 6/2012 |
| WO | WO 2012137506 A1 | 10/2012 |
| WO | WO 2013095896 A1 | 12/2012 |
| WO | WO 2013086015 A1 | 6/2013 |
| WO | WO 2013103712 A1 | 7/2013 |
| WO | WO 2013111054 A1 | 8/2013 |
| WO | WO 2013169924 A1 | 11/2013 |
| WO | WO 2014041093 A1 | 3/2014 |
| WO | WO 2014146062 A2 | 9/2014 |
| WO | WO 2014146062 A3 | 9/2014 |
| WO | WO 2017048871 A1 | 3/2017 |

OTHER PUBLICATIONS

Cardinal Health, 2013, "Histology vol. II: Laboratory products for your Histology needs," retreived from the Internet: URL:http://www.henryschein.com/assets/medical/2883001.pdf [retreived on Apr. 2, 2020] (95 pages).

Deiss et al., 2014, "Antimicrobial susceptibility assays in paper-based portable culture devices," Lab on a Chip, 14(1):167-171.

Dictionary.com, definition of "mesh," retreived from internet: https://www.dictionary.com/browse/mesh?s=t on Feb. 3, 2020 (6 pages).

English translation of the International Search Report and Written Opinion dated Jul. 6, 2017 of PCT Application No. PCT/KR2017/002028 (published as WO 2017/146504) (9 pages).

English translation of the International Search Report and Written Opinion dated May 29, 2017 of PCT Application No. PCT/KR2017/002026 (published as WO 2017/146502) (7 pages).

English translation of the International Search Report and Written Opinion dated May 29, 2017 of PCT Application No. PCT/KR2017/002027 (published as WO 2017/146503) (8 pages).

English translation of the International Search Report and Written Opinion dated May 29, 2017 of PCT Application No. PCT/KR2017/002029 (published as WO 2017/146505) (9 pages).

English translation of the International Search Report and Written Opinion dated May 29, 2017 of PCT Application No. PCT/KR2017/002030 (published as WO 2017/146506) (9 pages).

English translation of the International Search Report and Written Opinion dated May 29, 2017 of PCT Application No. PCT/KR2017/002031 (published as WO 2017/146507) (12 pages).

English translation of the International Search Report and Written Opinion dated May 29, 2017 of PCT Application No. PCT/KR2017/002032 (published as WO 2017/146508) (11 pages).

Geckil et al., 2010, "Engineering hydrogels as extracellular matrix mimics," Nanomedicine (Lond), 5(3):469-484.

Horibata et al., 2015, "Utilization of the Soft Agar Colony Formation Assay to Identify Inhibitors of Tumorigenicity in Breast Cancer Cells," J Vis Exp., (99):e52727 (7 pages).

Hudzicki, 2009, "Kirby-Bauer Disk Diffusion Susceptibility Test Protocol," American Society for Microbiology, retreived from the internet: https://www.asm.org/getattachment/2594ce26-bd44-47f6-8287-0657aa9185ad/kirby-bauer-disk-diffusion-susceptibility-test-protocol-pdf.pdf, retreived on Jul. 23, 2019 (23 pages).

Liu et al., 2009, "Aptamer-nanoparticle strip biosensor for sensitive detection of cancer cells," Anal Chem., 81(24):10013-10018.

Massart et al., 2009, "Striatal GPR88 expression is confined to the whole projection neuron population and is regulated by dopaminergic and glutamatergic afferents," Eur J Neurosci., 30(3):397-414.

Matsuo et al., 2001, "A simple method for classification of cell death by use of thin layer collagen gel for the detection of apoptosis and/or necrosis after cancer chemotherapy," Jpn J Cancer Res., 92(7):813-819.

Notodihardjo et al., 2015, "Gelatin hydrogel impregnated with platelet-rich plasma releasate promotes angiogenesis and wound healing in murine model," J Artif Organs., 18(1):64-71.

Oss-Ronen et al., 2011, "Polymer-conjugated albumin and fibrinogen composite hydrogels as cell scaffolds designed for affinity-based drug delivery," Acta Biomater, 7(1):163-170.

Punyani et al., 2006, "Sustained release of iodine from a polymeric hydrogel device for water disinfection," Journal of Applied Polymer Science, 103(5):3334-3340.

Rand, 1996, "Crystal violet can be used to visualize DNA bands during gel electrophoresis and to improve cloning efficiency," Technical Tips Online, 1:23-24.

Romano et al., 2015, "Controlled antiseptic/eosin release from chitosan-based hydrogel modified fibrous substrates," Carbohydr Polym., 131:306-314.

Wakayama et al., 2013, "Design of a single-step immunoassay principle based on the combination of an enzyme-labeled antibody release coating and a hydrogel copolymerized with a fluorescent enzyme substrate in a microfluidic capillary device," Lab Chip, 13(22):4304-4307.

Wu et al., 2008, "Disposable reagentless electrochemical immunosensor array based on a biopolymer/sol-gel membrane for simultaneous measurement of several tumor markers," Clin Chem., 54(9):1481-1488.

Zustiak et al., 2010, "Solute diffusion and interactions in cross-linked poly(ethylene glycol) hydrogels studied by Fluorescence Correlation Spectroscopy," Soft Matter, 6(15):3609-3618.

Man et al., 2011, "Currently Used Markers for CTC Isolation—Advantages, Limitations and Impact on Cancer Prognosis," J Clinic Experiment Pathol, 1:1 (7 pages).

Beck, M., et al., "On-chip sample preparation by controlled release of antibodies for simple CD4 counting", Lab Chip, 2012, 12, 167, 7 pages.

* cited by examiner (a)　　　　　　　　(b)

(a)                      (b)

CULTURING PATCH, CULTURING METHOD, CULTURE TEST METHOD, CULTURE TEST DEVICE, DRUG TEST METHOD, AND DRUG TEST DEVICE

CROSS-REFERENCES TO RELATED APPLICATIONS

This application is a U.S. national phase application, pursuant to 35 U.S.C. § 371, of PCT/KR2017/002031, filed Feb. 23, 2017, designating the United States, which claims the benefit of U.S. Provisional Application No. 62/298,959, filed Feb. 23, 2016, and claims priority to Korean Application No. 10-2016-0069936, filed Jun. 4, 2016, to Korean Application No. 10-2016-0069937, filed Jun. 4, 2016, to Korean Application No. 10-2016-0069938, filed Jun. 4, 2016, to Korean Application No. 10-2016-0095739, filed Jul. 27, 2016, to Korean Application No. 10-2016-0118462, filed Sep. 13, 2016, to Korean Application No. 10-2016-0144551, filed Nov. 1, 2016, and to Korean Application No. 10-2017-0024392, filed Feb. 23, 2017. The entire contents of the aforementioned patent applications are incorporated herein by this reference.

TECHNICAL FIELD

The present disclosure relates to a culturing patch, culturing method, culture test method, culture test device, drug test method, and drug test device, and more particularly, to a culturing patch that contains nutrients required for culturing cells or bacteria, and a culturing method, culture test method, culture test device, drug test method, and drug test device using the culturing patch.

BACKGROUND ART

Due to a rapidly aging society and increasing need for quality of life, the diagnostics market which aims at early diagnosis and early treatment is growing every year in the world, including South Korea, and quick and easy diagnosis is becoming an important issue. In particular, forms of diagnosis are being transitioned into forms in which diagnosis can be performed without using large diagnostic equipment, such as in-vitro diagnosis (IVD) or point-of-care testing (POCT) which is immediately performed next to a patient. Blood testing, which is one specific diagnostic field for performing IVD, is one diagnostic method that accounts for a large portion in the IVD field and is widely used.

Clinical microbiology is one specific field of laboratory medicine, and is a study in which, with a bodily fluid of a patient suspected of infection with microorganisms as a sample, whether the bodily fluid is actually inflected with microorganisms is determined, and when the bodily fluid has been infected, the microorganisms are identified, and further, an antibiotic to which the identified microorganisms are sensitive is determined. In performing clinical microbial testing, in most cases, bacterial culture for proliferating and separating bacteria present in a sample is used instead of directly using a sample collected from a patient.

Bacterial culture is performed to diagnose infection by determining whether bacteria present in a clinical sample are pathogens or normal flora. Also, a sufficient amount of pure cultured bacteria derived from a single bacterium is obtained, and features of a colony, biochemical characteristics, dyeability, and serological reactions are used to identify the bacterial species and perform an antibiotic susceptibility test.

However, in conventional cell culture, bacteria are applied on a petri dish that holds plate count agar (PCA) media or agar media and then growth degrees in accordance with sizes of colonies are determined in most cases. However, such a conventional culturing technique has a problem in that it takes time from a few days to several weeks until a colony can be observed with visual inspection.

In recent years, as research and development on stem cells have been vigorously carried out, the demand on in-vitro culturing of cells has also been increased. Since the cell culture is performed in a similar fashion to the above-described bacterial culture, the cell culture has the same problem.

SUMMARY

An aspect of the present disclosure is to provide a patch capable of storing a substance.

An aspect of the present disclosure is to provide a patch capable of providing a reaction space for a substance.

An aspect of the present disclosure is to provide a patch capable of providing a substance.

An aspect of the present disclosure is to provide a patch capable of absorbing a substance.

An aspect of the present disclosure is to provide a patch capable of providing an environment.

An aspect of the present disclosure is to provide a culturing patch that contains a required nutrient component required for the growth of objects to be cultured such as microorganisms including bacteria or cells.

An aspect of the present disclosure is to provide a culturing method using a culturing patch.

An aspect of the present disclosure is to provide a culture test in which a culturing patch is used to test a degree of growth of objects to be cultured and a culture test device for performing the same.

An aspect of the present disclosure is to provide a drug test method in which a patch is used to test a degree of growth inhibition or death of objects to be cultured due to a drug and a drug test device for performing the same.

Aspects of the present disclosure are not limited to those mentioned above, and unmentioned aspects will be clearly understood by those of ordinary skill in the art to which the present disclosure pertains from the present specification and the accompanying drawings.

According to an aspect of the present disclosure, there is provided a culturing patch including component required for growth of an object to be cultured, and a mesh structural body provided in a mesh structure forming micro-cavities in which the component required for growth are contained that is configured to come into contact with a reaction region in which the object to be cultured is placed and deliver some of the contained component required for growth to the reaction region.

According to another aspect of the present disclosure, there is provided a culturing method for culturing an object to be cultured by using a patch, which includes a mesh structural body forming micro-cavities and contains a liquid substance in the micro-cavities, the culturing method including placing an object to be cultured in a reaction region; and delivering component required for growth of the object to be cultured to the reaction region by using a patch that contains the component required for growth s.

According to still another aspect of the present disclosure, there is provided a culture test method for culturing an object to be cultured and testing a degree of growth of the object to be cultured by using a patch, which includes a mesh structural body forming micro-cavities and contains a liquid substance in the micro-cavities, the culture test method including placing an object to be cultured in a reaction region, delivering component required for growth of the object to be cultured to the reaction region by using a patch that contains the component required for growth s, and acquiring an image of the object to be cultured by acquiring an image of the reaction region.

According to yet another aspect of the present disclosure, there is provided a drug patch including a drug that affects growth or activity of an object to be drug-tested, and a mesh structural body provided in a mesh structure forming micro-cavities in which the drug is contained that is configured to come into contact with a reaction region in which the object to be drug-tested is placed and deliver some of the contained drug to the reaction region.

According to yet another aspect of the present disclosure, there is provided a drug test method for testing efficacy of a drug by using a patch, which includes a mesh structural body forming micro-cavities and contains a liquid substance in the micro-cavities, the drug test method including placing a sample in a reaction region, delivering the drug to the reaction region by using a patch that contains the drug, and acquiring an image of the sample by acquiring an image of the reaction region. The drug test method may include acquiring, on the basis of the image, at least one piece of information of size information and count information of the sample, and determining, on the basis of the at least one piece of information, at least one of a degree of growth, a degree of activity, a degree of growth inhibition, and a degree of death of the sample due to the drug.

Solutions of the present disclosure are not limited to those mentioned above, and unmentioned solutions should be clearly understood by those of ordinary skill in the art to which the present disclosure pertains from the present specification and the accompanying drawings.

According to the present disclosure, containing, providing, and absorption of a substance can be easily performed.

According to the present disclosure, a reaction region for a substance can be provided or a predetermined environment can be provided to a target region.

According to the present disclosure, culturing of an object to be cultured, a culture test, and a drug test can be more conveniently performed, and a test result can be promptly obtained.

According to the present disclosure, a diagnosis result with sufficient validity can be obtained from a small degree of growth or a small degree of growth inhibition.

According to the present disclosure, providing and absorption of a substance can be properly adjusted using a patch, and an amount of a nutrient-requiring component required for diagnosis can be significantly reduced.

Advantageous effects of the present disclosure are not limited to those mentioned above, and unmentioned advantageous effects should be clearly understood by those of ordinary skill in the art to which the present disclosure pertains from the present specification and the accompanying drawings.

DETAILED DESCRIPTION

Figure 1:
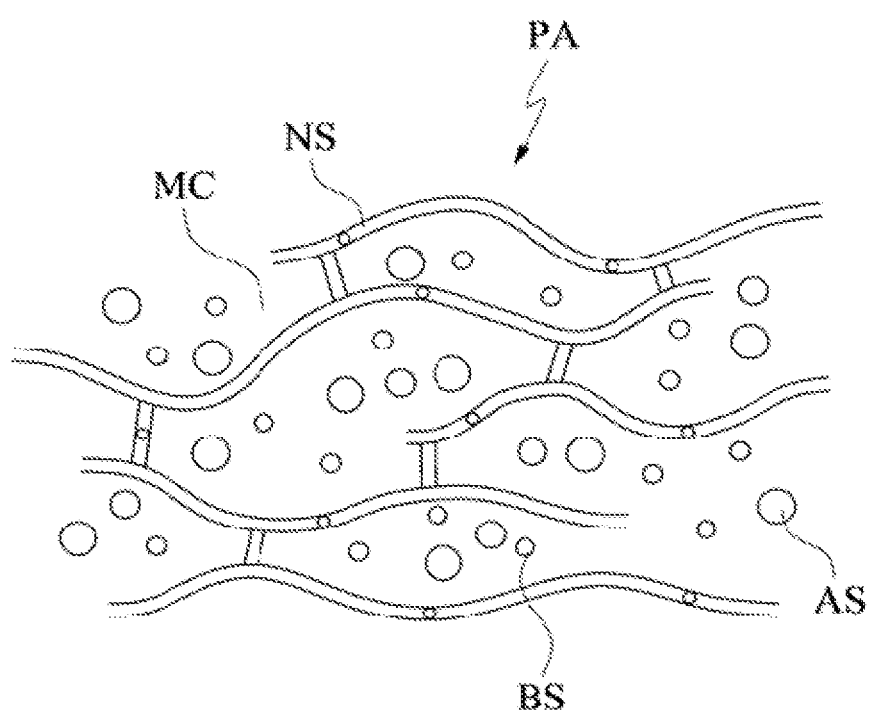
FIG. 1 illustrates an example of a patch in detail according to the present application.

Since embodiments described herein are for clearly describing the spirit of the present disclosure to those of ordinary skill in the art to which the present disclosure pertains, the present disclosure is not limited to the embodiments described herein, and the scope of the present disclosure should be construed as including revised examples or modified examples not departing from the spirit of the present disclosure.

General terms currently being used as widely as possible have been selected as terms used herein in consideration of functions in the present disclosure, but the terms may be changed according to intentions and practices of those of ordinary skill in the art to which the present disclosure pertains or the advent of new technologies, etc. However, instead, when a particular term is defined as a certain meaning and used, the meaning of the term will be separately described. Consequently, the terms used herein should be construed on the basis of substantial meanings of the terms and content throughout the present specification instead of simply on the basis of names of the terms.

The accompanying drawings herein are for easily describing the present disclosure. Since shapes illustrated in the drawings may have been exaggeratedly depicted as much as necessary to assist in understating the present disclosure, the present disclosure is not limited by the drawings.

When detailed description of a known configuration or function related to the present disclosure is deemed to obscure the gist of the present disclosure in the present specification, the detailed description related thereto will be omitted as necessary.

According to an aspect of the present disclosure, there is provided a culturing patch including component required for growth of an object to be cultured, and a mesh (net-like) structural body provided in a mesh structure forming micro-cavities in which the component required for growth are contained that is configured to come into contact with a reaction region in which the object to be cultured is placed and provide some of the contained component required for growth to the reaction region.

According to another aspect of the present disclosure, there is provided a culturing method for culturing an object to be cultured by using a patch, which includes a mesh structural body forming micro-cavities and contains a liquid substance in the micro-cavities, the culturing method including placing an object to be cultured in a reaction region; and providing component required for growth which is required for growth of the object to be cultured to the reaction region by using a patch that contains the component required for growth s.

The object to be cultured may include at least one of bacteria, parasites, cells separated from a tissue, and primary cultured cells.

According to still another aspect of the present disclosure, there is provided a culture test method for culturing an object to be cultured and testing a degree of growth of the object to be cultured by using a patch, which includes a mesh structural body forming micro-cavities and contains a liquid substance in the micro-cavities, the culture test method including placing an object to be cultured in a reaction region, providing component required for growth of the object to be cultured to the reaction region by using a patch that contains the component required for growth s, and acquiring an image of the object to be cultured by acquiring an image of the reaction region.

The culture test method may further include acquiring, on the basis of the image, at least one piece of information of size information and count information of the object to be cultured, and determining, on the basis of the at least one piece of information, a degree of growth of the object to be cultured.

The acquiring of the image may include spacing the patch apart from the reaction region, and acquiring the image of the reaction region while the patch is spaced apart therefrom.

The acquiring of the image of the reaction region while the patch is spaced apart therefrom may include irradiating light from a surface opposite a surface of a plate on which the reaction region is located, and acquiring the image of the reaction region by the light being incident on the surface of the plate on which the reaction region is located.

The acquiring of the image may include acquiring an image of the reaction region while the patch is in contact with the reaction region.

The acquiring of the image of the reaction region while the patch is in contact with the reaction region may include irradiating light from a surface of a plate on which the reaction region is located, and acquiring the image of the reaction region by the light being incident on a surface opposite the surface of the plate on which the reaction region is located.

The acquiring of the image of the object to be cultured by acquiring the image of the reaction region may be performed periodically, and the culture test method may further include determining a degree of growth of the object to be cultured by comparing a plurality of images acquired in the acquiring of the image which is periodically performed.

According to yet another aspect of the present disclosure, there is provided a drug patch including a drug that affects growth or activity of an object to be drug-tested, and a mesh structural body provided in a mesh structure forming micro-cavities in which the drug is contained that is configured to come into contact with a reaction region in which the object to be drug-tested is placed and provide some of the contained drug to the reaction region.

The drug patch may further include a component required for growth of the object to be drug-tested, and the component required for growth may be contained in the mesh structure forming the micro-cavities.

According to yet another aspect of the present disclosure, there is provided a drug test method for testing efficacy of a drug by using a patch, which includes a mesh structural body forming micro-cavities and contains a liquid substance in the micro-cavities, the drug test method including placing a sample in a reaction region, providing the drug to the reaction region by using a patch that contains the drug, and acquiring an image of the sample by acquiring an image of the reaction region. The drug test method may include acquiring, on the basis of the image, at least one information of a size information and a count information of the sample, and determining, on the basis of the at least one information, at least one of a degree of growth, a degree of activity, a degree of growth inhibition, and a degree of death of the sample due to the drug.

The acquiring of the image may include spacing the patch apart from the reaction region, and acquiring the image of the reaction region while the patch is spaced apart therefrom.

The acquiring of the image of the reaction region while the patch is spaced apart therefrom may include irradiating light from a surface opposite a surface of a plate on which the reaction region is located, and acquiring the image of the reaction region by the light being incident on the surface of the plate on which the reaction region is located.

The acquiring of the image may include acquiring an image of the reaction region while the patch is in contact with the reaction region.

The acquiring of the image of the reaction region while the patch is in contact with the reaction region may include irradiating light from a surface of a plate on which the reaction region is located, and acquiring the image of the reaction region by the light being incident on a surface opposite the surface of the plate on which the reaction region is located.

The acquiring of the image of the sample by acquiring the image of the reaction region may be performed periodically, and the drug test method may further include determining an effect of the drug comparing a plurality of images acquired in the acquiring of the image which is periodically performed.

The drug test method may further include contacting a drug sheet which holds the drug with the patch, and absorbing the drug from the drug sheet by the patch so that the drug is contained in the patch.

1. Patch 1.1 Meaning of Patch

In the present application, a patch for managing a liquid substance is disclosed.

The liquid substance may mean a substance which is in a liquid state and can flow.

The liquid substance may be a substance formed of a single component having fluidity. Alternatively, the liquid substance may be a mixture that includes a substance formed of a plurality of components.

When the liquid substance is a substance formed of a single component, the liquid substance may be a substance formed of a single chemical element or a compound including a plurality of chemical elements.

When the liquid substance is a mixture, a portion of the substance formed of a plurality of components may serve as a solvent, and the other portion may serve as a solute. That is, the mixture may be a solution.

A plurality of components constituting the mixture which forms the substance may be uniformly distributed. Alternatively, the mixture including the substance formed of a plurality of components may be a uniformly mixed mixture.

The substance formed of a plurality of components may include a solvent and a substance that is not dissolved in the solvent and is uniformly distributed.

A portion of the substance formed of a plurality of components may be non-uniformly distributed. The non-uniformly distributed substance may include non-uniformly distributed particle components in the solvent. In this case, the non-uniformly distributed particle components may be in a solid phase.

For example, a substance that may be managed using the patch may be in a state of 1) a liquid formed of a single component, 2) a solution, or 3) a colloid, or according to circumstances, may be in a state in which 4) solid particles are non-uniformly distributed within another liquid substance.

Hereinafter, the patch according to the present application will be described in more detail.

1.2 General Nature of Patch

1.2.1 Configuration

Figure 2:
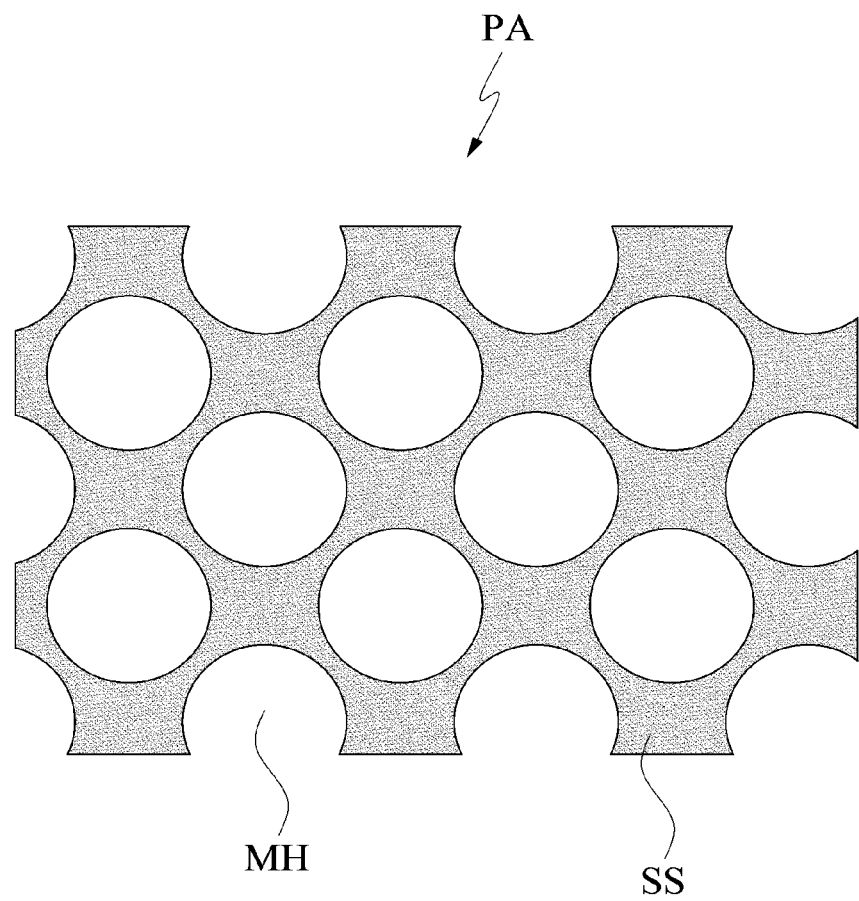
FIG. 2 illustrates an example of a patch in detail according to the present application.

FIGS. 1 and 2 are views illustrating an example of a patch according to the present application. The patch according to the present application will be described below with reference to FIGS. 1 and 2.

Referring to FIG. 1, a patch PA according to the present application may include a mesh structural body NS and a liquid substance.

As the liquid substance, a base substance BS and an additive substance AS may be taken into consideration separately.

The patch PA may be in a gel state (gel type). The patch PA may be implemented as a gel-type structural body in which colloidal molecules are bound and mesh tissues are formed.

The patch PA according to the present application is a structure for managing a liquid substance SB, and may include a three-dimensional mesh (net-like) structural body NS. The mesh structural body NS may be a continuously distributed solid structure. The mesh structural body NS may have a mesh structure in which a plurality of micro-threads are intertwined. However, the mesh structural body NS is not limited to the mesh form in which the plurality of micro-threads are intertwined, and may also be implemented in the form of an arbitrary three-dimensional matrix that is formed by connection of a plurality of micro-structures. For example, the mesh structural body NS may be a frame structural body that includes a plurality of micro-cavities. In other words, the mesh structural body NS may form a plurality of micro-cavities MC.

FIG. 2 illustrates a structure of a patch according to an embodiment of the present application. Referring to FIG. 2, the mesh structural body of the patch PA may have a sponge structure SS. The mesh structural body of the sponge structure SS may include a plurality of micro-holes MH. Hereinafter, the terms micro-holes MH and the micro-cavities MC may be used interchangeably, and unless particularly mentioned otherwise, the term micro-cavities MC is defined as encompassing the concept of the micro-holes MH.

The mesh structural body NS may have a regular or irregular pattern. Furthermore, the mesh structural body NS may include both a region having a regular pattern and a region having an irregular pattern.

A density of the mesh structural body NS may have a value within a predetermined range. Preferably, the predetermined range may be set within a limit in which the form of the liquid substance SB captured in the patch PA is maintained in a form that corresponds to the patch PA. The density may be defined as a degree to which the mesh structural body NS is dense or a mass ratio, a volume ratio, or the like that the mesh structural body NS occupies in the patch.

The patch according to the present application may manage the liquid substance SB by having a three-dimensional mesh structure.

The patch PA according to the present application may include the liquid substance SB, and the fluidity of the liquid substance SB included in the patch PA may be limited by the form of the mesh structural body NS of the patch PA.

The liquid substance SB may freely flow within the mesh structural body NS. In other words, the liquid substance SB is placed in the plurality of micro-cavities formed by the mesh structural body NS. An exchange of liquid substance SB may occur between neighboring micro-cavities. In this case, the liquid substance SB may be present in a state in which the liquid substance SB permeating into a frame structural body that forms the mesh tissues. In such a case, nano-sized pores into which the liquid substances SB may permeate may be formed in the frame structural body.

Further, whether to the liquid substance SB is filled in the frame structural body of the mesh structure may be determined depending on a molecular weight or a particle size of the liquid substance SB to be captured in the patch PA. A substance having a relatively large molecular weight may be captured in the micro-cavities, and a substance having a relatively small molecular weight may be captured by the frame structural body and filled in the micro-cavities and/or the frame structural body of the mesh structural body NS.

In the present specification, the term "capture" may be defined as a state in which the liquid substance SB is placed in the plurality of micro-cavities and/or nano-sized holes formed by the mesh structural body NS. As described above, the state in which the liquid substance SB is captured in the patch PA is defined as including a state in which the liquid substance SB may flow between the micro-cavities and/or the nano-sized holes.

As in the following, the base substance BS and the additive substance AS may be taken into consideration separately as the liquid substance SB.

The base substance BS may be a liquid substance SB having fluidity.

The additive substance AS may be a substance that is mixed with the base substance BS and has fluidity. In other words, the base substance BS may be a solvent. The additive substance AS may be a solute that is dissolved in the solvent or may be particles that are not melted in the solvent.

The base substance BS may be a substance capable of flowing inside a matrix formed by the mesh structural body NS. The base substance BS may be uniformly distributed in the mesh structural body NS or may be distributed only in a partial region of the mesh structural body NS. The base substance BS may be a liquid having a single component.

The additive substance AS may be a substance that is mixed with the base substance BS or dissolved in the base substance BS. For example, the additive substance AS may serve as a solute while the base substance BS is a solvent. The additive substance AS may be uniformly distributed in the base substance BS.

The additive substance AS may be fine particles that are not dissolved in the base substance BS. For example, the additive substance AS may include colloidal molecules and fine particles such as microorganisms.

The additive substance AS may include particles larger than the micro-cavities formed by the mesh structural body NS. When the size of the micro-cavities is smaller than the size of the particles included in the additive substance AS, fluidity of the additive substance AS may be limited.

According to an embodiment, the additive substance AS may include a component that is selectively included in the patch PA.

The additive substance AS does not necessarily refer to a substance that is lower in quantity or inferior in function in comparison to the above-described base substance BS.

Hereinafter, characteristics of the liquid substance SB captured in the patch PA may be presumed as characteristics of the patch PA. That is, the characteristics of the patch PA may depend on characteristics of a substance captured in the patch PA.

1.2.2 Characteristics

As described above, the patch PA according to the present application may include the mesh structural body NS. The patch PA may manage the liquid substance SB through the mesh structural body NS. The patch PA may allow the liquid substance SB captured in the patch PA to maintain at least some of its unique characteristics.

For example, diffusion of a substance may occur in a region of the patch PA in which the liquid substance SB is distributed, and a force such as surface tension may come into action.

The patch PA may provide a liquid environment in which diffusion of a target substance is caused due to thermal motion of a substance or a difference in density or concentration thereof. Generally, "diffusion" refers to a phenomenon in which particles that constitute a substance are spread from a side at which concentration is high to a side at which a concentration is low due to a difference in concentration. Such a diffusion phenomenon may be basically understood as a phenomenon that occurs due to motion of molecules (translational motion in a gas or liquid, vibrational motion in a solid, and the like). In the present application, in addition to referring to the phenomenon in which particles are spread from a side at which a concentration is high toward a side at which a concentration is low due to a difference in concentration or density, "diffusion" also refers to a phenomenon in which particles move due to irregular motion of molecules that occurs even when a concentration is uniform. The expression "irregular motion" may also have the same meaning as "diffusion" unless particularly mentioned otherwise. The diffused substance may be a solute that is dissolved in the liquid substance SB, and the diffused substance may be provided in a solid, liquid, or gas state.

More specifically, a non-uniformly-distributed substance in the liquid substance SB captured by the patch PA may be diffused in a space provided by the patch PA. In other words, the additive substance AS may be diffused in a space defined by the patch PA.

The non-uniformly-distributed substance or the additive substance AS in the liquid substance SB managed by the patch PA may be diffused within the micro-cavities provided by the mesh structural body NS of the patch PA. A region in which the non-uniformly-distributed substance or the additive substance AS may be diffused may be changed by the patch PA being connected or coming into contact with another substance.

Even when, after the concentration of the substance or the additive substance AS has become uniform, as a result of diffusion of the non-uniformly-distributed substance or the additive substance AS within the patch PA or within an external region connected to the patch PA, the substance or the additive substance AS may continuously move due to irregular motion of molecules inside the patch PA and/or within the external region connected to the patch PA.

The patch PA may be implemented to exhibit a hydrophilic or hydrophobic property. In other words, the mesh structural body NS of the patch PA may have a hydrophilic or hydrophobic property.

When properties of the mesh structural body NS and the liquid substance SB are similar, the mesh structural body NS may be able to manage the liquid substance SB more effectively.

The base substance BS may be a polar hydrophilic substance or a nonpolar hydrophobic substance. The additive substance AS may exhibit a hydrophilic or hydrophobic property.

The properties of the liquid substance SB may be related to the base substance BS and/or the additive substance AS. For example, when both the base substance BS and the additive substance AS are hydrophilic, the liquid substance SB may be hydrophilic, and when both the base substance BS and the additive substance AS are hydrophobic, the liquid substance SB may be hydrophobic. When polarities of the base substance BS and the additive substance AS are different, the liquid substance SB may be hydrophilic or hydrophobic.

When polarities of both the mesh structural body NS and the liquid substance SB are hydrophilic or hydrophobic, an attractive force may come into action between the mesh structural body NS and the liquid substance SB. When polarities of the mesh structural body NS and the liquid substance SB are opposite, e.g., when the polarity of the mesh structural body NS is hydrophobic and the polarity of the liquid substance SB is hydrophilic, a repulsive force may act between the mesh structural body NS and the liquid substance SB.

On the basis of the above-described properties, the patch PA may be solely used, a plurality of patches PA may be used, or the patch PA may be used with another medium to induce a desired reaction. Hereinafter, functional aspects of the patch PA will be described.

However, hereinafter, for convenience of description, the patch PA is assumed as being a gel type that may include a hydrophilic solution. In other words, unless particularly mentioned otherwise, the mesh structural body NS of the patch PA is assumed to have a hydrophilic property.

However, the scope of the present application should not be interpreted as being limited to the gel-type patch PA having a hydrophilic property. In addition to a gel-type patch PA that includes a solution exhibiting a hydrophobic property, a gel-type patch PA from which a solvent is removed and even a sol-type patch PA, as long as it is capable of implementing functions according to the present application, may belong to the scope of the present application.

2. Functions of Patch

Due to the above-described characteristics, the patch according to the present application may have some useful functions. In other words, by capturing the liquid substance SB, the patch may become involved in behavior of the liquid substance SB.

Accordingly, hereinafter, in accordance with forms of behavior of the substance with respect to the patch PA, a reservoir function in which a state of the substance is defined in a predetermined region formed by the patch PA and a channeling function in which a state of the substance is defined in a region including an external region of the patch PA will be separately described.

2.1 Reservoir 2.1.1 Meaning

As described above, the patch PA according to the present application may capture the liquid substance SB. In other words, the patch PA may perform a function as a reservoir.

The patch PA may capture the liquid substance SB in the plurality of micro-cavities formed in the mesh structural body NS using the mesh structural body NS. The liquid substance SB may occupy at least a portion of the fine micro-cavities formed by the three-dimensional mesh structural body NS of the patch PA or be penetrated in the nano-sized pores formed in the mesh structural body NS.

The liquid substance SB placed in the patch PA does not lose properties of a liquid even when the liquid substance SB is distributed in the plurality of micro-cavities. That is, the liquid substance SB has fluidity even in the patch PA, and diffusion of a substance may occur in the liquid substance SB distributed in the patch PA, and an appropriate solute may be dissolved in the substance.

The reservoir function of the patch PA will be described below in more detail.

2.1.2 Containing

In the present application, the patch PA may capture a target substance due to the above-described characteristics.

The patch PA may have resistance to a change in an external environment within a predetermined range. In this way, the patch PA may maintain a state in which the substance is captured therein. The liquid substance SB, which is a target to be captured, may occupy the three-dimensional mesh structural body NS.

Hereinafter, for convenience, the above-described function of the patch PA will be referred to as "containing."

However, "the patch PA containing the liquid substance" is defined to encompass a case in which the liquid substance is contained in a space formed by the mesh structure and/or a case in which the liquid substance is contained in the frame structural body constituting the mesh structural body NS.

The patch PA may contain the liquid substance SB. For example, the patch PA may contain the liquid substance SB, due to an attractive force that acts between the mesh structural body NS of the patch PA and the liquid substance SB. The liquid substance SB may be bound to the mesh structural body NS with an attractive force of a predetermined strength or higher and contained in the patch PA.

Properties of the liquid substance SB contained in the patch PA may be classified in accordance with properties of the patch PA. More specifically, when the patch PA exhibits a hydrophilic property, the patch PA may be bound to a hydrophilic liquid substance SB which is polar in general and contain the hydrophilic liquid substance SB in the three-dimensional micro-cavities. Alternatively, when the patch PA exhibits a hydrophobic property, the hydrophobic liquid substance SB may be contained in the micro-cavities of the three-dimensional mesh structural body NS.

The amount of substance that may be contained in the patch PA may be proportional to a volume of the patch PA. In other words, the amount of substance contained in the patch PA may be proportional to an amount of three-dimensional mesh structural body NS that serves as a support body that contributes to the form of the patch PA. However, there is no constant proportional factor between the amount of substance that may be contained in the patch PA and the volume of the patch PA, and thus the relationship between the amount of substance that may be contained in the patch PA and the volume of the patch PA may be changed in accordance with the design or manufacturing method of the mesh structure.

The amount of substance contained in the patch PA may be reduced due to evaporation, loss, etc. with time. The substance may be additionally injected into the patch PA to increase or maintain the content of the substance contained in the patch PA. For example, a moisture keeping agent for suppressing evaporation of moisture may be added to the patch PA.

The patch PA may be implemented in a form in which it is easy to store the liquid substance SB. This signifies that, when the substance is affected by environmental factors such as humidity level, amount of light, and temperature, the patch PA may be implemented to minimize denaturalization of the substance. For example, to prevent the patch PA from being denaturalized due to external factors such as bacteria, the patch PA may be treated with a bacteria inhibitor.

A liquid substance SB having a plurality of components may be contained in the patch PA. In this case, the substance formed of a plurality of components may be placed together in the patch PA before a reference time point, or a primarily-injected substance may be first contained in the patch PA and then a secondary substance may be contained in the patch PA after a predetermined amount of time. For example, when a liquid substance SB formed of two components is contained in the patch PA, the two components may be contained in the patch PA upon manufacturing the patch PA, only one component may be contained in the patch PA upon manufacturing the patch PA and the other component may be contained therein later, or the two components may be sequentially contained in the patch PA after the patch PA is manufactured.

As described above, the substance contained in the patch may exhibit fluidity, and the substance may move irregularly or be diffused due to molecular motion in the patch PA.

2.1.3 Providing of Reaction Space

Figure 3:
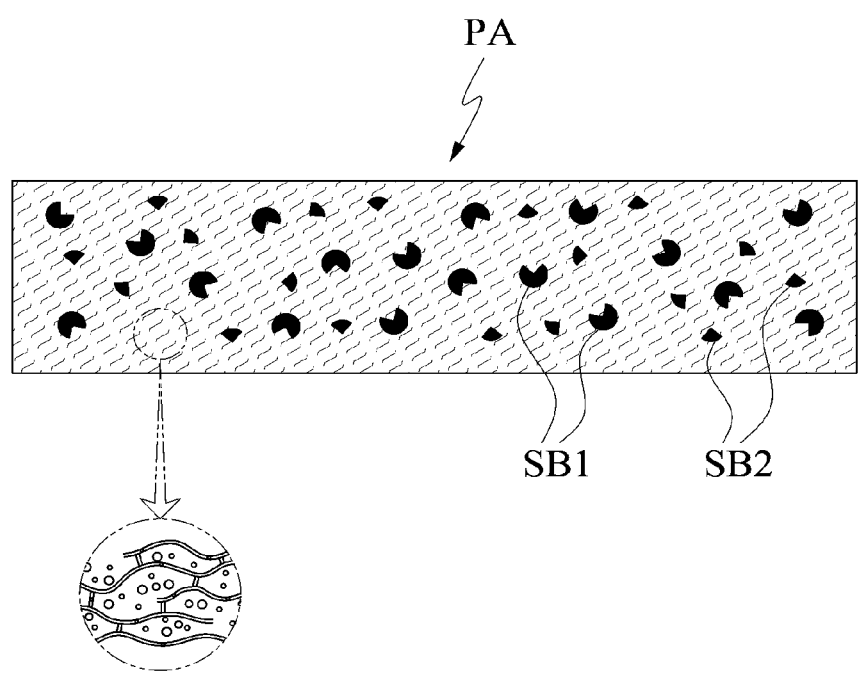
FIG. 3 illustrates providing of a reaction space as an example of a function of a patch according to the present application.
Figure 4:
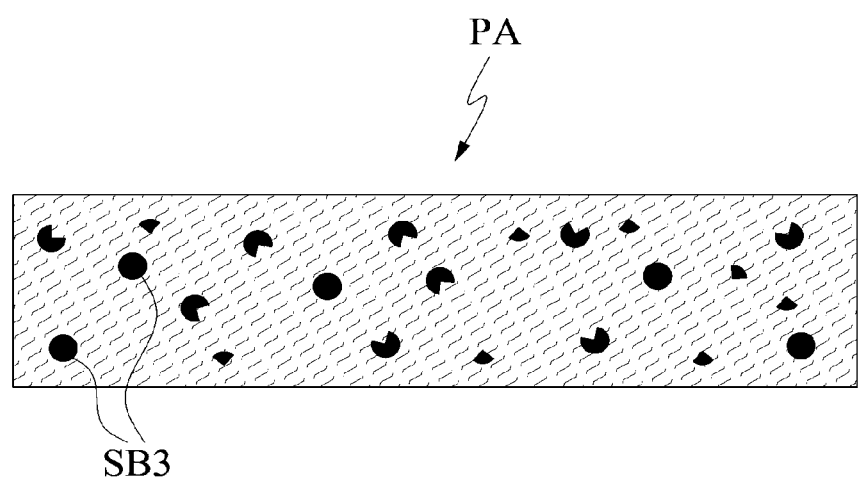
FIG. 4 illustrates providing of a reaction space as an example of a function of a patch according to the present application.

FIGS. 3 and 4 are views illustrating providing a reaction space as an example of a function of the patch according to the present application.

As illustrated in FIGS. 3 and 4, the patch PA according to the present application may perform a function of providing a space. In other words, the patch PA may provide a space in which the liquid substance SB may move through a space formed by the mesh structural body NS and/or a space constituting the mesh structural body NS.

The patch PA may provide a space for activity other than diffusion of particles and/or irregular motion of particles (hereinafter referred to as activity other than diffusion). The activity other than diffusion may refer to a chemical reaction, but is not limited thereto, and may also refer to a physical state change. More specifically, the activity other than diffusion may include a chemical reaction in which a chemical composition of the substance changes after the activity, a specific binding reaction between components included in the substance, homogenization of solutes or particles included in the substance and non-uniformly distributed therein, condensation of some components included in the substance, or a biological activity of a portion of the substance.

When a plurality of substances become involved in the activity, the plurality of substances may be placed together in the patch PA before a reference time point. The plurality of substances may be sequentially inserted into the patch PA.

By changing environmental conditions of the patch PA, efficiency of the function of providing a space for activities other than diffusion in the patch PA may be enhanced. For example, the activity may be promoted or a start of the activity may be induced by changing a temperature condition of the patch PA or adding an electrical condition thereto.

According to FIGS. 3 and 4, a first substance SB1 and a second substance SB2 placed in the patch PA may react inside the patch PA and be deformed into a third substance SB3 or generate the third substance SB3.

2.2 Channel

2.2.1 Meaning

Movement of a substance may occur between the patch PA and an external region. The substance may be moved from the patch PA to the external region of the patch PA or may be moved from the external region to the patch PA.

The patch PA may form a substance movement path or get involved in movement of the substance. More specifically, the patch PA may become involved in movement of the liquid substance SB captured in the patch PA or become involved in movement of an external substance through the liquid substance SB captured in the patch PA. The base substance BS or the additive substance AS may move out from the patch PA, or an external substance may be introduced from an external region to the patch PA.

The patch PA may provide a substance movement path. That is, the patch PA may become involved in movement of the substance and provide a substance movement channel. The patch PA may provide a substance movement channel based on unique properties of the liquid substance SB.

In accordance with whether the patch PA is connected to the external region, the patch PA may be in a state in which the liquid substance SB is movable between the patch PA and the external region or a state in which the liquid substance SB is immovable between the patch PA and the external region. When channeling between the patch PA and the external region begins, the patch PA may have unique functions.

Hereinafter, the state in which the substance is movable and the state in which the substance is immovable will be described first, and the unique functions of the patch PA will be described in detail in connection with whether the patch PA and the external region are connected.

Basically, irregular motion and/or diffusion of the substance are fundamental causes of movement of the liquid substance SB between the patch PA and the external region. However, controlling an external environmental factor (e.g., controlling a temperature condition, controlling an electrical condition, or the like) in order to control movement of a substance between the patch PA and the external region has already been described.

2.2.2 Movable State

In the state in which the substance is movable, a flow may occur between the liquid substance SB captured in the patch PA and/or the substance placed in the external region. In the state in which the substance is movable, substance movement may occur between the liquid substance SB captured in the patch PA and the external region.

For example, in the state in which the substance is movable, the liquid substance SB or some components of the liquid substance SB may be diffused to the external region or moved due to irregular motion. Alternatively, in the state in which the substance is movable, an external substance placed in the external region or some components of the external substance may be diffused to the liquid substance SB in the patch PA or moved due to irregular motion.

The state in which the substance is movable may be caused by contact. The contact may refer to connection between the liquid substance SB captured in the patch PA and the external region. Contact may refer to at least a partial overlap between a flow region of the liquid substance SB and the external region. The contact may refer to the external substance being connected to at least a portion of the patch PA. It may be understood that the range in which the captured liquid substance SB may flow is expanded in the state in which the substance is movable. In other words, in the state in which the substance is movable, the range in which the liquid substance SB may flow may be expanded to include at least a portion of the external region of the captured liquid substance SB. For example, when the liquid substance SB is in contact with the external region, the range in which the captured liquid substance SB may flow may be expanded to include at least a portion of the external region in contact. More specifically, when the external region is an external plate, the region in which the liquid substance SB may flow may be expanded to include a region of the external plate in contact with the liquid substance SB.

2.2.3 Immovable State

In the state in which the substance is immovable, substance movement may not occur between the liquid substance SB captured in the patch PA and the external region. However, substance movement may respectively occur in the liquid substance SB captured in the patch PA and in external substance placed in the external region.

The state in which the substance is immovable may be a state in which the contact is released. In other words, in the state in which contact between the patch PA and the external region is released, substance movement is not possible between the liquid substance SB remaining in the patch PA and the external region or the external substance.

More specifically, the state in which the contact is released may refer to a state in which the liquid substance SB captured in the patch PA is not connected to the external region. The state in which the contact is released may refer to a state in which the liquid substance SB is not connected to an external substance placed in the external region. For example, the state in which movement of the substance is impossible may be caused by separation between the patch PA and the external region.

In the present specification, although "movable state" has a meaning differentiated from that of "immovable state," a transition may occur between the states due to an elapse of time, an environmental change, and the like. In other words, the patch PA may be in the immovable state after being in the movable state, in the movable state after being in the immovable state, or may be in the movable state again, after being in the immovable state after being in the movable state.

2.2.4 Differentiation of Functions

2.2.4.1 Delivery

In the present application, due to the above-described characteristics, the patch PA may deliver at least a portion of the liquid substance SB captured in the patch PA to a desired external region. The delivery of the substance may refer to separation of a portion of the liquid substance SB captured in the patch PA from the patch PA due to a predetermined condition being satisfied. The separation of the portion of the liquid substance SB may refer to the portion of the substance being extracted, emitted, or released from a region that is affected by the patch PA. This is a concept subordinate to the above-described channeling function of the patch PA, and may be understood as defining transfer (delivery) of the substance placed in the patch PA to the outside of the patch PA.

The desired external region may be another patch PA, a dried region, or a liquid region.

The predetermined condition for the delivery to occur may be set as an environmental condition such as a temperature change, a pressure change, a change in an electrical characteristic, and a change in a physical state. For example, when the patch PA is in contact with an object whose force of binding to the liquid substance SB is larger than a force of binding to the mesh structural body NS of the patch PA, the liquid substance SB may be chemically bound with the object in contact, and as a result, at least a portion of the liquid substance SB may be provided to the object.

Hereinafter, for convenience, the above-described function of the patch PA will be referred to as "delivery."

The delivery may occur between the patch PA and the external region, via the state in which the liquid substance SB is movable and the state in which the liquid substance SB is immovable between the patch PA and the external region.

More specifically, when the liquid substance SB is in the movable state, the liquid substance SB may be diffused between the patch PA and the external region or may be moved to the external region due to irregular motion. In other words, the base solution and/or the additive substance AS included in the liquid substance SB may be moved from the patch PA to the external region. In the state in which the liquid substance SB is immovable, the liquid substance SB is unable to move between the patch PA and the external region. In other words, due to a transition from the movable state to the immovable state, a portion of the substance that has moved from the patch PA to the external region due to diffusion and/or irregular motion of the liquid substance SB become unable to move back to the patch PA. Thus, a portion of the liquid substance SB may be provided to the external region.

The delivery may be performed due to a difference between an attractive force between the liquid substance SB and the mesh structural body NS and an attractive force between the liquid substance SB and the external region or the external substance. The attractive force may be caused by similarity between polarities or a specific binding relationship.

More specifically, when the liquid substance SB is hydrophilic and the external region or the external substance is more hydrophilic than the mesh structural body NS, at least a portion of the liquid substance SB captured in the patch PA may be provided to the external region via the movable state and the immovable state.

The delivery of the liquid substance SB may also be performed selectively. For example, when a specific binding relationship exists between some components included in the liquid substance SB and the external substance, some of the ingredients may be selectively delivered via the state in which the substance is movable and the state in which the substance is immovable.

More specifically, when it is assumed that the patch PA provides a substance to an external plate PL, which is in a form of a flat plate, a substance that binds specifically to a portion of the liquid substance SB captured in the patch PA (e.g., a portion of a solute) may be applied on the external plate PL. In this case, the patch PA may selectively deliver a portion of the solute that binds specifically to the substance applied on the external plate PL from the patch PA to the plate PL via the movable state and the immovable state.

The delivery as a function of the patch PA will be described below according to a few examples of different regions to which the substance is moved. However, in giving the detailed description, the concepts of "release" of the liquid substance SB and "delivery" of the liquid substance SB may be interchangeably used.

Here, a case in which the liquid substance SB is provided from the patch PA to a separate external plate PL will be described. For example, a case in which the substance is moved from the patch PA to a plate PL, such as a slide glass, may be taken into consideration.

As the patch PA and the plate PL come into contact, at least a portion of the liquid substance SB captured in the patch PA is diffused to the plate PL or moved due to irregular motion. When the contact between the patch PA and the plate PL is released, the portion of the substance that has been moved from the patch PA to the plate PL (that is, the portion of the liquid substance SB) become unable to move back to the patch PA. As a result, the portion of the substance may be provided from the patch PA to the plate PL. In this case, the portion of the substance being provided may be the additive substance AS. For a substance in the patch PA to be "provided" by the contact and separation, an attractive force and/or binding force that acts between the substance and the plate PL should be present, and the attractive force and/or the binding force should be larger than the attractive force acting between the substance and the patch PA. Therefore, if the above-described "delivery condition" is not satisfied, delivery of a substance may not occur between the patch PA and the plate PL.

The delivery of a substance may be controlled by providing a temperature condition or an electrical condition to the patch PA.

The movement of a substance from the patch PA to the plate PL may depend on an extent of a contact area between the patch PA and the plate PL. For example, the substance movement efficiency between the patch PA and the plate PL may be increased or decreased in accordance with an extent of an area in which the patch PA and the plate PL come into contact.

When the patch PA includes a plurality of components, only some of the components may be selectively moved to the external plate PL. More specifically, a substance that binds specifically to some of the plurality of components may be fixed to the external plate PL. In this case, the substance fixed to the external plate PL may be in a liquid or solid state, or may be fixed to a different region. In this case, a portion of the substance of the plurality of components moves to the plate PL and binds specifically to the plate PL due to contact between the patch PA and the different region, and when the patch PA is separated from the plate PL, only some of the components may be selectively released to the plate PL.

Figure 5:
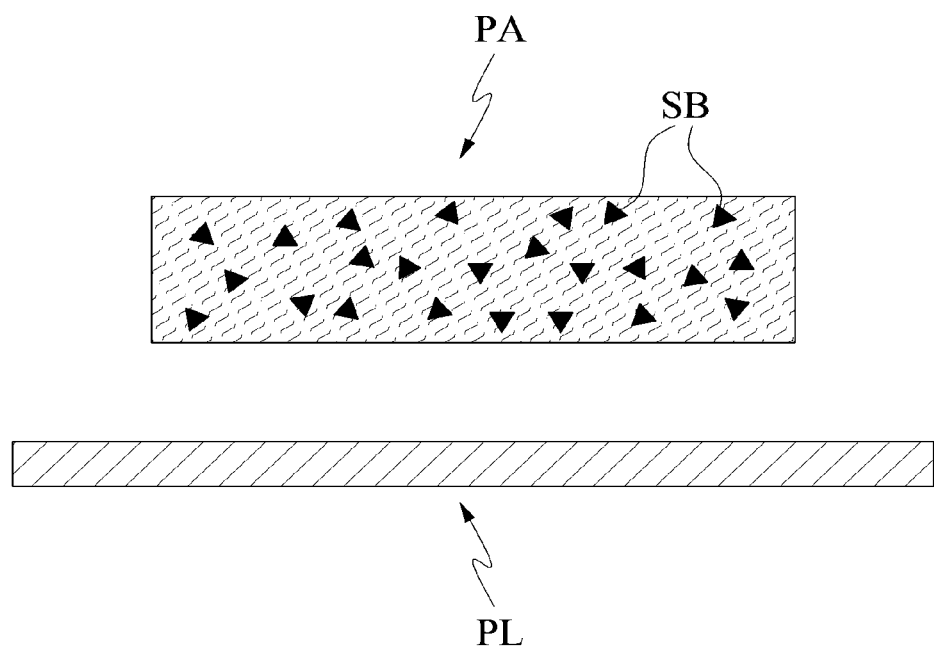
FIG. 5 illustrates providing of a substance as an example of a function of a patch according to the present application.
Figure 6:
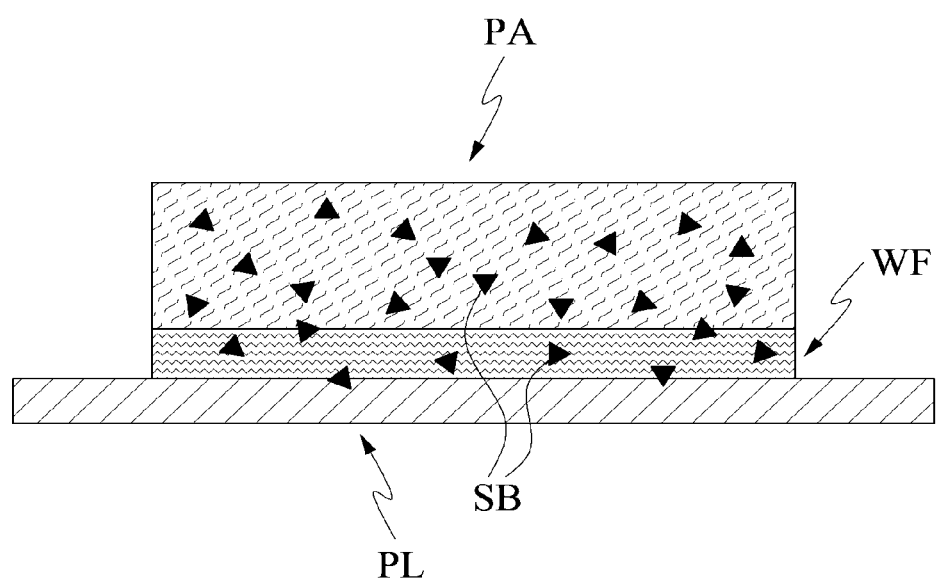
FIG. 6 illustrates providing of a substance as an example of a function of a patch according to the present application.
Figure 7:
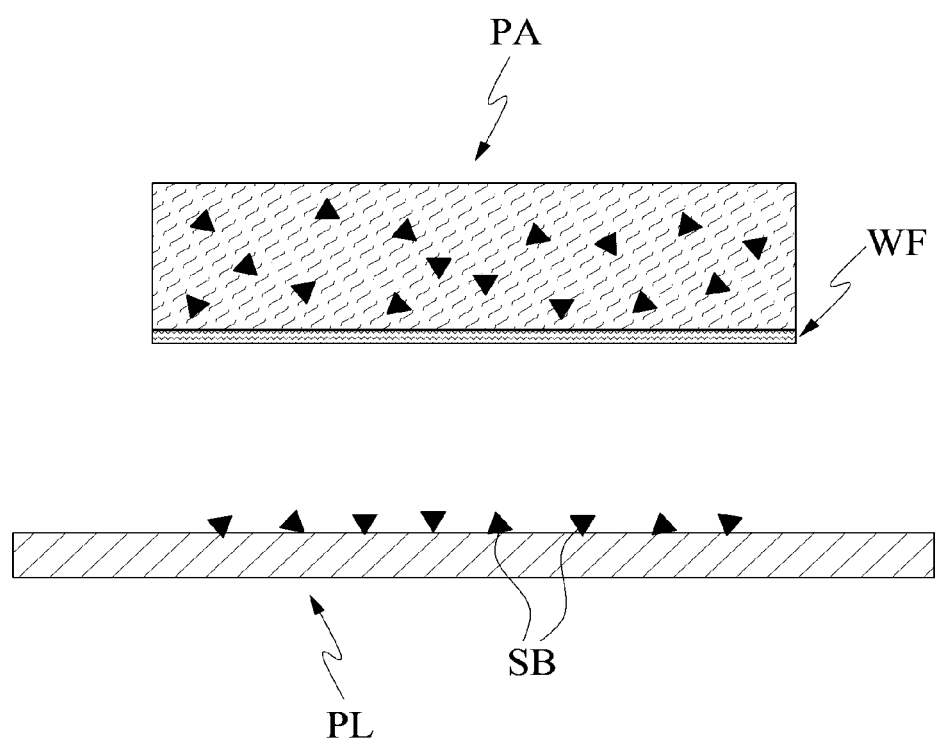
FIG. 7 illustrates providing of a substance as an example of a function of a patch according to the present application.

FIGS. 5 to 7 illustrate delivery of a substance from the patch PA to the external plate PL as an example of delivery of a substance from among the functions of the patch PA according to the present application. According to FIGS. 5 to 7, by the patch PA coming into contact with the external plate PL, a portion of a substance contained in the patch PA may be provided to the plate PL. In this case, providing of the substance may become possible by the patch PA coming into contact with the plate so that the substance is movable. In this case, a water film WF may be formed in the vicinity of a contact surface at which the plate and the patch PA come into contact, and the substance may be movable through the formed water film WF.

Here, a case in which the liquid substance SB is provided from the patch PA to a substance having fluidity SL will be described. The substance having fluidity SL may be a liquid substance that is held in other containing space or that is flowing.

As the patch PA and the substance having fluidity come into contact (for example, the patch PA is put into a solution), at least a portion of the liquid substance SB captured in the patch PA may be diffused or moved due to irregular motion to the substance having fluidity SL. When the patch PA and the substance having fluidity SL are separated, a portion of the liquid substance SB that has been moved from the patch PA to the substance having fluidity become unable to move back to the patch PA so that a portion of the substance in the patch PA may be provided to the substance having fluidity.

The substance movement between the patch PA and the substance having fluidity SL may depend on an extent of a contact area between the patch PA and the substance having fluidity SL. For example, the substance movement efficiency between the patch PA and the substance having fluidity SL may be increased or decreased in accordance with an extent of an area at which the patch PA and the substance having fluidity SL come into contact (for example, a depth at which the patch PA is immersed into a solution or the like).

The substance movement between the patch PA and the substance having fluidity SL may be controlled through physical separation between the patch PA and the substance having fluidity.

A partial concentration of the additive substance AS in the liquid substance SB and a partial concentration of the additive substance AS in the substance having fluidity may be different, and the additive substance AS may be provided from the patch PA to the substance having fluidity.

However, in the patch PA providing the liquid substance SB to the substance having fluidity SL, the physical separation between the patch PA and the substance having fluidity SL is not essential. For example, when a force (driving force/casual force) that causes a substance to move from the patch PA to a liquid having fluidity disappears or is decreased to a reference value or lower, the movement of the substance may be stopped.

In "delivery" between the patch PA and the substance having fluidity SL, the above-described "delivery condition" between the patch PA and the substance having fluidity SL may not be required. It may be understood that substances that have already moved to the substance having fluidity SL are diffused and/or moved due to irregular motion in the substance having fluidity SL, and the substance has been provided to the substance having fluidity SL when a distance between the moved substance and the patch PA become larger a predetermined distance. Since, while in the case of the plate PL, a movable range expanded due to the contact is extremely limited, and thus the attractive force between the patch PA and the substances that have moved to the plate PL may be significant, in the relationship between the patch PA and the substance having fluidity, a movable range expanded due to contact between the patch PA and the plate PL is relatively much wider, and thus the attractive force between the patch PA and the substances that have moved to the substance having fluidity SL is insignificant.

Figure 8:
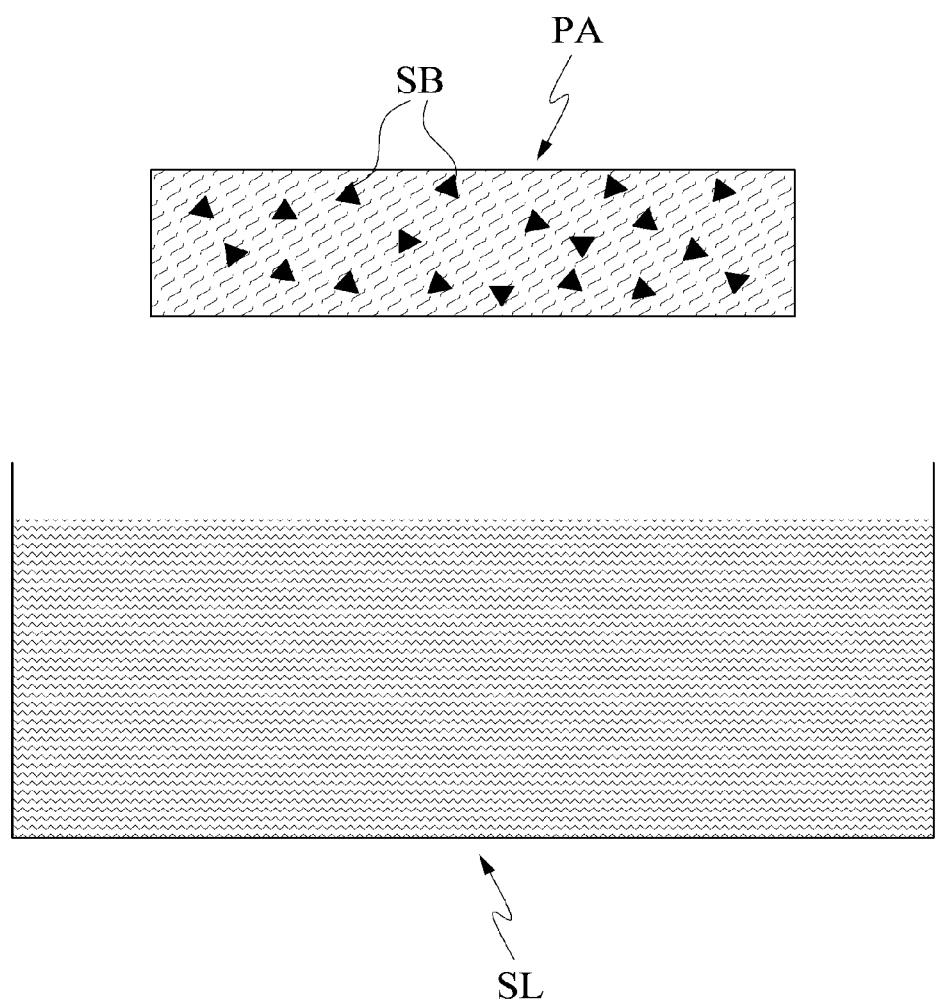
FIG. 8 illustrates providing of a substance as an example of a function of a patch according to the present application.
Figure 9:
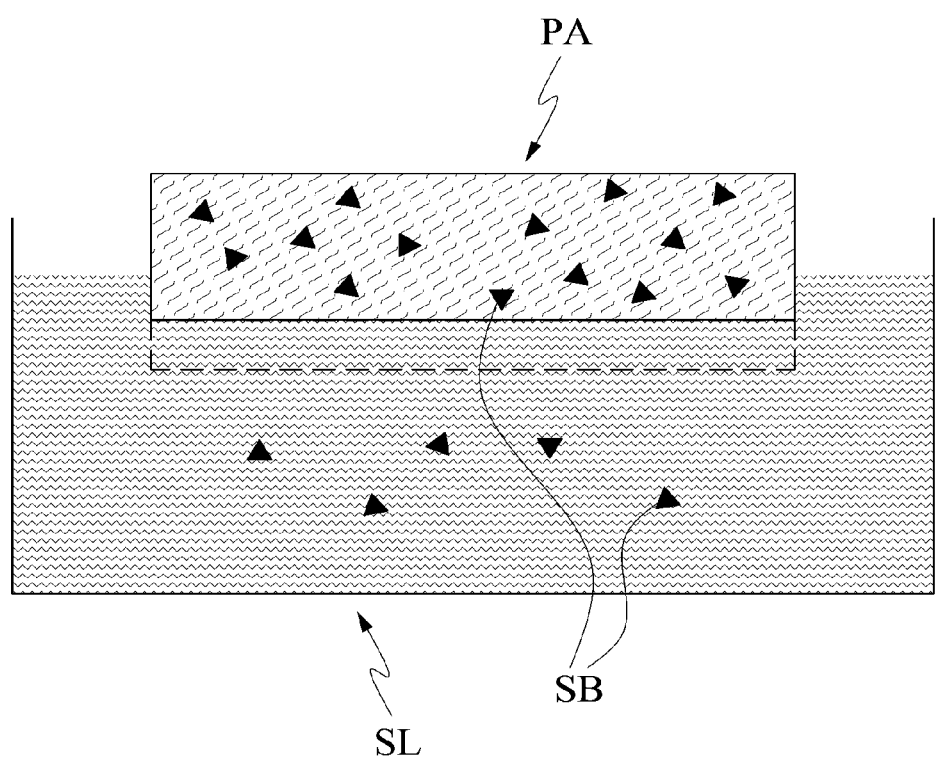
FIG. 9 illustrates providing of a substance as an example of a function of a patch according to the present application.
Figure 10:
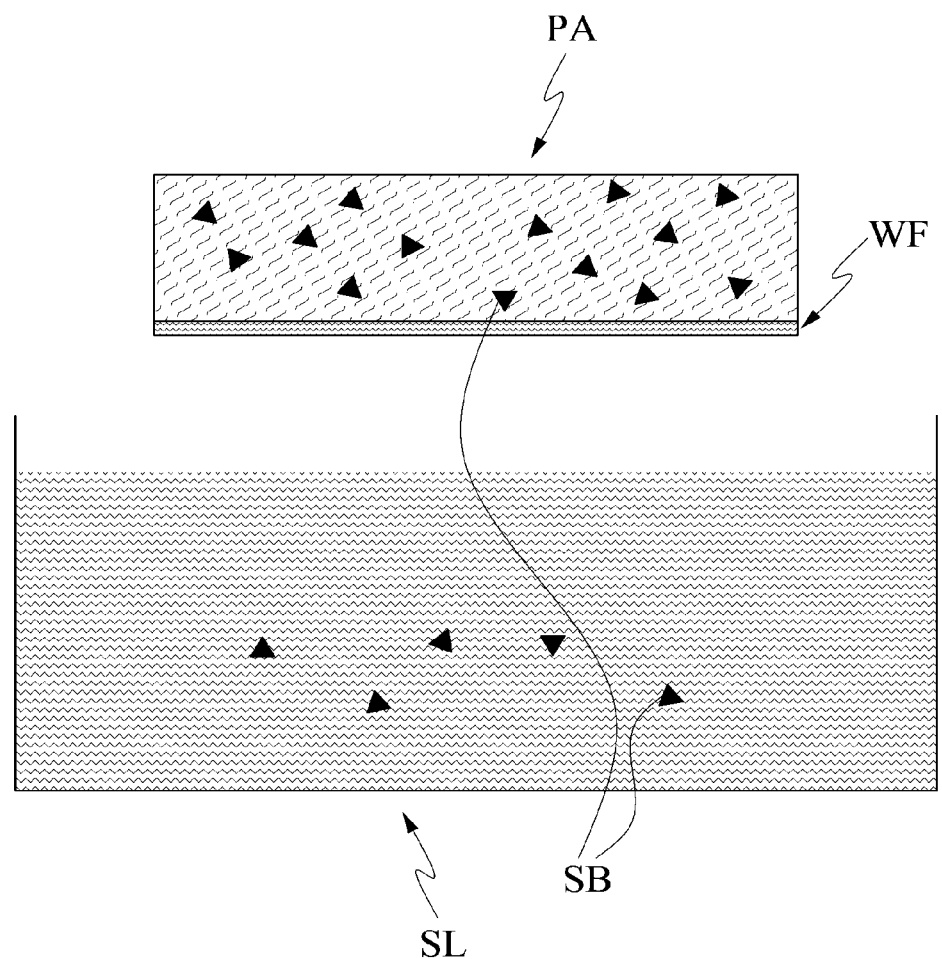
FIG. 10 illustrates providing of a substance as an example of a function of a patch according to the present application.

FIGS. 8 to 10 illustrate delivery of a substance from the patch PA to the substance having fluidity as an example of delivery of a substance from among the functions of the patch PA according to the present application. According to FIGS. 8 to 10, the patch PA may deliver a portion of a substance contained in the patch PA to an external substance having fluidity. The delivery of the portion of the contained substance may be performed by the patch PA being inserted into or coming into contact with the substance having fluidity so that substance movement is possible between the liquid substance SB captured in the patch PA and the substance having fluidity.

Here, it is assumed that a substance is moved from the patch PA to another patch PA. In a contact region in which the patch PA and the other patch PA are in contact, at least a portion of the liquid substance B provided in the patch PA may be moved to the other patch PA.

In the contact region, the liquid substance SB provided in each patch PA may be diffused and moved to the other patch PA. In this case, due to the movement of the substance, a concentration of the liquid substance SB provided in each patch PA may be changed. Also in the present embodiment, as described above, the patch PA and the other patch PA may be separated, and a portion of the liquid substance SB in the patch PA may be provided to the other patch PA.

The substance movement between the patch PA and other patch PA may be performed through a change in an environmental condition including a change in a physical state.

The substance movement between the patch PA and another patch PA may depend on an extent of a contact area between the patch PA and the other patch PA. For example, the substance movement efficiency between the patch PA and the other patch PA may be increased or decreased in accordance with an extent of an area where the patch PA comes into contact with the other patch PA.

Figure 11:
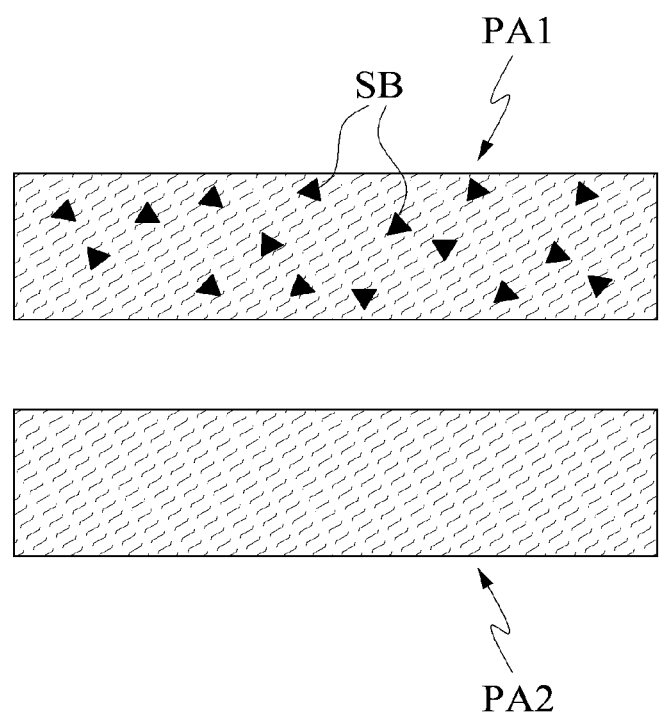
FIG. 11 illustrates providing of a substance as an example of a function of a patch according to the present application.
Figure 12:
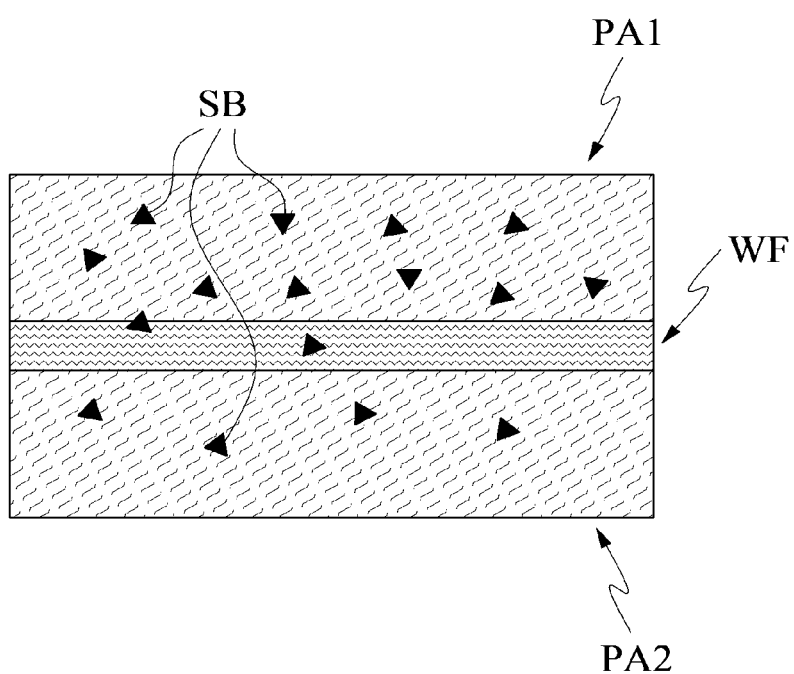
FIG. 12 illustrates providing of a substance as an example of a function of a patch according to the present application.
Figure 13:
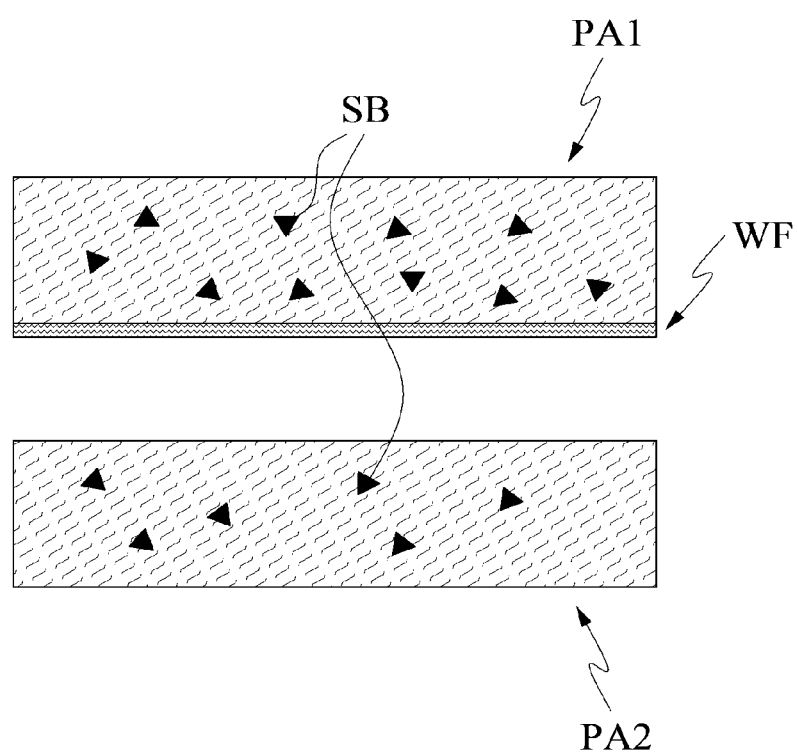
FIG. 13 illustrates providing of a substance as an example of a function of a patch according to the present application.

FIGS. 11 to 13 illustrate delivery of a substance from a patch PA1 to another patch PA2 as an example of delivery of a substance among the functions of the patch PA according to the present application. According to FIGS. 11 to 13, the patch PA1 may deliver a portion of a substance contained in the patch PA1 to the other patch PA2. The delivery of the portion of the substance may be performed by the patch PA1 coming into contact with the other patch PA2 and becoming a state in which a liquid substance SB captured in the patch PA1 and a substance captured in the other patch PA2 are exchangeable.

2.2.4.2 Absorption

Prior to description, it should be noted that, among the functions of the patch PA according to the present application, "absorption" may be managed similarly as the above-described "delivery" in some embodiments. For example, in a case in which a substance moves due to a concentration differences between substances, the "absorption" may be similar to the "delivery" in that a concentration of the liquid substance SB, particularly, a concentration of the additive substance AS, may be changed to control a direction in which the substance is moved. The "absorption" may also be similar to "delivery" in terms of controlling movement and selective absorption of a substance through a release of physical contact with the patch PA, and this may be clearly understood by those of ordinary skill in the art to which the present application pertains.

Due to the above-described characteristics, the patch PA according to the present application may capture an external substance. The patch PA may pull in an external substance present outside a region defined by the patch PA toward a region affected by the patch PA. The pulled external substance may be captured along with the liquid substance SB of the patch PA. The pulling of the external substance may be caused by an attractive force between the external substance and the liquid substance SB already captured in the patch PA. Alternatively, the pulling of the external substance may be caused by an attractive force between the external substance and a region of the mesh structural body NS not occupied by the liquid substance SB. The pulling of the external substance may be caused by a force of surface tension.

Hereinafter, for convenience, the above-described function of the patch PA will be referred to as "absorption." Absorption may be understood as a concept subordinate to the above-described channeling function of the patch PA, the concept defining movement of an external substance to the patch PA.

The absorption may occur by the patch PA via a state in which the substance is movable and a state in which the substance is immovable.

A substance that is absorbable by the patch PA may be in a liquid or solid state. For example, when the patch PA comes into contact with an external substance including a solid state substance, absorption of the substance may be performed due to an attractive force between the solid state substance included in the external substance and the liquid substance SB placed in the patch PA. As another example, when the patch PA comes into contact with a liquid external substance, the absorption may be performed due to binding between the liquid external substance and the liquid substance SB placed in the patch PA.

The external substance absorbed into the patch PA may be moved to the inside of the patch PA through the microcavities of the mesh structural body NS forming the patch PA or may be distributed on a surface of the patch PA. Positions at which the external substance is distributed may be set on the basis of a molecular weight or a particle size of the external substance.

While the absorption is performed, the form of the patch PA may be changed. For example, the volume, color, and the like of the patch PA may be changed. While the absorption into the patch PA is being performed, the absorption into the patch PA may be activated or delayed by adding external conditions such as a temperature change and a physical state change to an absorption environment of the patch PA.

The absorption will be described below as a function of the patch PA according to some examples of an external region that provides a substance to be absorbed into the patch PA when the absorption occurs.

Hereinafter, it will be assumed that the patch PA absorbs an external substance from an external plate PL. An example of the external plate may include a plate PL in which the external substance may be placed while the external substance is not absorbed thereinto.

A substance may be applied on the external plate PL. Particularly, a substance may be applied in a form of powder on the plate PL. The substance applied on the plate PL may be a single component or a mixture of a plurality of components.

The plate PL may have the shape of a flat plate. The shape of the plate PL may be deformed for improvement in ability to contain the substance or the like. For example, a well may be formed to improve the ability to contain the substance, a surface of the plate PL may be deformed by engraving or embossing, or a patterned plate PL may be used to improve contact with the patch PA.

The absorption of a substance from the plate PL by the patch PA according to the present application may be performed through contact between the plate PL and the patch PA. In this case, in a contact region in the vicinity of a contact surface between the plate PL and the patch PA, a water film WF may be formed due to the liquid substance SB captured in the patch PA and/or the substance applied on the plate PL. When the water film (aquaplane, hydroplane) WF is formed in the contact region, the substance applied on the plate PL may be captured by the water film WE The substance captured in the water film WF may freely flow within the patch PA.

When the patch PA is spaced a predetermined distance or more apart and separated from the plate PL, the water film WF may be moved along with the patch PA, and the substance applied on the plate PL may be absorbed into the patch PA. The substance applied on the plate PL may be absorbed into the patch PA as the patch PA is separated a predetermined distance or more apart from the plate PL. When the patch PA and the plate PL are spaced apart and separated, the liquid substance SB provided to the patch PA may not be moved to the plate PL, or only an insignificant amount thereof may be absorbed into the patch PA.

A portion of or the entire substance applied on the plate PL may react specifically with a portion of or the entire substance captured in the patch PA. In this respect, absorption of a substance from the plate PL by the patch PA may be selectively performed. Particularly, the absorption may be performed selectively when the patch PA has a stronger attractive force than the plate PL with respect to a portion of the substance captured in the patch PA.

As an example, a portion of the substance may be fixed to the plate PL. In other words, a portion of the substance may be fixed to the plate PL while another portion of the substance is applied to have fluidity or not be fixed. In this case, when the patch PA and the plate PL are brought into contact and separated, the substance, excluding the portion of the substance fixed to the plate PL of the substance applied on the plate PL, may be selectively absorbed into the patch PA. Instead, the selective absorption may also occur due to polarities of a substance placed on the plate PL and a substance captured in the patch PA regardless of whether the substance is fixed.

As another example, when the liquid substance SB captured in the patch PA is bound specifically to at least a portion of a substance applied on the plate PL, only the portion of the substance applied on the plate PL bound specifically to the liquid substance SB may be absorbed into the patch PA when the patch PA is brought into contact with and then separated from the substance applied on the plate PL.

As yet another example, a portion of the substance applied on the plate PL may react specifically with a substance fixed to the plate PL in advance. In this case, only a remaining substance, excluding the substance that reacts specifically with the substance fixed to the plate PL in advance of the substance being applied to the plate PL, may be absorbed into the patch PA.

Figure 14:
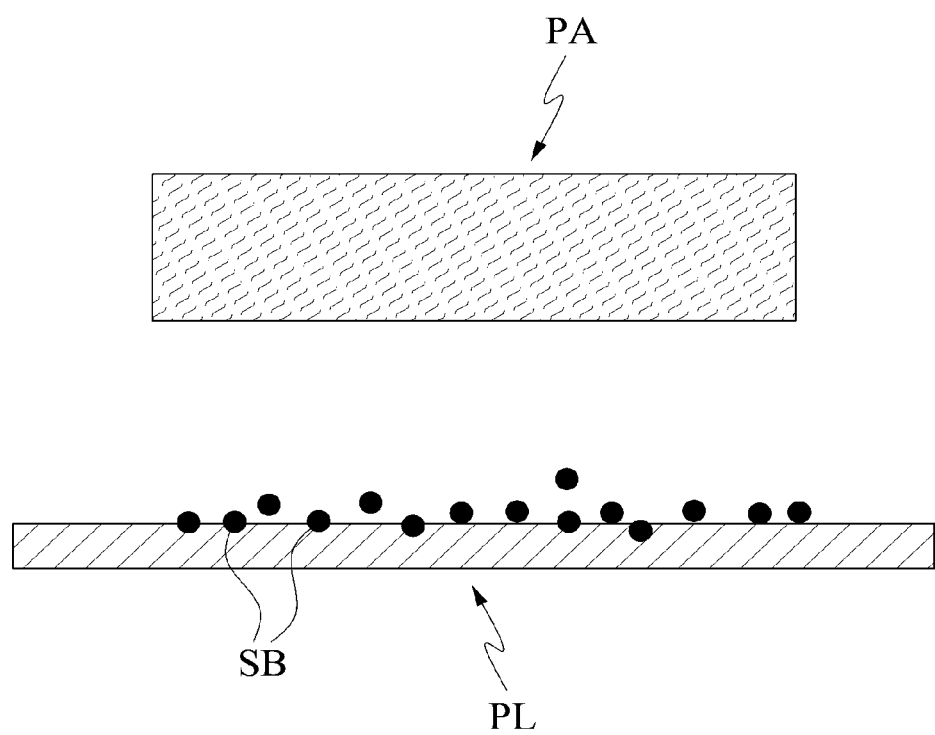
FIG. 14 illustrates absorbing of a substance as an example of a function of a patch according to the present application.
Figure 15:
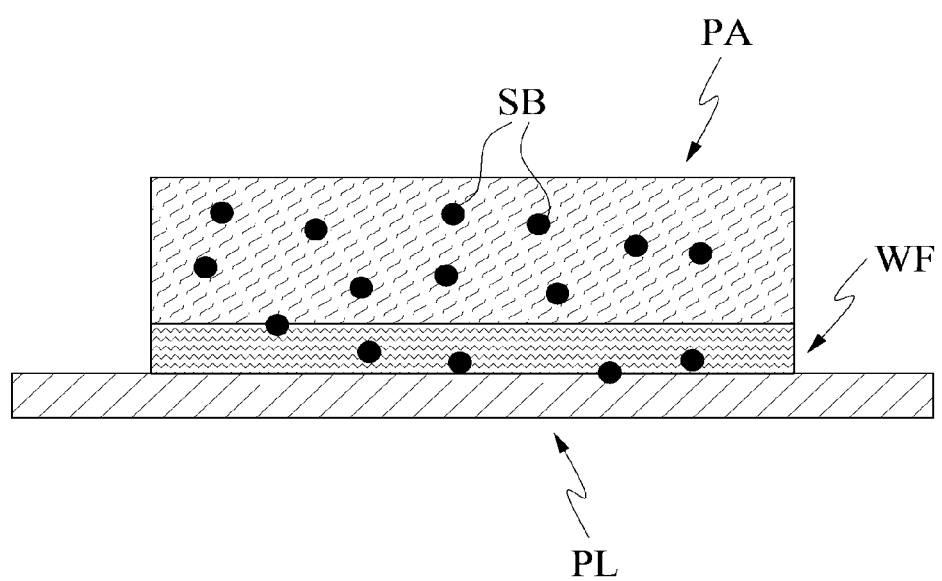
FIG. 15 illustrates absorbing of a substance as an example of a function of a patch according to the present application.
Figure 16:
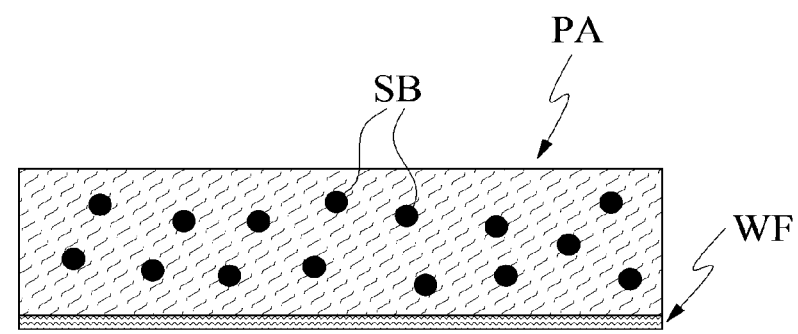
FIG. 16 illustrates absorbing of a substance as an example of a function of a patch according to the present application.
Figure 16:
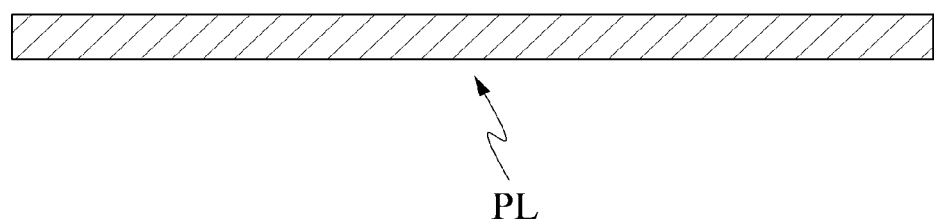

FIGS. 14 to 16 illustrate absorption of a substance from an external plate PL by the patch PA as an example of absorption of a substance from among the functions of the patch PA according to the present application. According to FIGS. 14 to 16, the patch PA may absorb a portion of a substance placed on the external plate PL from the external plate PL. The absorption of the substance may be performed by the patch PA coming into contact with the external plate PL, the water film WF being formed in the vicinity of a contact region between the external plate PL and the patch PA, and the substance being movable to the patch PA through the water film WF.

Here, it will be assumed that a substance is absorbed into the patch PA from the substance having fluidity SL. The substance having fluidity SL may refer to a liquid external substance that is held in other containing space or that is flowing. More specifically, by having an environment in which the substance having fluidity SL and the liquid substance SB captured in the patch PA may flow to and from each other, a portion of or the entire substance having fluidity SL may be absorbed into the patch PA. In this case, the environment in which the substance having fluidity SL and the liquid substance SB may flow to and from each other may be formed by the patch PA coming into contact with at least a portion of the substance having fluidity SL.

When the patch PA comes into contact with the substance having fluidity SL, the patch PA may be in a state in which a substance is movable from the substance having fluidity SL. When the patch PA is separated from the substance having fluidity SL, at least a portion of the substance having fluidity SL may be absorbed into the patch PA.

The absorption of a substance into the patch PA from the substance having fluidity SL may depend on a concentration difference between the substance captured in the patch PA and the substance having fluidity SL. In other words, when the concentration of the liquid substance SB captured in the patch PA with respect to a predetermined additive substance AS is lower than the concentration of the substance having fluidity SL with respect to the predetermined additive substance AS, the predetermined additive substance AS may be absorbed into the patch PA.

When a substance is absorbed into the patch PA from the substance having fluidity SL, in addition to the absorption depending on the concentration difference while the patch PA and the substance having fluidity SL are in contact as described above, the absorption into the patch PA may also be controlled by adding an electrical factor or changing a physical condition. Further, without direct contact between the substance captured in the patch PA and a substance to be absorbed, the absorption of a substance may also be performed through indirect contact therebetween via a medium.

Figure 17:
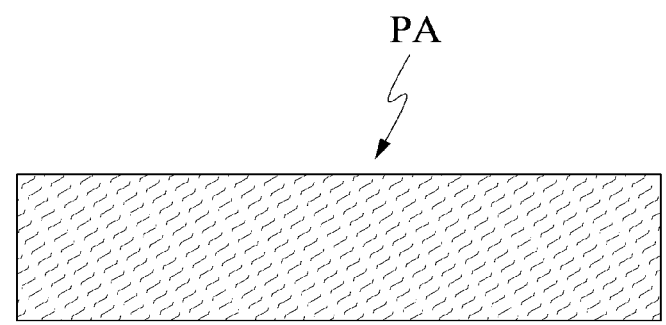
FIG. 17 illustrates absorbing of a substance as an example of a function of a patch according to the present application.
Figure 17:
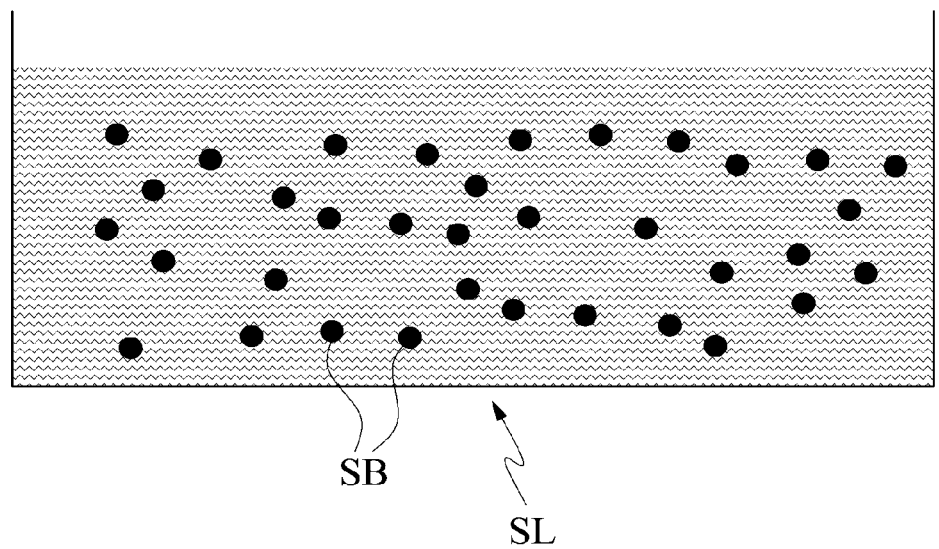
Figure 18:
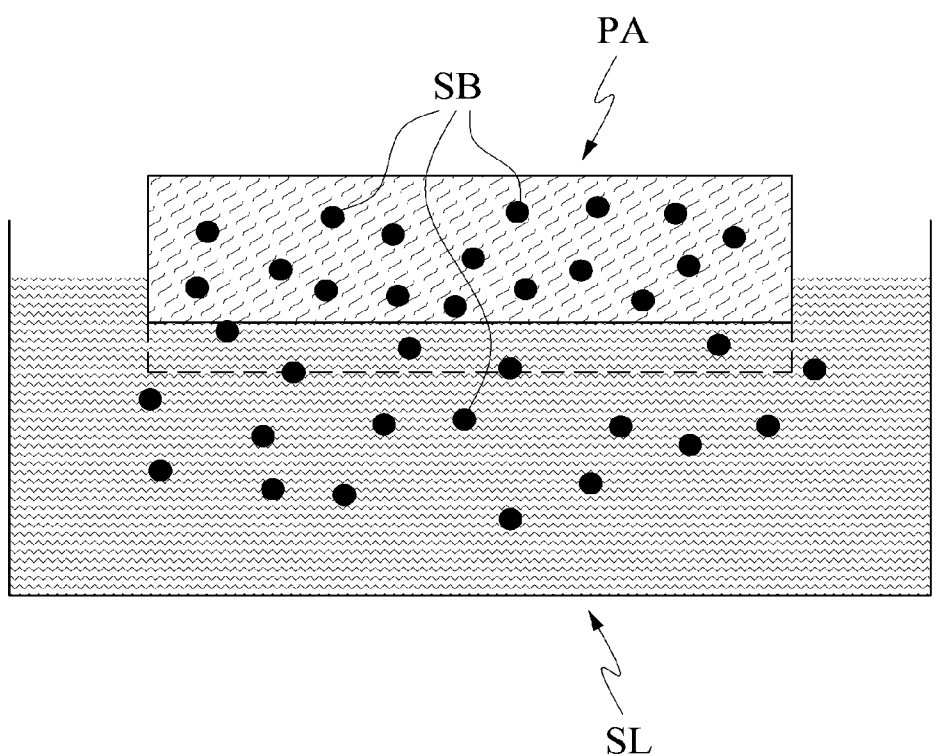
FIG. 18 illustrates absorbing of a substance as an example of a function of a patch according to the present application.
Figure 19:
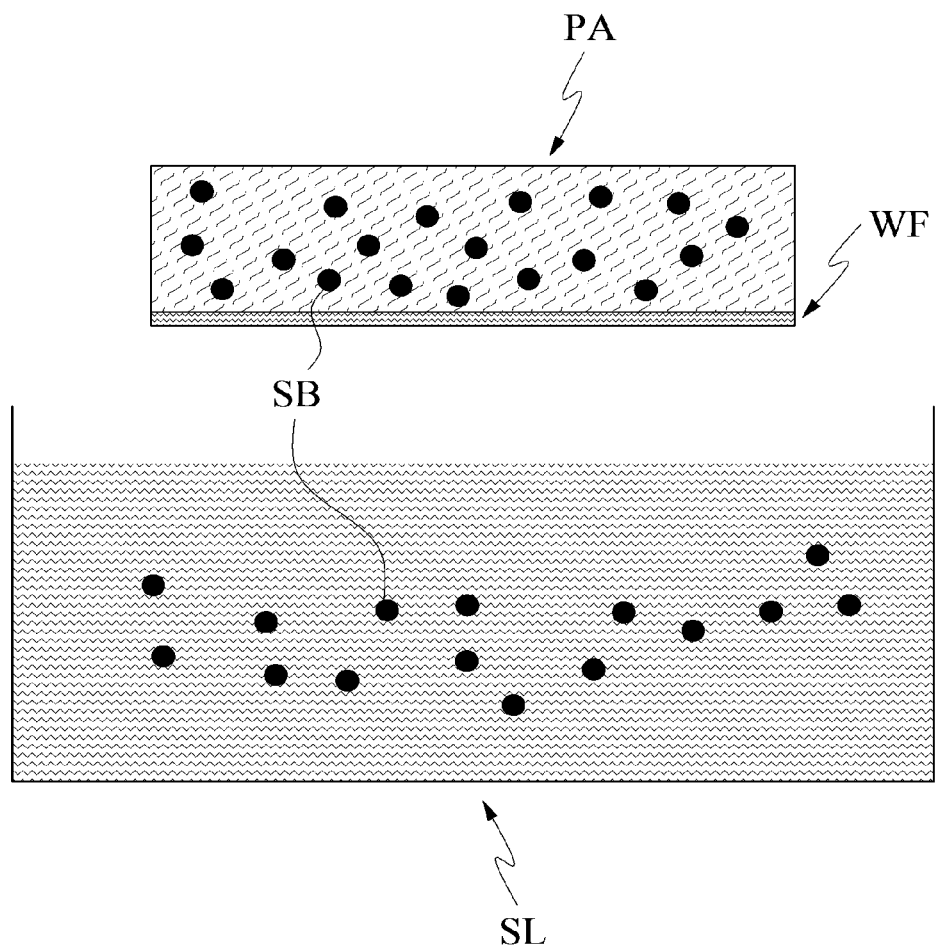
FIG. 19 illustrates absorbing of a substance as an example of a function of a patch according to the present application.

FIGS. 17 to 19 illustrate absorption of a substance from the substance having fluidity SL by the patch PA as an example of absorption of a substance from among the functions of the patch PA according to the present application. According to FIGS. 17 to 19, the patch PA may absorb a portion of the substance having fluidity SL. The absorption of a substance may be performed by the patch PA being immersed into the substance having fluidity SL or coming into contact with the substance having fluidity SL so that the liquid substance SB captured in the patch PA and the substance having fluidity SL are movable to and from each other.

Here, it will be assumed that the patch PA absorbs an external substance from another patch PA.

The absorption of an external substance from another patch PA by the patch PA may be performed due to a difference in binding force between the absorbed external substance and the substance already captured in the patch PA and between the absorbed external substance and the external substance not absorbed into the patch PA. For example, when the absorbed substance exhibits hydrophilic property, the patch PA exhibits hydrophilic property, and an attractive force between the absorbed substance and the patch PA is stronger than an attractive force between the other patch PA and the absorbed substance (that is, when the patch PA is more hydrophilic than the other patch PA), at least a portion of the external substance may be absorbed into the patch PA when the patch PA and the other patch PA are separated after being brought into contact.

Figure 20:
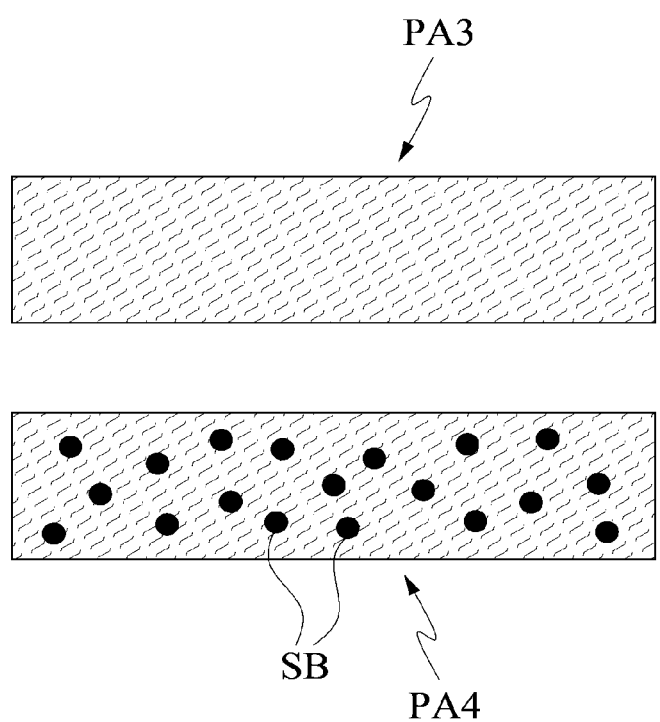
FIG. 20 illustrates absorbing of a substance as an example of a function of a patch according to the present application.
Figure 21:
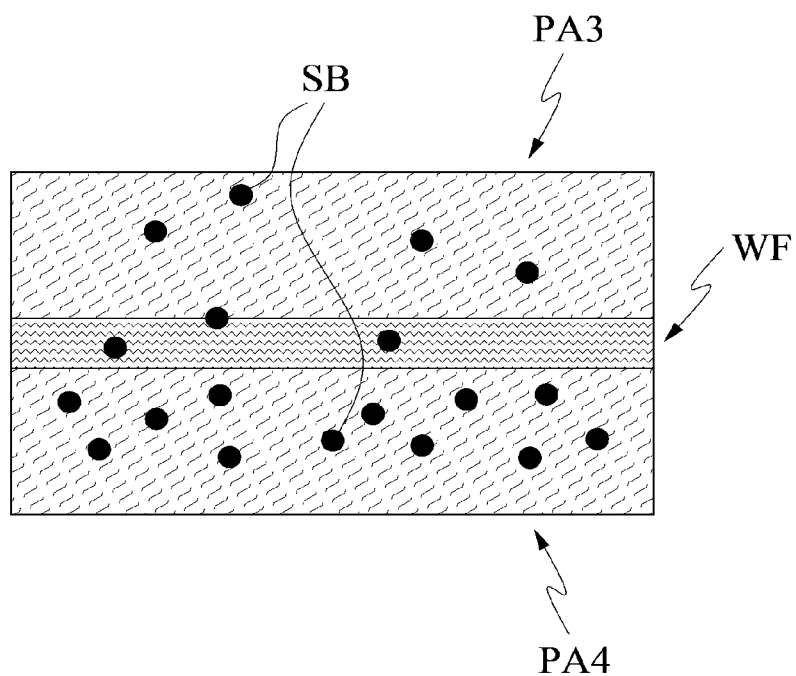
FIG. 21 illustrates absorbing of a substance as an example of a function of a patch according to the present application.
Figure 22:
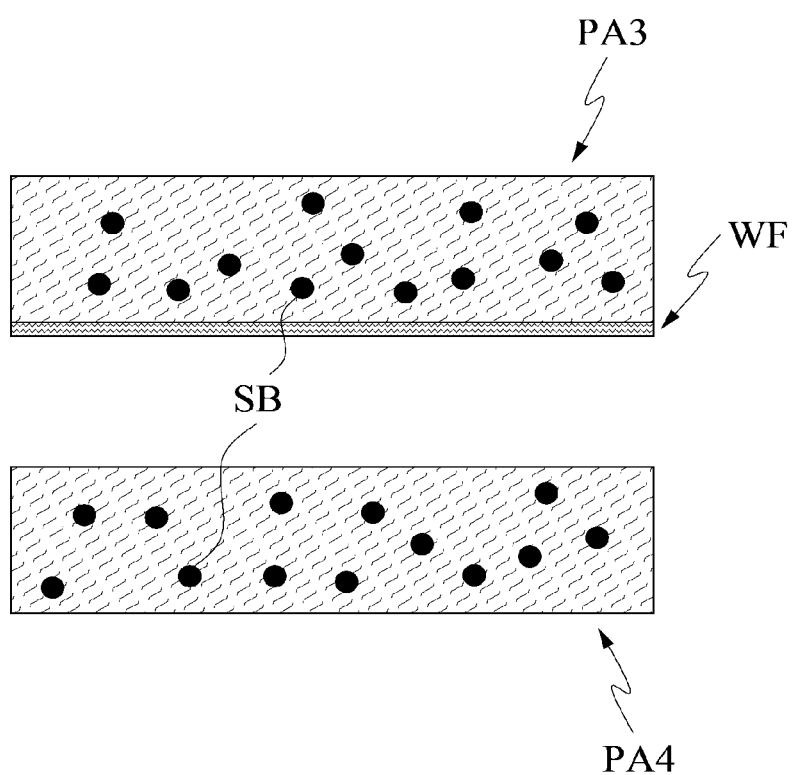
FIG. 22 illustrates absorbing of a substance as an example of a function of a patch according to the present application.

FIGS. 20 to 22 illustrate absorption of a substance from another patch PA4 by a patch PA3 as an example of absorption of a substance among the functions of the patch PA according to the present application. According to FIGS. 20 to 22, the patch PA3 may absorb a portion of a substance placed in the other patch PA4. The absorption of the substance may be performed by the patch PA3 coming into contact with the other patch PA4 so that a liquid substance SB captured in the patch PA3 and a liquid substance SB captured in the other patch PA4 are exchangeable.

A binding force of the patch PA to the external substance absorbed thereinto may be changed in accordance with a proportion of a frame structural body of the three-dimensional mesh structural body NS constituting the patch PA with respect to the total volume of the patch PA. For example, as the proportion of a volume occupied by the frame structural body in the entire patch PA increases, the amount of substance captured in the structural body may be reduced. In this case, a binding force between the patch PA and a target substance may be reduced due to a reason such as reduction in a contact area between the target substance and the substance captured in the patch PA.

In relation to this, ratios of materials that constitutes the mesh structural body NS may be adjusted during manufacturing process of the patch PA so that polarity of the patch PA is controlled. For example, in the case of a patch PA manufactured using agarose, a concentration of the agarose may be controlled to adjust a degree of the absorption.

When the certain region has a weaker binding force than the patch PA with respect to a substance provided from the patch PA, and the patch PA and another patch PA are brought into contact and then separated, the absorbed external substance may be separated from the other patch PA along with the patch PA.

2.2.4.3 Providing of Environment

Due to the above-described characteristics, the patch PA according to the present application may perform a function of adjusting an environmental condition of a desired region. The patch PA may provide an environment due to the patch PA to the desired region.

The environmental condition due to the patch PA may depend on the liquid substance SB captured in the patch PA. The patch PA may create a desired environment in a substance placed in an external region on the basis of characteristics of a substance accommodated in the patch PA or for a purpose of making the environment correspond to characteristics of the substance accommodated in the patch PA.

The adjustment of the environment may be understood as changing an environmental condition of the desired region. The changing of the environmental condition of the desired region may be implemented in a form in which a region affected by the patch PA is expanded to include at least a portion of the desired region or a form in which an environment of the patch PA is shared with the desired region.

Hereinafter, for convenience, the above-described function of the patch PA will be referred to as "providing of an environment."

The providing of an environment by the patch PA may be performed in a state in which a substance is movable between the patch PA and an external region subject to provide the environment. The providing of an environment by the patch PA may be performed through contact. For example, when the patch PA comes into contact with a desired region (for example, an external substance, a plate PL, or the like), a specific environment may be provided to the desired region by the patch PA.

The patch PA may adjust an environment of a target region TA by providing an environment with an appropriate pH, osmotic pressure, humidity level, concentration, temperature, and the like. For example, the patch PA may provide fluidity (liquidity) to the target region TA or a target substance. Such providing of fluidity may occur due to movement of a portion of a substance captured in the patch PA. A moist environment may be provided to the target region TA through the liquid substance SB or the base substance BS captured in the patch PA.

The environmental factors provided by the patch PA may be constantly maintained in accordance with a purpose. For example, the patch PA may provide homeostasis to the desired region. As another example, as a result of providing an environment, the substance captured in the patch PA may be adapted to an environmental condition of the desired region The providing of an environment by the patch PA may result from diffusion of the liquid substance SB included in the patch PA. That is, when the patch PA and the desired region come into contact, a substance may be movable through a contact region that is formed due to contact between the patch PA and the desired region. In relation to this, an environmental change due to an osmotic pressure, an environmental change due to a change in ionic concentration, providing of a moist environment, and a change in a pH level may be implemented in accordance with a direction in which the substance is diffused.

Figure 23:
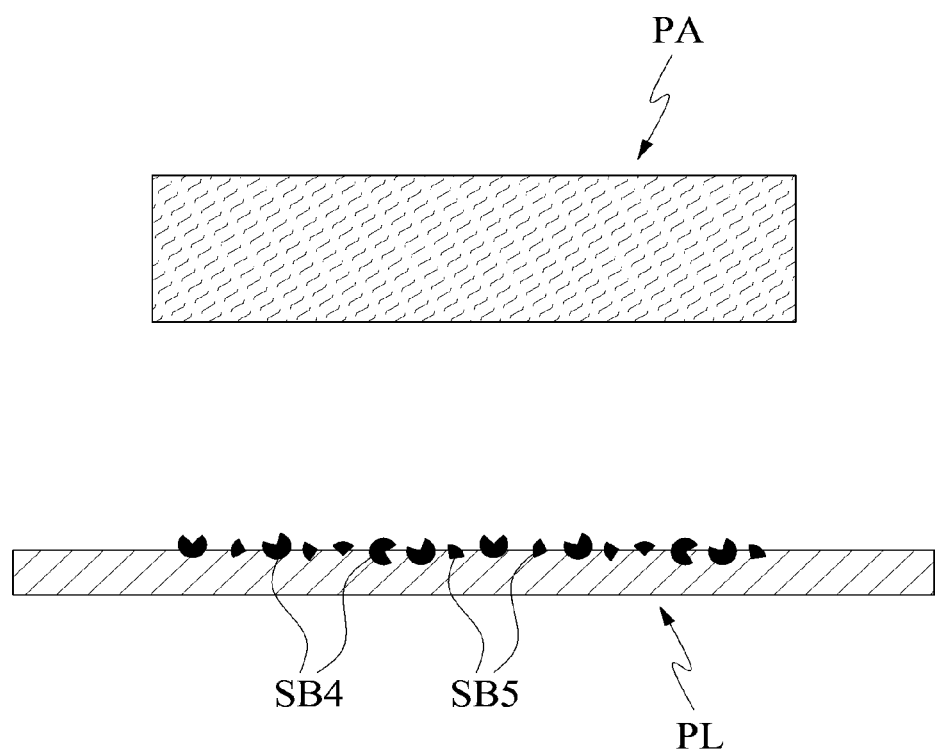
FIG. 23 illustrates providing of an environment as an example of a function of a patch according to the present application.
Figure 24:
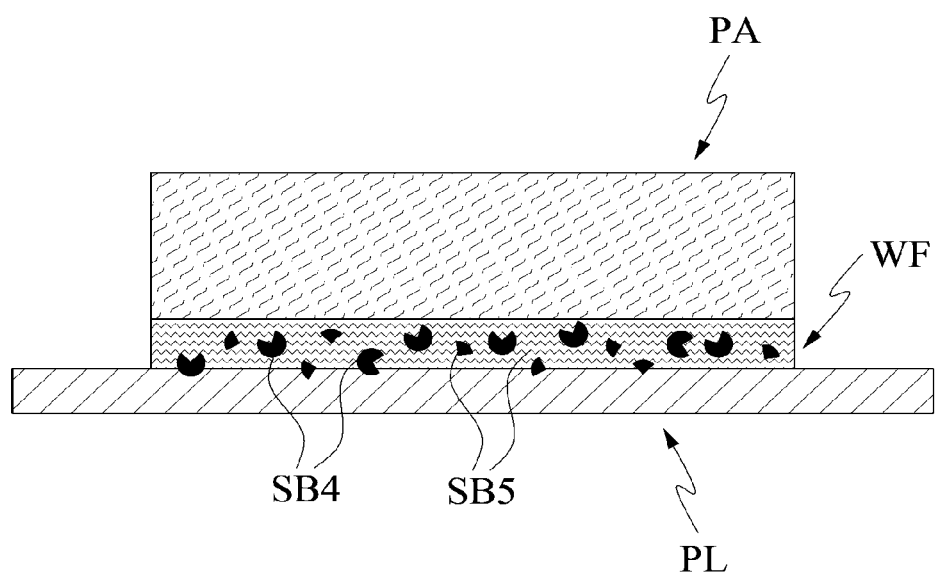
FIG. 24 illustrates providing of an environment as an example of a function of a patch according to the present application.
Figure 25:
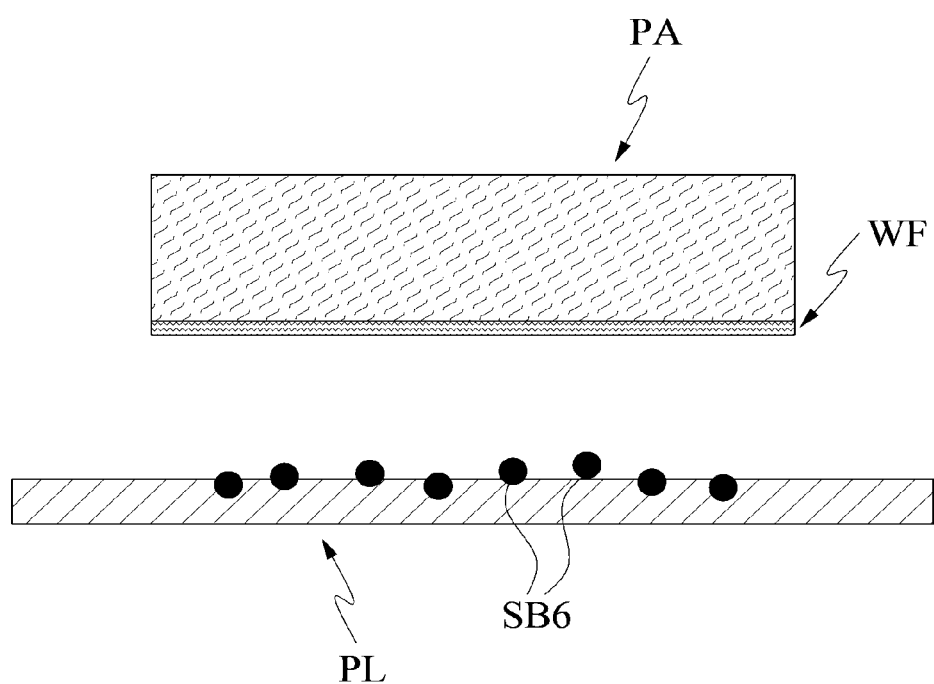
FIG. 25 illustrates providing of an environment as an example of a function of a patch according to the present application.

FIGS. 23 to 25 illustrate providing of a predetermined environment to an external plate PL by the patch PA as an example of providing of an environment among the functions of the patch PA according to the present application. According to FIGS. 23 to 25, the patch PA may provide a predetermined environment to an external plate PL on which a fourth substance SB4 and a fifth substance SB5 are placed. For example, the patch PA may provide a predetermined environment to the plate PL for the fourth substance SB4 and the fifth substance SB5 to react and form a sixth substance SB6. The providing of the environment may be performed by the patch PA coming into contact with the plate PL so that a water film WF is formed in the vicinity of a contact region and the fourth substance SB4 and the fifth substance SB5 are captured in the water film WF.

3. Application of Patch

The patch PA according to the present application may be implemented to perform various functions by suitably applying the above-described functions of the patch PA.

The technical spirit of the present application will be described below by disclosing some embodiments. However, the technical scope to which functions of the patch PA disclosed by the present application are applied may be interpreted in a broad sense within the scope that may be easily derived by those of ordinary skill in the art, and the scope of the present application should not be interpreted as being limited by the embodiments disclosed herein.

3.1. In-Patch

The patch PA may provide a reaction region for a substance. In other words, a reaction of a substance may occur in at least a portion of a spatial region affected by the patch PA. In this case, the reaction of a substance may be a reaction between liquid substances SB captured in the patch PA and/or a reaction between the captured liquid substance SB and a substance provided from the outside of the patch PA. The providing of a reaction region for a substance may activate or promote a reaction of a substance.

In this case, the liquid substance SB captured in the patch PA may include at least one of a substance added upon manufacturing the patch PA, a substance additive into the patch PA after the manufacturing of the patch PA and contained in the patch PA, and a substance temporarily captured in the patch PA. In other words, regardless of a form in which a substance is captured in the patch PA, any substance captured in the patch PA at a time point at which a reaction in the patch PA is activated may react in the patch PA. Further, a substance injected after the manufacturing of the patch PA may also act as a reaction initiator.

The providing of a reaction region for a reaction related to the liquid substance SB captured in the patch PA may be a concept subordinate, in terms of embodiment, to the above-described Section 2.1.3 (that is, providing of reaction space). Alternatively, the providing of a reaction region for a reaction related to the liquid substance SB captured in the patch PA may consist of multiple concepts that perform combined functions of the above-described Section 2.1.3 and Section 2.2.4.2 (that is, absorption). The providing of a reaction region for a reaction related to the liquid substance SB captured in the patch PA is not limited thereto and may be implemented in the form in which two or more functions are combined.

3.1.1 First Embodiment

Hereinafter, description will be given by assuming that the function of absorption into the patch PA and the function of providing of a reaction space (hereinafter referred to as "providing function") are performed by a single patch PA. In this case, the absorption function and the providing function may be simultaneously-performed functions, functions performed at different time points, or functions sequentially performed to perform another function. The patch PA further including other functions in addition to the absorption and providing functions may also be considered as belonging to the present embodiment.

As described above, the patch PA may perform a function of capturing a substance, and the substance may have fluidity even when the substance is captured. When some components of the liquid substance SB are non-uniformly distributed, the non-uniform components may be diffused. Even when components of the liquid substance SB are uniformly distributed, the liquid substance SB may have a predetermined level of mobility due to irregular motion of particles. In this case, a reaction between substances, for example, specific binding between substances, may occur inside the patch PA.

For example, in the patch PA, in addition to a reaction between captured substances, a reaction in a form in which a substance having fluidity that is newly captured in the patch PA and the substance that has been captured in the patch PA bind specifically to each other may also be possible.

The reaction between the substance having fluidity and the substance that has been captured in the patch PA may also occur after the substance patch being separated from a space that has been provided. For example, after the patch PA absorbs the substance having fluidity from an arbitrary space, the patch PA may be separated from the arbitrary space, and a reaction between the absorbed substance and the substance that has been captured in the patch PA may occur in the patch PA.

In addition, the patch PA may allow a reaction of a substance captured therein to occur by performing the absorption function with respect to a substance having fluidity. In other words, the absorption of the substance having fluidity by the patch PA may act as a trigger for a reaction between the absorbed substance and the substance that has been captured in the patch PA. The reaction may occur inside a space defined by the patch PA.

A composition of the liquid substance SB captured in the patch PA may be changed due to the reaction occurring inside the patch PA. When, particularly, a substance captured inside the patch PA is a compound, a chemical composition thereof may be changed before and after a reaction. Alternatively, a composition distribution of a substance may be changed in accordance with a position of the substance in the patch PA. For example, this may be due to diffusion or particles having an attractive force specific to another substance.

When the composition of the liquid substance SB is changed due to a reaction inside the patch PA, a portion of the substance may be absorbed into the patch PA due to a concentration difference between the patch PA and a substance outside the patch PA (when a substance in contact with the patch PA is present, the corresponding substance), or the substance may be released from the patch PA to the substance outside the patch PA.

3.1.2 Second Embodiment

Hereinafter, an embodiment in which the containing function of the patch PA and the function of providing of a reaction space for a substance are performed together for at least a predetermined amount of time will be described. More specifically, the patch PA may perform a function of providing a space for at least a portion of the liquid substance SB contained in the patch PA to react.

The patch PA may contain a substance and provide a reaction space for the contained substance. In this case, the reaction space provided by the patch PA may be the microcavities formed by the mesh structural body NS of the patch PA or a surface region of the patch PA. Particularly, when a substance contained in the patch PA and a substance applied on a surface of the patch PA react, the reaction space may be the surface region of the patch PA.

The reaction space provided by the patch PA may serve to provide a specific environmental condition. While a reaction occurs in the liquid substance SB placed in the patch PA, an environmental condition of the reaction may be adjusted by the patch PA. For example, the patch PA may serve as a buffer solution.

By containing a substance through a mesh structure, the patch PA does not require a container, separately. When the reaction space of the patch PA is a surface of the patch PA, a reaction may be easily observed through the surface of the patch PA. For this, the shape of the patch PA may be deformed into a shape that facilitates the observation.

The liquid substance SB contained in the patch PA may be denaturalized or react with a different type of substance. The composition of the liquid substance SB contained in the patch PA may be changed with time.

The reaction may refer to a chemical reaction in which a chemical formula is changed, a physical state change, or a biological reaction. In this case, the liquid substance SB contained in the patch PA may be a substance formed of a single component or a mixture including a plurality of components.

3.2 Providing of Movement Path (Channeling)

Hereinafter, the patch PA that performs a function of providing a substance movement path will be described. More specifically, as described above, the patch PA may capture, absorb, release, and/or contain a substance having fluidity. Various embodiments of the patch PA that performs the function of providing a substance movement path may be implemented by each of the above-described functions of the patch PA or a combination thereof. However, a few embodiments will be disclosed for a better understanding.

3.2.1 Third Embodiment

The patch PA may be implemented to perform functions described in Section 2.2.4.1 (that is, the section related to delivery) and Section 2.2.4.2 (that is, the section related to absorption) among the above-described functions of the patch PA. In this case, the absorption function and the delivery function may be provided together or sequentially provided.

The patch PA may perform the absorption and delivery functions together to provide a substance movement path. Particularly, the patch PA may absorb an external substance and provide the absorbed external substance to an external region, thereby providing a movement path to the external substance.

The providing of the movement path of the external substance by the patch PA may be performed by absorbing the external substance and releasing the external substance. More specifically, the patch PA may come into contact with the external substance, absorb the external substance, come into contact with the external region, and deliver the external substance to the external region. In this case, the capturing of the external substance and the delivery of the captured external substance to the external region by the patch PA may be performed through a process similar to those of the above-described absorption and delivery.

The external substance absorbed into the patch PA and provided may be in a liquid phase or a solid phase.

In this way, the patch PA may allow a portion of the external substance to be provided to another external substance. The external substance and the other external substance may simultaneously come into contact with the patch PA. The external substance and the other external substance may come into contact with the patch PA at different time points.

The external substance and the other external substance may come into contact with the patch PA at different time points. When the external substances come into contact with the patch PA at different time points, the external substance may come into contact with the patch PA first, and after the external substance and the patch PA are separated, the patch PA and the other external substance may come into contact. In this case, the patch PA may temporarily contain a substance captured from the external substance.

The patch PA may simultaneously provide a substance movement path and additionally provide a time delay. The patch PA may perform a function of suitably adjusting an amount of substance provided to another external substance and a speed of such providing.

Such a series of processes may be carried out in one direction with respect to the patch PA. As a specific example, absorption of a substance may be performed through a surface of the patch PA, an environment may be provided in an inner space of the patch PA, and the substance may be released through another surface facing the surface.

3.2.2 Fourth Embodiment

The patch PA may perform the absorbing and releasing of a substance among the above-described functions of the patch PA and the providing of a reaction space for the substance simultaneously. In this case, the absorption and release of the substance and the providing of the reaction space may be performed simultaneously or sequentially.

According to an embodiment, in performing the processes of absorbing and releasing an external substance, the patch PA may provide a reaction space to the absorbed external substance for at least a predetermined amount of time. The patch PA may provide a specific environment for at least some time to the liquid substance SB captured in the patch PA, including the absorbed external substance.

The liquid substance SB that has been captured in the patch PA and the external substance captured in the patch PA may react inside the patch PA. The external substance absorbed into the patch PA may be affected by an environment provided by the patch PA. The substance released from the patch PA may include at least a portion of a substance generated through the reaction. The external substance may be released from the patch PA after the composition, characteristics, and the like of the external substance are changed.

The absorbed substance may be released from the patch PA. The external substance being absorbed into the patch PA and being released from the patch PA may be understood as the external substance passing through the patch PA. The external substance that has passed through the patch PA may lose integrity due to a reaction inside the patch PA or an influence of an environment provided by the patch PA.

The above-described processes of absorption of an external substance, reaction of a substance, and providing of the substance may be carried out in one direction. In other words, the absorption of a substance may be performed at one position of the patch PA, the providing of an environment may be performed at another position of the patch PA, and the release of the substance may be performed at yet another position of the patch PA.

Figure 26:
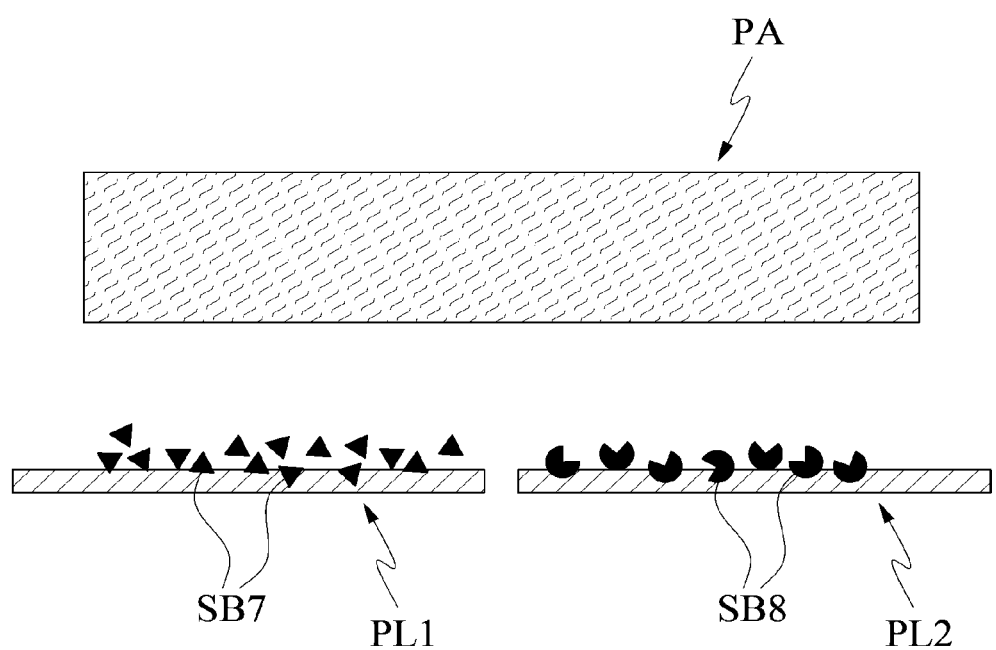
FIG. 26 illustrates performance of absorbing and providing of a substance as an embodiment of a patch according to the present application.
Figure 27:
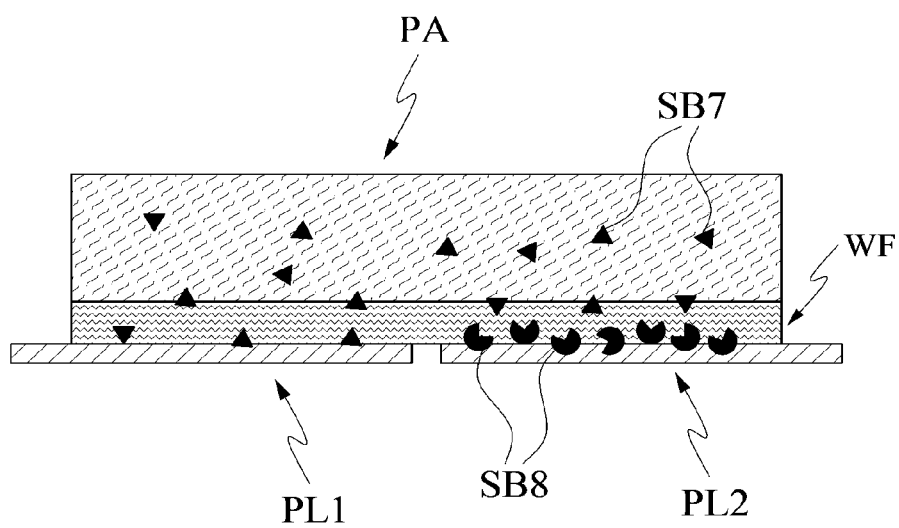
FIG. 27 illustrates performance of absorbing and providing of a substance as an embodiment of a patch according to the present application.
Figure 28:
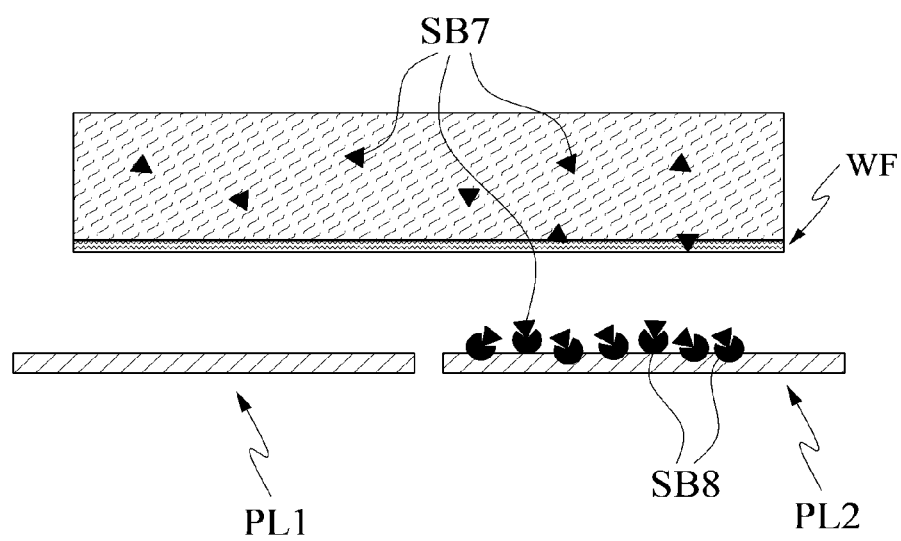
FIG. 28 illustrates performance of absorbing and providing of a substance as an embodiment of a patch according to the present application.

FIGS. 26 to 28 illustrate providing of a substance movement path between two plates PL as an embodiment of the patch PA according to the present application. According to FIGS. 26 to 28, the patch PA may provide a substance movement path between a plate PL1 on which a seventh substance SB7 is applied and a plate PL2 on which an eighth substance SB8 is applied. As a specific example, when the seventh substance SB7 is capable of binding to the eighth substance, and the eighth substance is fixed to the plate PL2, the patch PA may come into contact with the plates PL1 and PL2 so that the seventh substance SB7 is moved through the patch PA and bound to the eighth substance SB8. The seventh substance SB7 and the eighth substance SB8 may be connected to the patch PA through a water film WF formed by the patch PA coming into contact with the plates PL1 and PL2.

Figure 29:
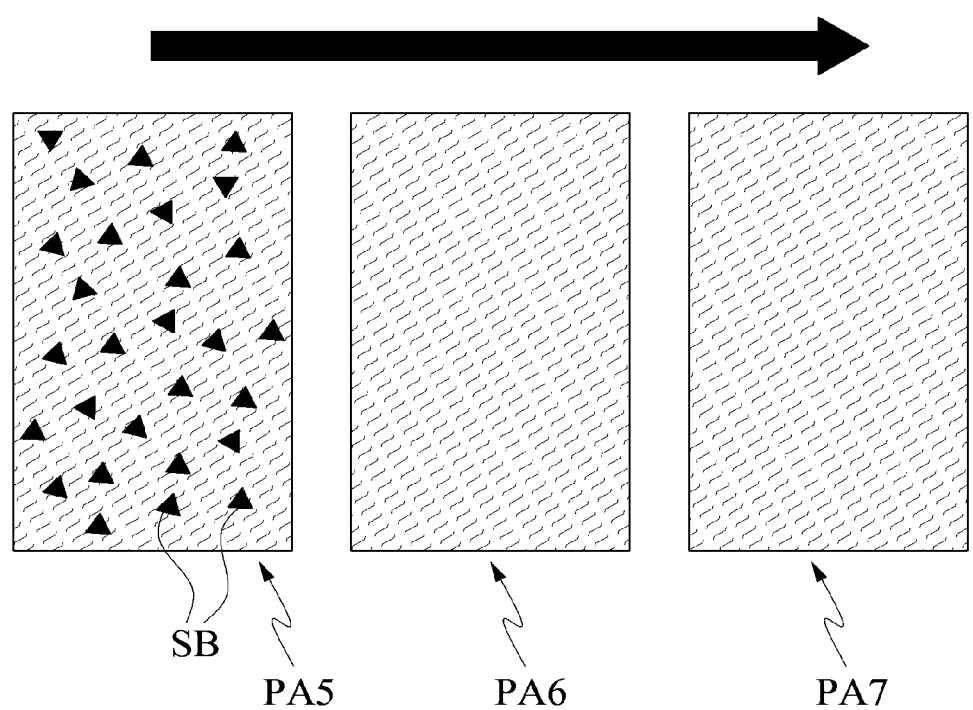
FIG. 29 illustrates performance of absorbing and providing of a substance as an embodiment of a patch according to the present application.
Figure 30:
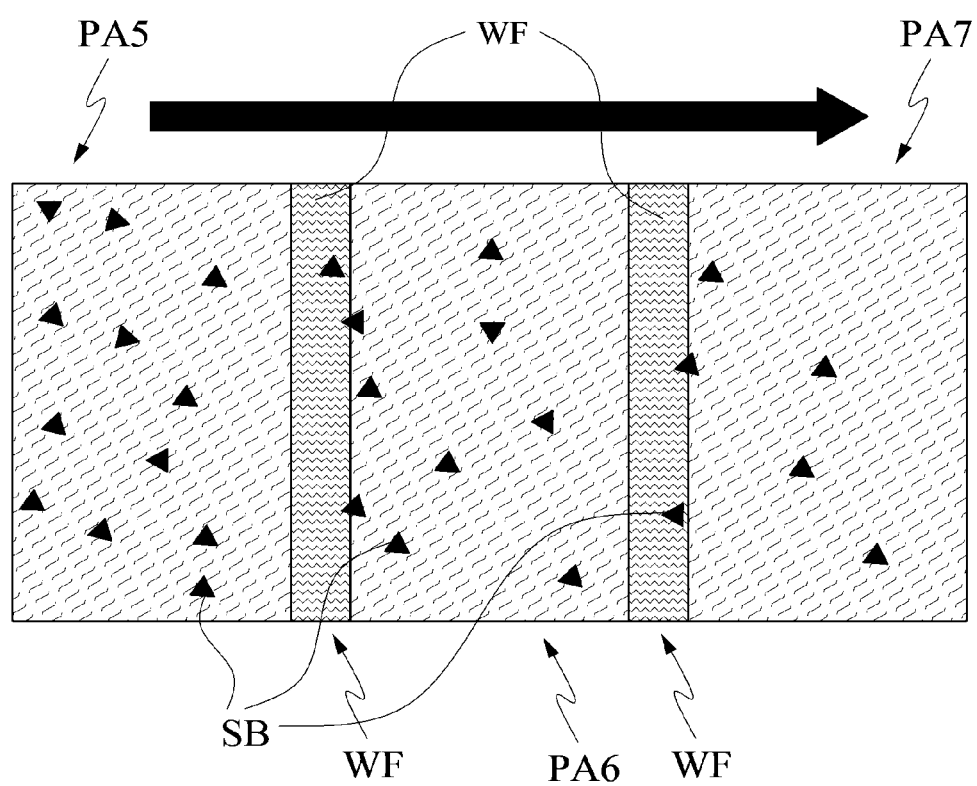
FIG. 30 illustrates performance of absorbing and providing of a substance as an embodiment of a patch according to the present application.

FIGS. 29 and 30 illustrate providing of a substance movement path between two patches as an embodiment of the patch PA according to the present application. According to FIGS. 29 and 30, a patch PA6 configured to provide the movement path may be in contact with a patch PA5 configured to contain a substance to be moved, and a patch PA7 configured to receive the substance to be moved. The patch PA6 configured to provide the movement path may come into contact with the patch PA5 configured to contain the substance to be moved and the patch PA7 configured to receive the substance to be moved, and the substance to be moved may be moved to the patch PA7 configured to receive the substance to be moved. The movement of the substance between the patches may be performed by a water film WF formed in the vicinity of a contact region between the patches.

Figure 31:
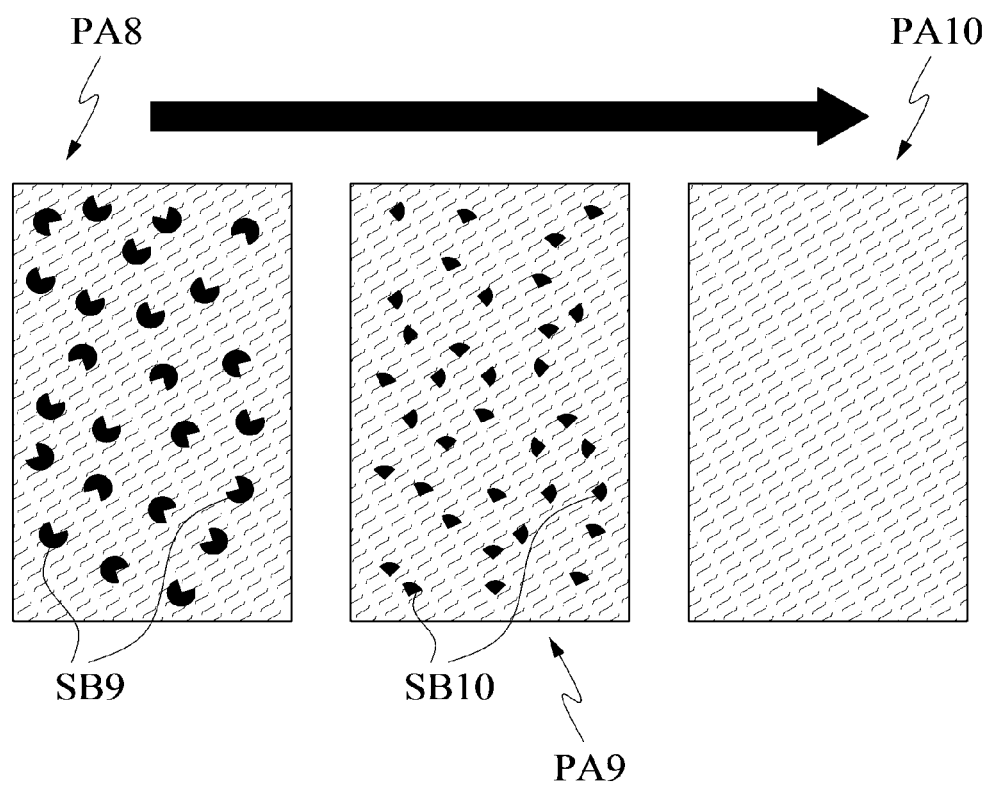
FIG. 31 illustrates performance of absorbing and providing of a substance and providing of an environment as an embodiment of a patch according to the present application.
Figure 32:
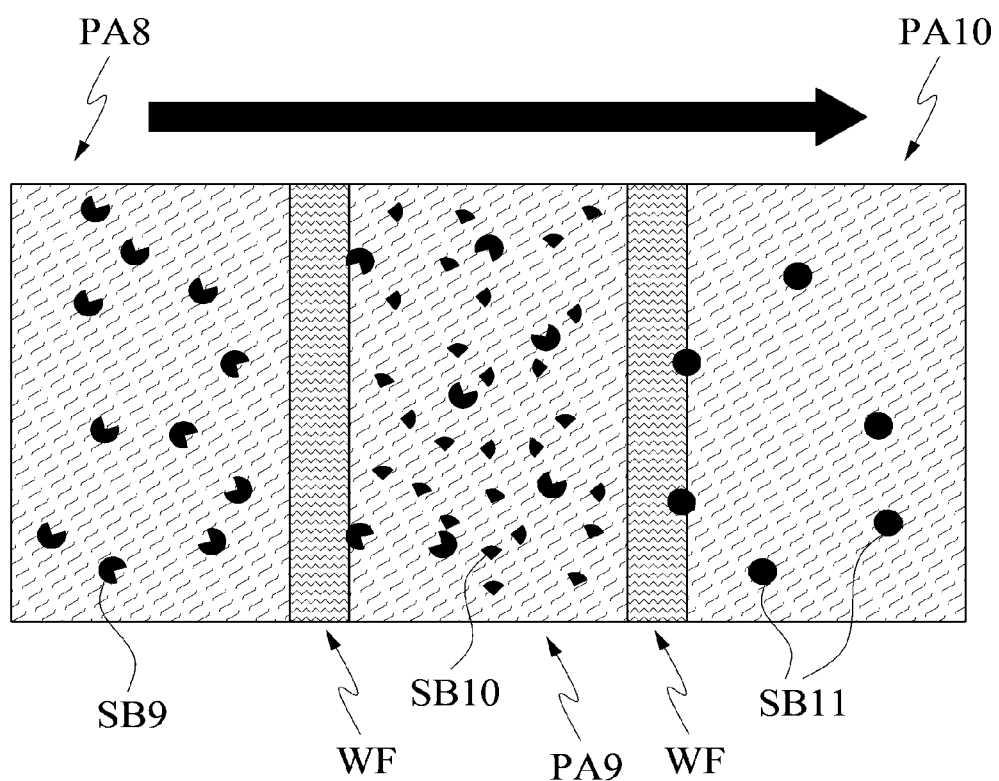
FIG. 32 illustrates performance of absorbing and providing of a substance and providing of an environment as an embodiment of a patch according to the present application.

FIGS. 31 and 32 illustrate providing of a substance movement path between two patches as an embodiment of the patch according to the present application. According to FIGS. 29 and 30, a patch PA9 configured to provide the movement path may be in contact with a patch PA8 configured to contain a ninth substance SB9 and a patch PA10 configured to receive a substance. The patch PA9 providing the movement path may come into contact with the patch PA8 configured to contain the ninth substance SB9 to absorb the ninth substance SB9. The absorbed ninth substance SB9 may react with a tenth substance SB10 contained in the patch PA9, which is configured to provide the movement path, and generate an eleventh substance. An eleventh substance SB11 may be provided from the patch PA9 configured to provide the movement path to the patch PA10 configured to receive the substance. The movement of a substance between the patches PA may be performed through a water film WF formed in the vicinity of a contact region between the patches PA.

3.3 Multi-Patch

A patch PA may be solely used, or a plurality of patches PA may be used together. In this case, the plurality of patches PA being able to be used together includes a case in which the plurality of patches PA are sequentially used as well as a case in which the plurality of patches PA are used simultaneously.

When the plurality of patches PA are used simultaneously, the patches PA may perform different functions. Although each patch PA of the plurality of patches PA may contain the same substance, the plurality of patches PA may also contain different substances.

When the plurality of patches PA are used simultaneously, the patches PA may not come into contact with each other such that substance movement does not occur between the patches PA, or a desired function may be performed in a state in which substances contained in the patches PA are exchangeable.

Although the plurality of patches PA used together may be manufactured in shapes similar to each other or in the same size, the plurality of patches PA may be used together even when the plurality of patches PA have different shapes. Each patch PA constituting the plurality of patches PA may be manufactured such that densities of the mesh structural bodies NS are different or components constituting the mesh structural bodies NS are different.

3.3.1 Contact with Plurality of Patches

When a plurality of patches PA are used, the plurality of patches PA may come into contact with a single target region TA. The plurality of patches PA may come into contact with the single target region TA and perform a desired function.

When a plurality of target regions TA are present, the plurality of patches PA may come into contact with different target regions TA. When the plurality of target regions TA are present, the plurality of patches PA may respectively come into contact with corresponding target regions TA and perform a desired function.

The plurality of patches PA may come into contact with a substance applied on the target region TA. In this case, the substance applied on the target region TA may be fixed or have fluidity.

The desired function may be a function of providing or absorbing the substance. However, each patch PA does not necessarily provide the same substance or absorb the same substance, and the patches PA may provide different substances to the target region TA or absorb different components from a substance placed in the target region TA.

The desired function may be different for each patch PA constituting the plurality of patches PA. For example, one patch PA may perform the function of providing a substance to the target region TA, and another patch PA may perform the function of absorbing the substance from the target region TA.

The plurality of patches PA may include different substances, and the different substances may be provided to a single target region TA and used to induce a desired reaction. When a plurality of components of a substance is required for the desired reaction to occur, the plurality of components may be contained in a plurality of patches PA respectively and provided to the target region TA. Such use of the plurality of patches PA may be particularly useful when properties of substances required for a desired reaction are lost or altered when the substances required for the reaction being mixed for reasons such as being contained in a single patch PA.

According to an embodiment, when the plurality of patches PA include substances formed of different components, and the substances formed of different components have different specific binding relationships, the substances formed of different components may be provided to the target region TA. The plurality of patches PA may be used to detect a plurality of specific bindings from the substances applied on the target region TA, by providing the substances including different components.

According to another embodiment, the plurality of patches PA may include substances formed of the same component, but each patch PA may have a different concentration with respect to the substance formed of the same component. The plurality of patches PA including the substances formed of the same component may come into contact with the target region TA and be used to determine an influence in accordance with a concentration of the substance included in the plurality of patches PA.

When the plurality of patches PA are used as described above, the patches PA may be grouped into more efficient forms and used. In other words, the configuration of the plurality of patches PA being used may be changed every time the plurality of patches PA are used. The plurality of patches PA may be manufactured in the form of a cartridge and used. In this case, the form of each patch PA being used may be suitably standardized and manufactured.

The plurality of patches PA in the form of a cartridge may be suitable when patches PA configured to contain a plurality of types of substances are manufactured to be used by being chosen as necessary.

Particularly, when attempting to detect a specific reaction of each substance from the target region TA using a plurality of types of substances, a combination of specific reactions to be detected may be changed every time the detection is performed.

Figure 33:
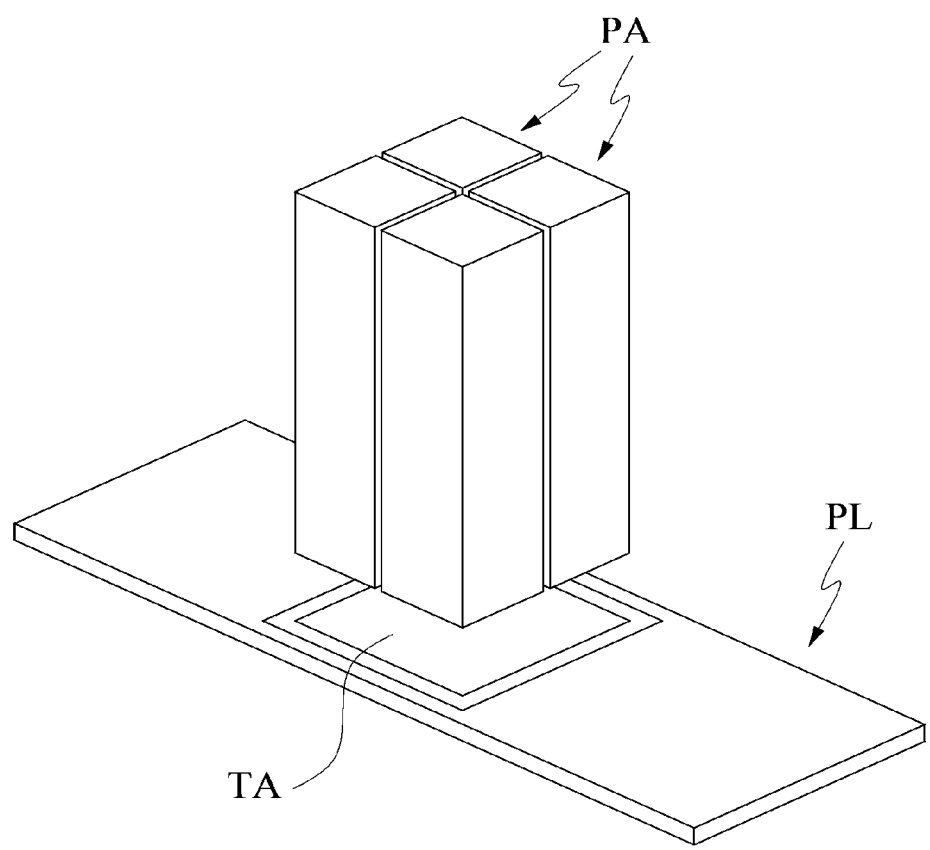
FIG. 33 illustrates an implementation of a plurality of patches as an embodiment of a patch according to the present application.

FIG. 33 illustrates a case in which the plurality of patches PA are used together as an embodiment of the patch PA according to the present application. According to FIG. 33, the plurality of patches PA according to an embodiment of the present application may simultaneously come into contact with a target region TA placed on a plate PL. The patches PA constituting the plurality of patches PA may have a standardized form. The plurality of patches PA may include a first patch and a second patch, and a substance contained in the first patch may be different from a substance contained in the second patch.

Figure 34:
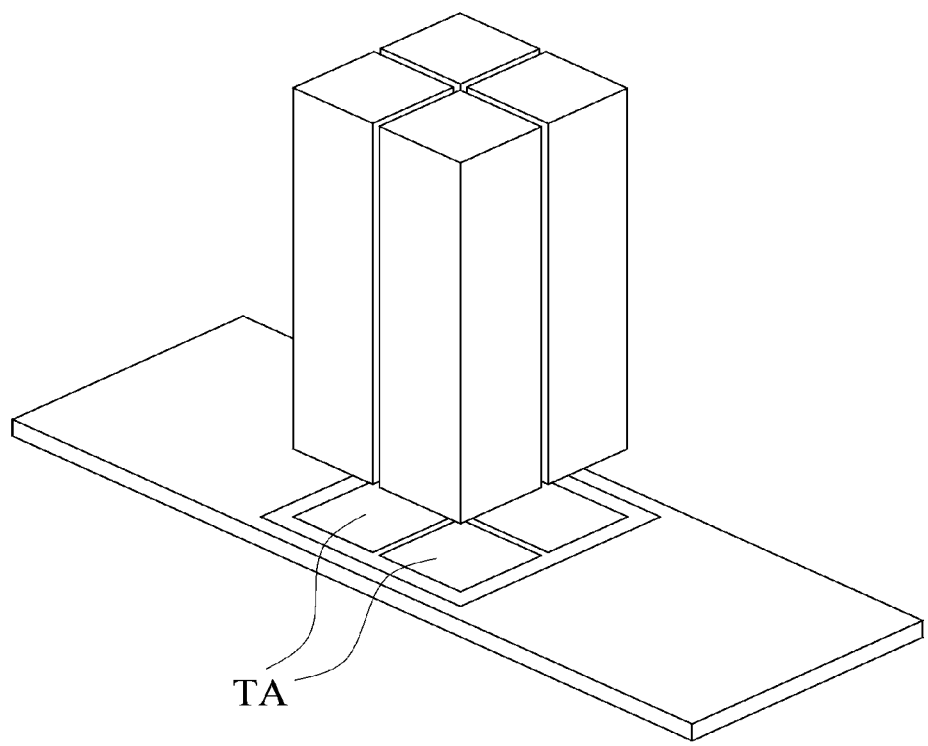
FIG. 34 illustrates an implementation of a plurality of patches and a plate having a plurality of target regions as an embodiment of a patch according to the present application.

FIG. 34 illustrates a case in which the plurality of patches PA are used and the plate PL includes a plurality of target regions TA. According to FIG. 34, the plurality of patches PA according to an embodiment of the present application may simultaneously come into contact with the plurality of target regions TA placed on the plate PL. The plurality of patches PA may include a first patch PA and a second patch PA, the plurality of target regions TA may include a first target region and a second target region, and the first patch may come into contact with the first target region and the second patch may come into contact with the second target region.

3.3.2 Fifth Embodiment

The plurality of patches PA may perform a plurality of functions. As described above, the patches PA may simultaneously perform a plurality of functions, and the patches PA may also simultaneously perform different functions. However, embodiments are not limited to the above, and the functions may also be combined and performed in the plurality of patches PA.

First, in the case in which the patches PA simultaneously perform the plurality of functions, the patches PA may perform both containing and release of a substance. For example, the patches PA may contain different substances and release substances contained in the target regions TA. In this case, the contained substances may be simultaneously or sequentially released.

Next, in the case in which the patches PA simultaneously perform different functions, the patches PA may separately perform containing and release of a substance. In this case, only some of the patches PA may come into contact with a target region TA and release a substance to the target region TA.

3.3.3 Sixth Embodiment

When a plurality of patches PA are used, as described above, the plurality of patches PA may perform a plurality of functions. First, the patches PA may simultaneously perform containing, releasing, and absorbing of substances. Alternatively, the patches PA may also separately perform the containing, releasing, and absorbing of the substances. However, embodiments are not limited thereto, and the functions may also be combined and performed in the plurality of patches PA.

For example, at least some of the plurality of patches PA may contain a substance and release the contained substance to the target region TA. In this case, at least a remainder of the plurality of patches PA may absorb a substance from the target region TA. Some of the plurality of patches PA may release a substance that binds specifically to a substance placed in the target region TA. In this case, specific binding may be detected by absorption of a substance that has not formed specific binding from the substance placed in the target region TA using another patch PA.

3.3.4 Seventh Embodiment

When a plurality of patches PA are used, the patches PA may simultaneously perform containing and release of a substance and providing of an environment. Alternatively, the patches PA may separately perform the containing and release of a substance and providing of an environment. However, embodiments are not limited thereto, and the functions may also be performed in combination in the plurality of patches PA.

For example, a patch PA among the plurality of patches PA may release a substance contained therein to the target region TA. In this case, another patch PA may provide an environment to the target region TA. Here, the providing of an environment may be implemented in the form in which an environmental condition of a substance contained in the other patch PA is provided to the target region TA. More specifically, a reacting substance may be provided to the target region TA by the patch PA, and the other patch PA may come into contact with the target region TA and provide a buffering environment.

As another example, the plurality of patches PA may be in contact with each other. In this case, at least one patch PA may contain a substance and release the substance contained therein to another patch PA configured to provide an environment. In the present embodiment, the patch PA configured to provide an environment may release a substance, come into contact with at least one other patch PA that is not in contact with the patch PA configured to provide an environment, and absorb a substance from the patch PA.

4. Culture

4.1 Culturing Patch

The patch PA of the present application may be used in culturing an object to be cultured.

The object to be cultured may include microorganisms such as bacteria and cells separated from human beings or animals. Alternatively, the object to be cultured may include laboratory cells, primary cultured cells, tissues, organs, and the like.

The object to be cultured is not limited to the above-listed examples and may be any biological substance capable of growing by receiving a required nutrient component from a culturing patch of the present application which will be described below.

However, for convenience of description, description will be given below by assuming that object to be cultured is bacteria. However, it should be noted that the scope of the present disclosure is not limited thereby.

Generally, bacterial culture is performed to process staining or diagnostic tests such as a drug test on bacteria present in a sample SA collected from a patient. Since an amount of bacteria present in the sample may not be sufficient to perform a diagnostic test, the amount of bacteria is increased through bacterial culture.

A culturing patch PA may contain a required nutrient component required for culture of bacteria. The required nutrient component may be properly changed in accordance with a type of an object to be cultured. For example, when it is desired to culture specific bacteria, the required nutrient component may be formed of components required for culturing the specific bacteria. As another example, when it is desired to culture nonspecific bacteria, various required nutrient components may be contained in the patch PA.

In addition to the required nutrient component, the culturing patch PA may contain a buffer solution. The buffer solution may be a solution that satisfies an environmental condition required for growth of the culture. For example, the buffer solution may adjust acidity, an osmotic pressure, or the like.

To sum up, the culturing patch PA may be interpreted as containing culture media.

4.2 Culturing Method

A culturing method using the above-described culturing patch PA will be described below.

In the present application, a culturing method uses a culturing patch PA and a plate PL. The plate PL may be a petri dish that is conventionally used in organism culture, a slide glass, or the like.

It will be assumed that object to be cultured is cultured on a slide glass in the description below and the drawings. However, such an assumption is merely for convenience of description, and the plate PL for culturing is not limited to a slide glass.

Figure 35:
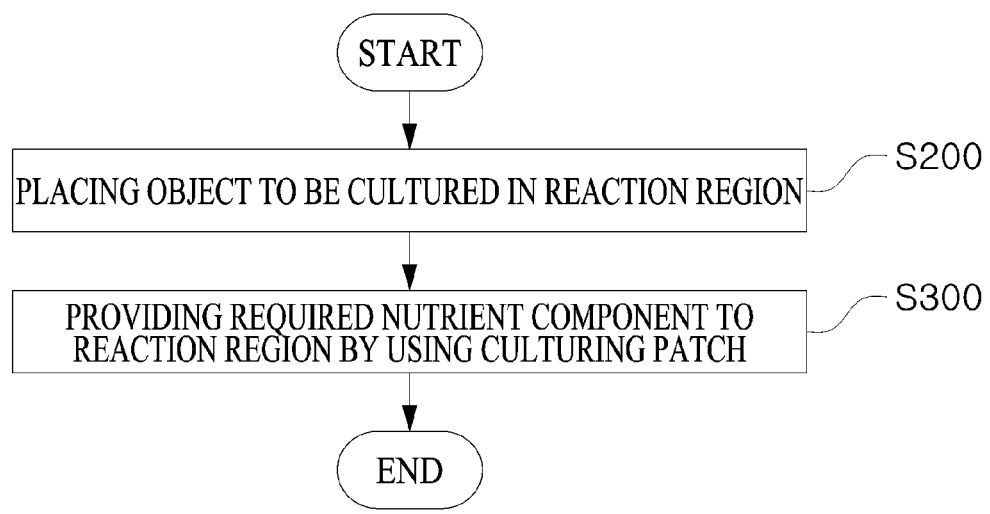
FIG. 35 is a flowchart related to an embodiment of a culturing method according to the present application.

FIG. 35 is a flowchart related to an embodiment of a culturing method according to the present application.

Referring to FIG. 35, an embodiment of a culturing method according to the present application may include placing object to be cultured in a reaction region (S200) and providing a required nutrient component to the reaction region by using a culturing patch PA (S300).

4.2.1 Preparation of Object to be Cultured

Preparation of an object to be cultured will be described.
Object to be cultured, i.e., bacteria BAC, may be prepared on a plate PL.

The plate PL may refer to a general slide glass or a solid plate such as a plate manufactured with polystyrene, polypropylene or the like. A form of a bottom or transparency of the plate PL may be different in accordance with a detection method. The plate PL may include a reaction region which comes into contact with the patch PA or in which a desired reaction may occur.

Figure 36:
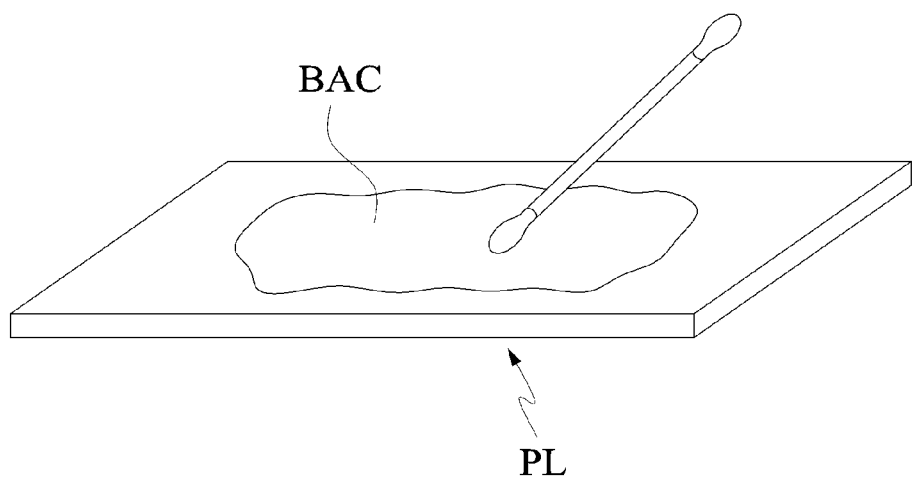
FIG. 36 is a view illustrating application of an object to be cultured according to the present application.

FIG. 36 is a view illustrating application of an object to be cultured according to the present application.

Bacteria BAC may be applied on a reaction region of a plate PL (S200). The application may be performed by various methods. According to an example, the application of the bacteria BAC may be performed using an applicator such as a swab. Specifically, an operator may collect bacteria BAC from a testee or the like by using an applicator and rub the applicator on a reaction region of a plate PL to place the collected bacteria BAC on the plate PL. Of course, the collection and application of an object to be cultured such as bacteria are not necessarily limited to the above-described example, and an object to be cultured may be applied on the reaction region on the plate PL through various conventional methods generally used for collection and application of bacteria or cells.

Instead of culturing cells or bacteria released from a biological tissue, culturing tissue is also possible. When a tissue is cultured, for preparation of an object to be cultured, a section of tissue in the form of a thin film may be collected from the tissue, and then the section of tissue may be placed in a reaction region on the plate PL.

4.2.2 Culture of an Object to be Cultured

A required nutrient component may be provided to a reaction region by using a culturing patch PA (S300).

When an object to be cultured is applied on the reaction region, the culturing patch PA may provide the required nutrient component to the reaction region, and accordingly, the object to be cultured may grow by receiving the required nutrient component.

Figure 37:
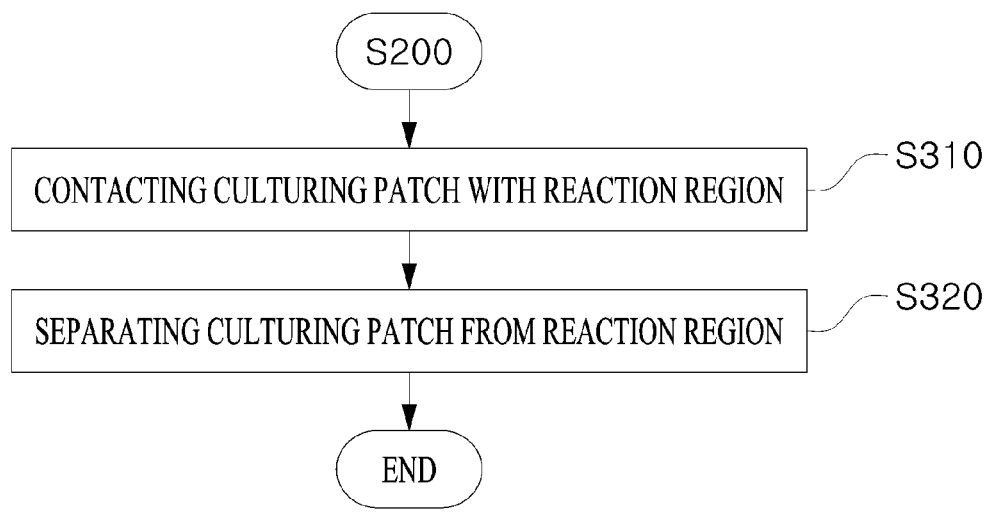
FIG. 37 is a flowchart of delivering a required nutrient component by using a culturing patch in an embodiment of a culturing method according to the present application.

FIG. 37 is a flowchart of the providing of the required nutrient component by using the culturing patch in the embodiment of the culturing method according to the present application.

Referring to FIG. 37, the providing of the required nutrient component to the reaction region by using the culturing patch PA (S300) may include contacting the culturing patch PA with the reaction region (S310) and separating the culturing patch from the reaction region (S320).

Figure 38:
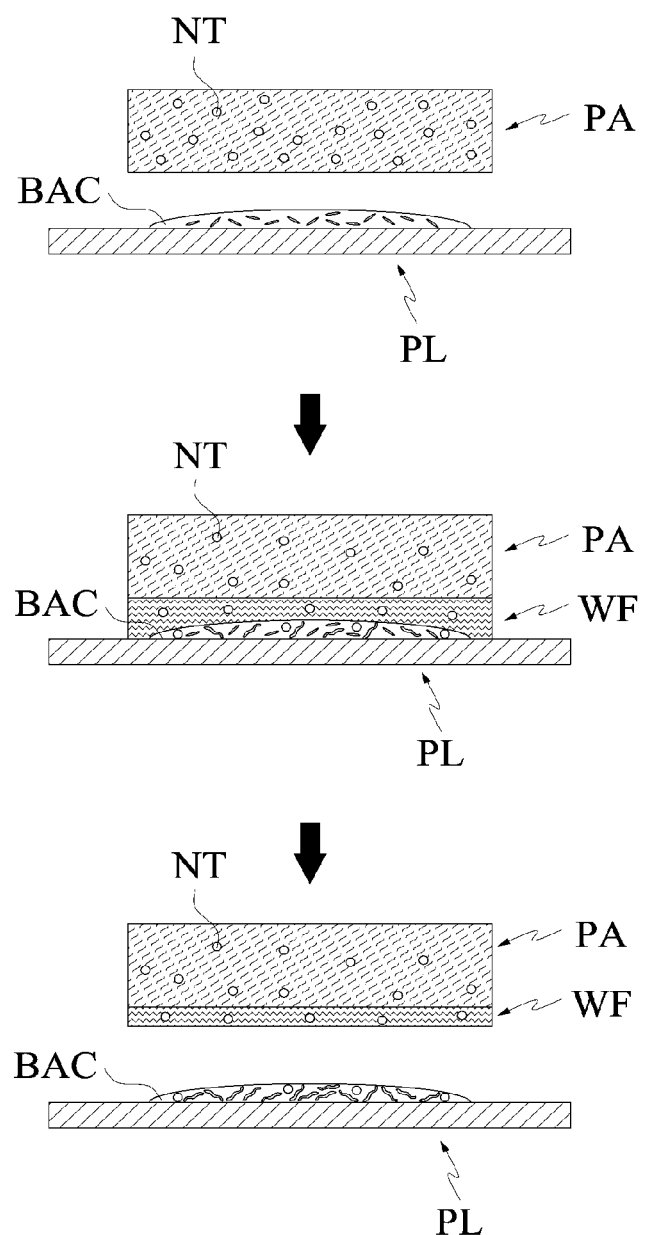
FIG. 38 is an operational view of the culturing method according to FIG. 36.

FIG. 38 is an operational view of the culturing method according to FIG. 36.

Referring to FIG. 38, the culturing patch PA may be brought into contact with the reaction region (S310). When the culturing patch PA comes into contact with the reaction region, a water film WF may be formed between the culturing patch PA and the plate PL. The required nutrient component contained in the culturing patch PA may be provided from the culturing patch PA to the reaction region through the water film WF. The object to be cultured may grow by receiving the required nutrient component provided to the reaction region.

Referring again to FIG. 38, when the growth of the object to be cultured has been sufficiently performed, the culturing patch PA may be separated from the reaction region (S320). When the culturing patch PA is separated from the reaction region, the providing of the required nutrient component from the culturing patch PA to the reaction region through the water film WF is stopped. When the providing of the required nutrient component is stopped, the growth of the object to be cultured may be stopped. Therefore, the growth of the objects to be cultured may be controlled by separating the culturing patch PA from the reaction region.

The water film WF may be absorbed into the patch PA in a process in which the culturing patch PA is separated from the reaction region, and the required nutrient component present in the water film WF may be absorbed into the patch PA along with the water film WF.

In the process in which the water film WF is absorbed due to the process in which the culturing patch PA is separated, there is some possibility that the objects to be cultured may also be absorbed into the culturing patch PA or be moved toward a contact surface between the culturing patch PA and the reaction region. The object to be cultured may not be absorbed into the culturing patch PA in accordance with various characteristics of the object to be cultured such as the type or size thereof. To prevent the object to be cultured from being absorbed into the culturing patch PA in the process in which the culturing patch PA is separated, the object to be cultured may be fixated on the plate PL before the culturing patch PA comes into contact therewith.

The fixation may be performed using various fixing agents. Any substance capable of fixing the object to be cultured on the plate PL without interfering with the growth of the object to be cultured or killing the object to be cultured may be selected as the fixation agent.

The fixation agent in the form of a solution may be sprayed onto the reaction region on the plate PL. Alternatively, in the present application, the object to be cultured may be fixed on the plate PL by contacting a fixation patch PA containing a fixation agent with the reaction region and separating the fixation patch PA therefrom so that the fixation agent is provided to the reaction region before the culturing patch PA is brought into contact with the reaction region.

When a hydrophobic substance such as an alcohol including ethanol or methanol and formaldehyde is used as a fixation solution, the patch PA containing the fixation solution may be prepared to have a hydrophobic property. Materials of the hydrophobic patch PA include a polydimethylsiloxane (PDMS) gel, a polymethyl methacrylate (PMMA) gel, a silicone gel, or the like.

Alternatively, to fix the object to be cultured, a solid substance which is formed by solidifying a fixation agent may also be used instead of the fixation patch PA. Examples of the solid substance include a solidified-methanol or the like.

Although it has been described above that the required nutrient component provided to the reaction region is re-absorbed into the patch PA in the process in which the patch PA is separated, some of the required nutrient components provided to the reaction region may stay in the reaction region without being re-absorbed into the culturing patch PA.

To completely remove the required nutrient component, the reaction region may be washed after the separation of the culturing patch PA (S320).

The washing may be performed by spraying a washing solution onto the reaction region.

Alternatively, the washing may also be performed using a patch PA that contains a washing solution, that is, a washing patch PA. For example, after separating the culturing patch PA, the washing patch PA may be brought into contact with the reaction region and separated therefrom. The washing patch PA may absorb and remove impurities or remaining required nutrient components on the plate PL. The washing solution used herein may include a tris buffered saline (TBS) or phosphate buffered saline (PBS) with Tween 20.

Conventionally, a method in which an object to be cultured float in a culture solution or a culture fluid in a liquid phase is provided to the object to be cultured applied on a wall of a petri dish or a method in which an object to be cultured is cultured on a culture medium such as agar has been used In comparison to such conventional methods, in the above-described culturing method, an object to be cultured may be cultured using a patch PA while the object to be cultured is applied on a plate PL.

In the method in which the liquid-phase culture fluid is used from among the conventional culturing methods, since the object to be cultured float in the liquid, it is difficult to two-dimensionally observe the object to be cultured. Also, even in the method in which the agar medium is used, observing the object to be cultured through visual inspection may be interfered by the agar medium.

In contrast, according to the present method, since the object to be cultured does not move freely on the plate PL but grows two-dimensionally there is an advantage in that it is easy to determine a degree of growth of the object to be cultured.

Also, according to the present method, since a smaller amount of required nutrient component, in comparison to conventional methods, may be efficiently utilized, there is an advantage in that an amount of required nutrient component being wasted can be reduced.

In addition, according to the present method, the required nutrient component may be provided as the patch PA comes into contact with the reaction region, and the providing of the required nutrient component may be stopped as the patch PA is separated from the reaction region. Particularly, as the required nutrient component that has already been provided to the reaction region is re-absorbed into the patch PA in the process in which the patch PA is separated, the interruption of providing of the required nutrient component may be precisely controlled. Accordingly, there is an advantage in that a degree of growth of the object to be cultured can be more precisely controlled in comparison to conventional methods. Such an advantage may be more pronounced due to the washing process using the washing patch PA.

It has been described above that the culturing method is performed using a single patch PA on a single plate PL. However, instead, at least one of the plate PL and the patch PA may be plural.

For example, an object to be cultured may be applied on each of a plurality of plates PL, and a culturing patch PA may be brought into contact with a reaction region on each plate PL for culturing the object to be cultured.

The types, concentrations, or the like of required nutrient components contained in each culturing patch PA may be different. Different types of required nutrient components or required nutrient components having different concentrations may be provided to the same object to be cultured on each plate PL, and culturing may be simultaneously performed. In this way, an optimal type or concentration of a required nutrient component may be determined regarding specific object to be cultured.

Also, after applying different types of an object to be cultured on each plate PL, the object to be cultured may be cultured using culturing patches PA that contain required nutrient components having the same concentration and components. Alternatively, different types of an object to be cultured may be applied on each plate PL, and culturing patches PA to be used may also contain different types of required nutrient components or required nutrient components having different concentrations.

In the culturing method of the present application, since culturing is possible even in a state in which only a very small amount of sample is applied on a slide glass, an overall experiment time may be shortened by simultaneously performing various types of culture.

5. Culture Test.

A culture test method according to an embodiment of the present application will be described below.

The culture test method according to the present application refers to testing a degree of growth of an object to be cultured.

For example, when the type of an object to be cultured is known, a culture test may be utilized to determine an extent to which the object to be cultured grow with respect to various required nutrient components. Conversely, when the type of an object to be cultured is unknown, the culture test may be used, in a reverse manner, to determine the type of an object to be cultured after applying a specific required nutrient component to the object to be cultured and obtaining a degree to which the object to be cultured have grown. As another example, the culture test may also be utilized to examine whether an object to be cultured have sufficiently grown for staining or observing the object to be cultured after culturing.

Of course, it should be noted that the culture test method according to the present application is not necessarily utilized for the purposes mentioned in the above-described examples.

The culture test method according to the present application may be used to test an object to be cultured which have been cultured using various culturing methods unmentioned herein or an object to be cultured which have been directly collected from a patient or an animal without being cultured, as well as a degree of growth of an object to be cultured which have been cultured with the above-described culturing method using the culturing patch PA.

The culture test may be performed by acquiring an image of an object to be cultured placed in the reaction region on the plate PL and analyzing the acquired image.

The acquisition of the image may be performed for an object to be cultured which have not been additionally processed for the image acquisition. Alternatively, an object to be cultured may be stained or a biochemical reaction may be induced in the object to be cultured, and then an image of the object to be cultured may be acquired. For example, a staining patch PA that contains a staining reagent may be brought into contact with an object to be cultured and separated therefrom to stain the object to be cultured, and then an image of the stained object to be cultured may be acquired. As another example, a patch PA that contains, instead of a staining reagent, an antigen or an antibody which biochemically reacts with an object to be cultured or another substance which binds specifically to the object to be cultured may be brought into contact with the object to be cultured and separated therefrom to induce a biochemical reaction (for example, color development, fluorescence development, or the like) in the object to be cultured, and then an image of the object to be cultured may be acquired.

The acquisition of the image may be performed using an optical device. The optical device may be any device capable of acquiring an image with a magnification suitable for detecting an object to be cultured such as cells or bacteria placed in the reaction region. For example, the optical device may include an optical sensor formed of a charge-coupled device (CCD) or a complementary metal-oxide semiconductor (CMOS), a tube configured to provide an optical path, a lens configured to adjust a magnification or focal length, and a memory configured to save an image acquired by the CCD or CMOS.

Figure 39:
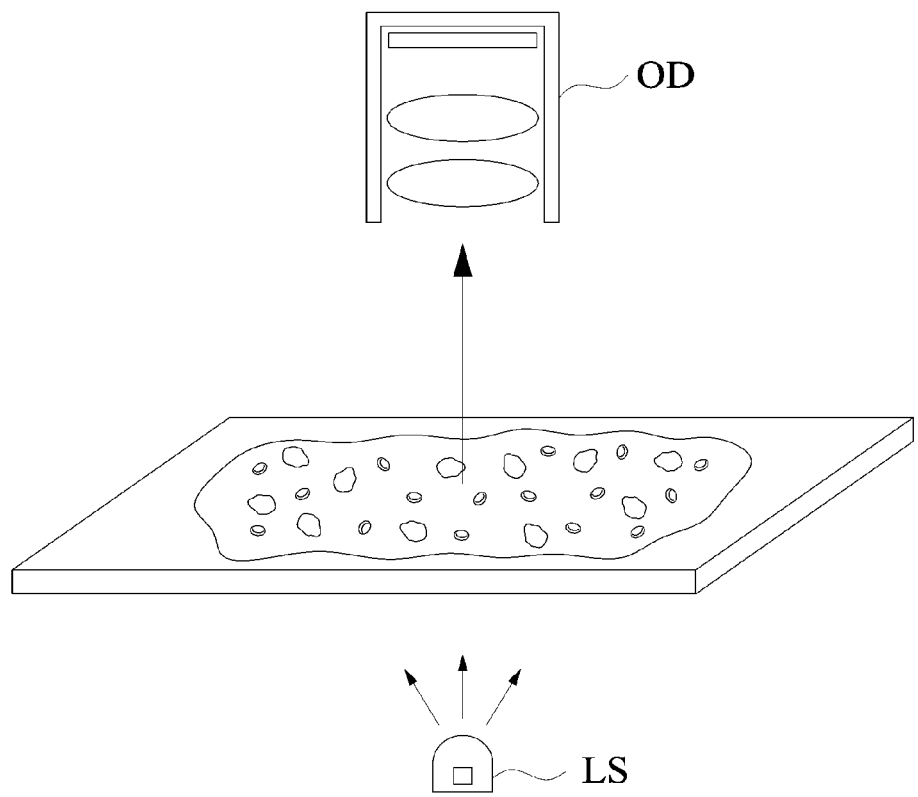
FIGS. 39 to 41 are views related to acquisition of an image of an object to be cultured according to an embodiment of the present application.
Figure 40:
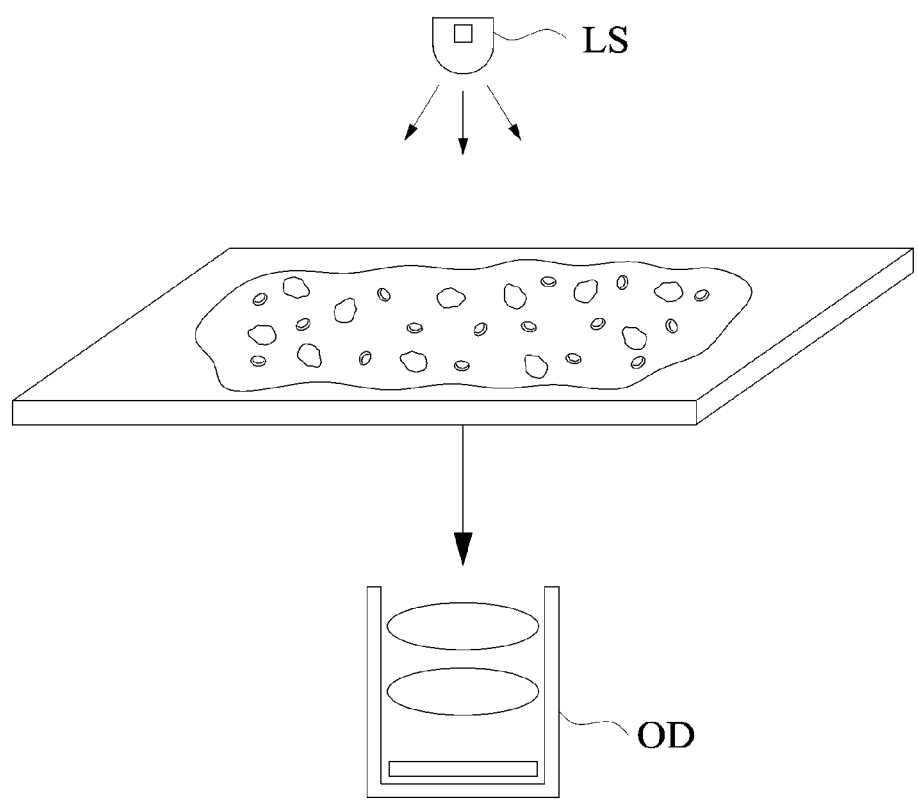
Figure 41:
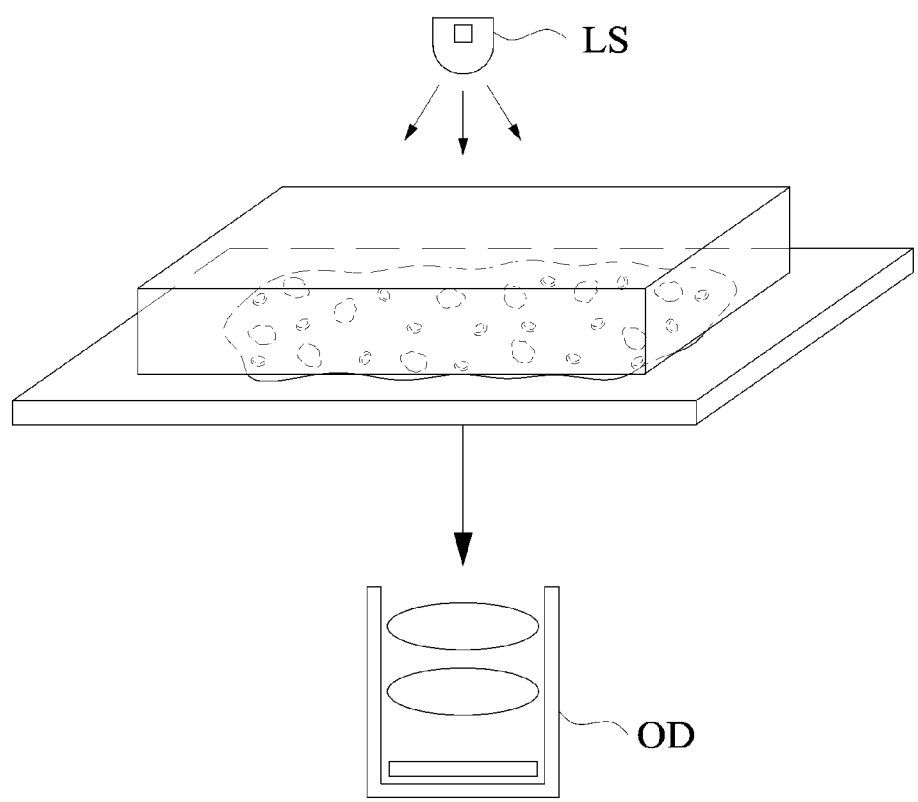

FIGS. 39 to 41 are views related to acquisition of an image of an object to be cultured according to an embodiment of the present application.

Referring to FIGS. 39 to 41, an optical device OD may directly acquire an image of an object to be cultured applied on a plate PL. The optical device OD may receive light that has been irradiated from a light source LS and has transmitted through the plate PL on which the object to be cultured is applied and acquire an image of the object to be cultured.

For example, referring to FIGS. 39 and 40, the optical device OD may acquire an image of a region on which the object to be cultured is applied while the culturing patch PA is separated from the plate PL. The plate PL being prepared with a material through which light output from the light source may transmit easily as possible, may be preferable. Also, the light source may output white light or output a wavelength in a specific wavelength band.

Referring again to FIG. 39, the optical device OD may be disposed at a surface on which an object to be cultured is applied (hereinafter referred to as "front surface") of a slide glass, and the light source LS may be disposed at a surface opposite the front surface of the slide glass, i.e., a rear surface side of the slide glass. Due to such arrangement, the optical device OD may receive light that has been irradiated from the rear surface side of the slide glass by the light source LS and has passed through the slide glass and acquire an image of the object to be cultured.

Referring again to FIG. 40, the optical device OD may be disposed at the rear surface side of the slide glass, and the light source LS may be disposed at the front surface side of the slide glass. Due to such arrangement, the optical device OD may receive light that has been irradiated from the front surface side of the slide glass by the light source LS and has passed through the slide glass and acquire an image of the object to be cultured.

As another example, referring to FIG. 41, the optical device OD may acquire an image of a region on which an object to be cultured is applied while the culturing patch PA is in contact with the plate PL.

Referring again to FIG. 41, the optical device OD may be disposed at the rear surface side of the slide glass, and the light source LS may be disposed at the front surface side of the slide glass. Due to such arrangement, the optical device OD may receive light that has been irradiated from the front surface side of the slide glass by the light source LS and has passed through the slide glass and acquire an image of the object to be cultured.

When an image is acquired while the patch PA is in contact with the plate PL, the optical device OD may be disposed at the front surface side of the slide glass, and the light source LS may be disposed at the rear surface side of the slide glass. However, when the optical device OD is disposed at the front surface side, since the optical device OD has to acquire an image via the patch PA, it may be difficult to obtain a clear image due to reasons such as difficulty in focusing the optical device OD.

Therefore, when the image is acquired while the patch PA is in contact with the plate PL, it may be preferable that the optical device OD be disposed at the rear surface side of the plate PL. The light source LS being disposed at the front surface side of the plate PL such that light is applied to the plate PL via the patch PA may rather have an advantage in that luminance is made uniform due to the light scattering or diffusion phenomenon that occurs in the patch PA.

Also, when the optical device OD is disposed at the front surface side of the plate PL to receive light that transmits through the patch PA, it may be important to finely or uniformly control a thickness of the patch PA.

When an image is acquired while the patch PA is in contact with the plate PL, the patch PA may also serve as a kind of an optical filter.

A measurement of a degree of growth of an object to be cultured according to the culture test may be performed by acquiring numerical information or morphological information of various object to be cultured from acquired images.

For example, the image may be provided to an operator through a monitor of a computer or medical equipment or the like. The operator may determine the number, size, morphology, and the like of cells, tissues, blood cells, or bacteria from the image and determine a degree of growth of the object to be cultured.

As another example, an electronic device with an image analysis program installed therein may acquire an image from an optical device, determine the number, size, morphology, and the like of cells, tissues, blood cells, or bacteria from the image, and determine a degree of growth of the object to be cultured.

The image analysis program may analyze the acquired image. Specifically, the image analysis program may acquire numerical information and morphological information of an object to be cultured from the acquired image. The numerical information may include the number (count) or size of an object to be cultured, and the morphological information may include the size of the object to be cultured, the shape of the objects to be cultured, or the like.

The image analysis program may also determine a type of an object to be cultured or a degree of growth of the object to be cultured on the basis of the numerical information or morphological information.

The above-described image analysis program may also perform the above-described determination process in accordance with a predetermined algorithm or in accordance with an algorithm formed through machine learning such as deep learning.

5.1 Culture Test Method—First Embodiment

Figure 42:
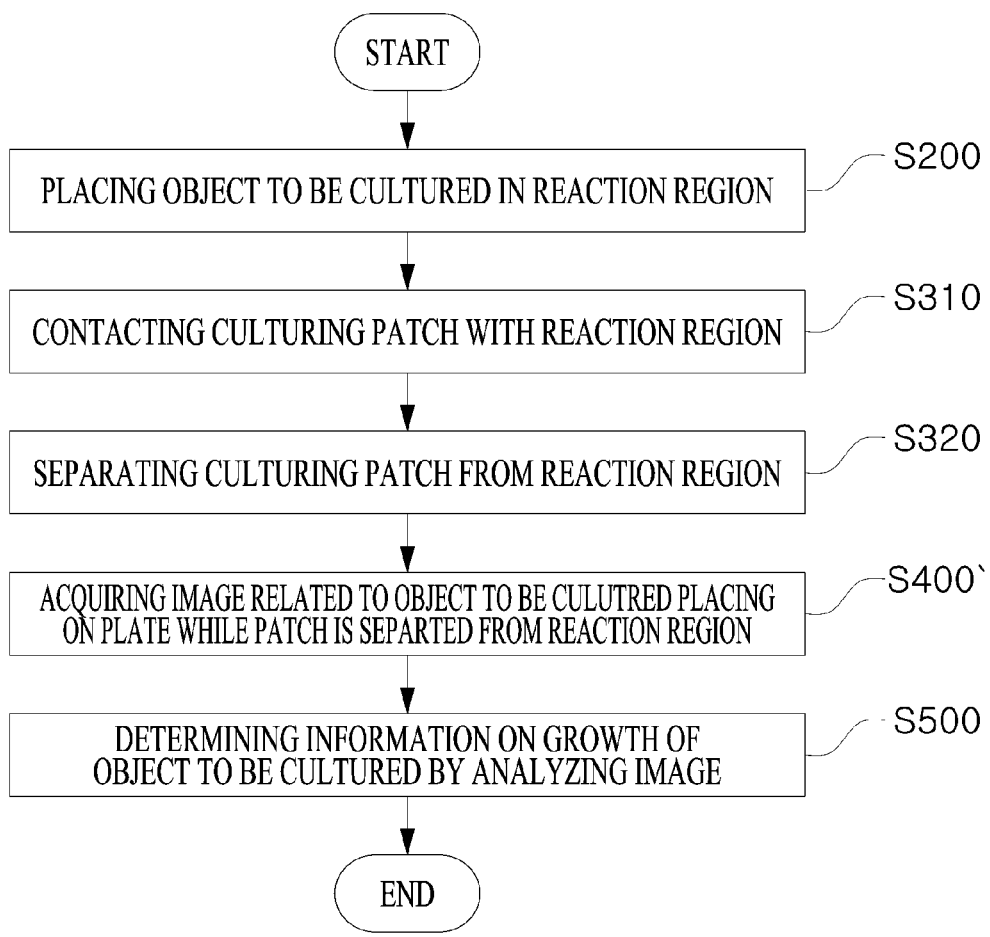
FIG. 42 is a flowchart of an embodiment of a culture test method of the present application.

FIG. 42 is a flowchart of an embodiment of a culture test method of the present application.

Referring to FIG. 42, a culture test method according to an embodiment of the present application may include placing object to be cultured, which is test object, in a reaction region (S200), contacting a culturing patch PA with the object to be cultured (S310), separating the culturing patch PA from the reaction region (S320), acquiring an image of the object to be cultured on a plate in as state in which the patch PA is separated from the reaction region (S400'), and determining information on growth of the object to be cultured by analyzing the acquired image (S500).

Figure 43:
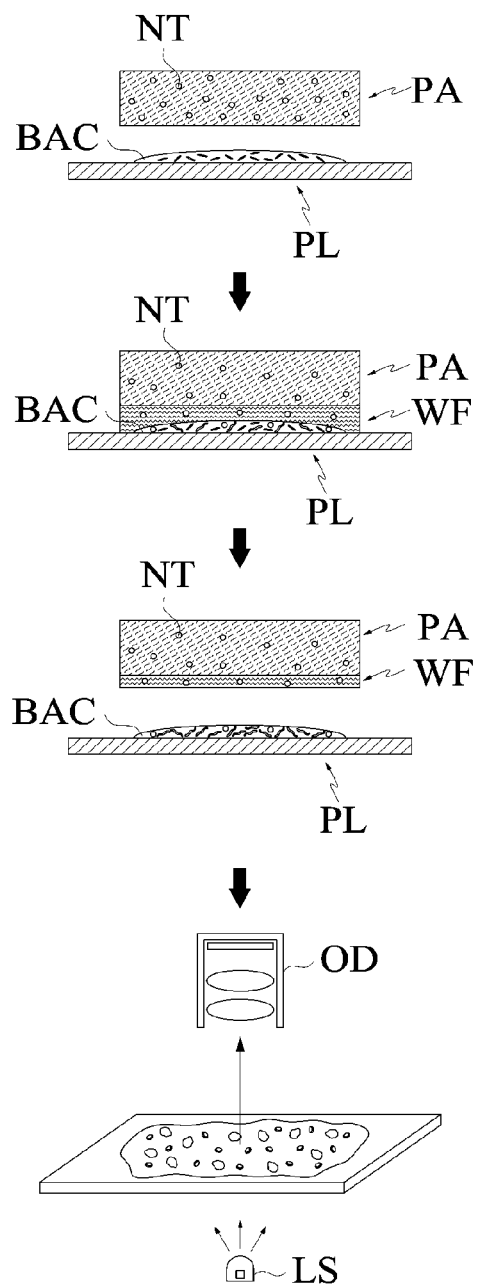
FIG. 43 is an operational view of the embodiment of the culture test method of the present application.

FIG. 43 is an operational view of the embodiment of the culture test method of the present application.

Referring to FIG. 43, a culture test may be performed by placing object to be cultured in a reaction region on a plate PL (S200), bringing the patch PA into contact with the object to be cultured (S310) to provide a required nutrient component to the object to be cultured for the object to be cultured to grow, separating the patch PA from the reaction region (S320), acquiring an image of the object to be cultured by acquiring an image of the reaction region on the plate PL in a state in which the patch PA is not in contact with the reaction region, and analyzing the acquired image in accordance with the above-described culturing method. The degree of growth of the object to be cultured may be determined on the basis of the number or size of the object to be cultured in accordance with analysis of the image (S500).

Figure 44:
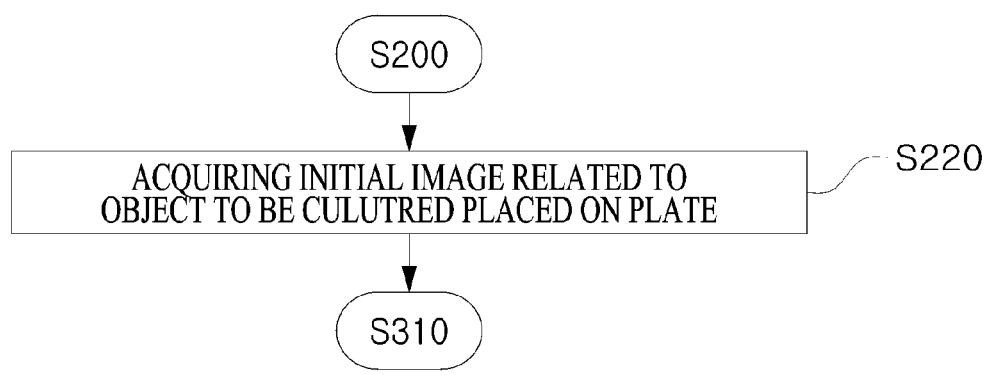
FIG. 44 is a flowchart of a modified example of the embodiment of the culture test method of the present application.

FIG. 44 is a flowchart of a modified example of the embodiment of the culture test method of the present application.

Referring to FIG. 44, a modified example of the embodiment of the culture test method of the present application may further include acquiring an initial image related to the object to be cultured placed on the plate PL (S220). The initial image may refer to an image of the object to be cultured after the object to be cultured is applied on the plate PL and before a component required for growth is provided to the object to be cultured for the growth of the object to be cultured.

The acquiring of the initial image may be performed at a time point after the object to be cultured is applied on the plate PL and before the culturing patch PA is brought into contact with the reaction region. Therefore, in the determining of the degree of growth of the object to be cultured (S500), the initial image contains information related to the number or size of the object to be cultured before the growth of the object to be cultured.

The degree of growth of the object to be cultured may be determined comparing information related to the object to be cultured obtained by analyzing the initial image and information related to the object to be cultured obtained by analyzing the image obtained in Step S400'. Alternatively, the degree of growth may also be determined by comparing the initial image and the image acquired in Step S400' (for example, difference operation or the like).

In Step S500, the degree of growth may be determined by additionally taking into consideration a culture time, a type of required nutrient component, and an amount of provided required nutrient component. In addition, the degree of growth may also be determined by additionally taking into consideration various external conditions including a culturing temperature or a humidity level.

Figure 45:
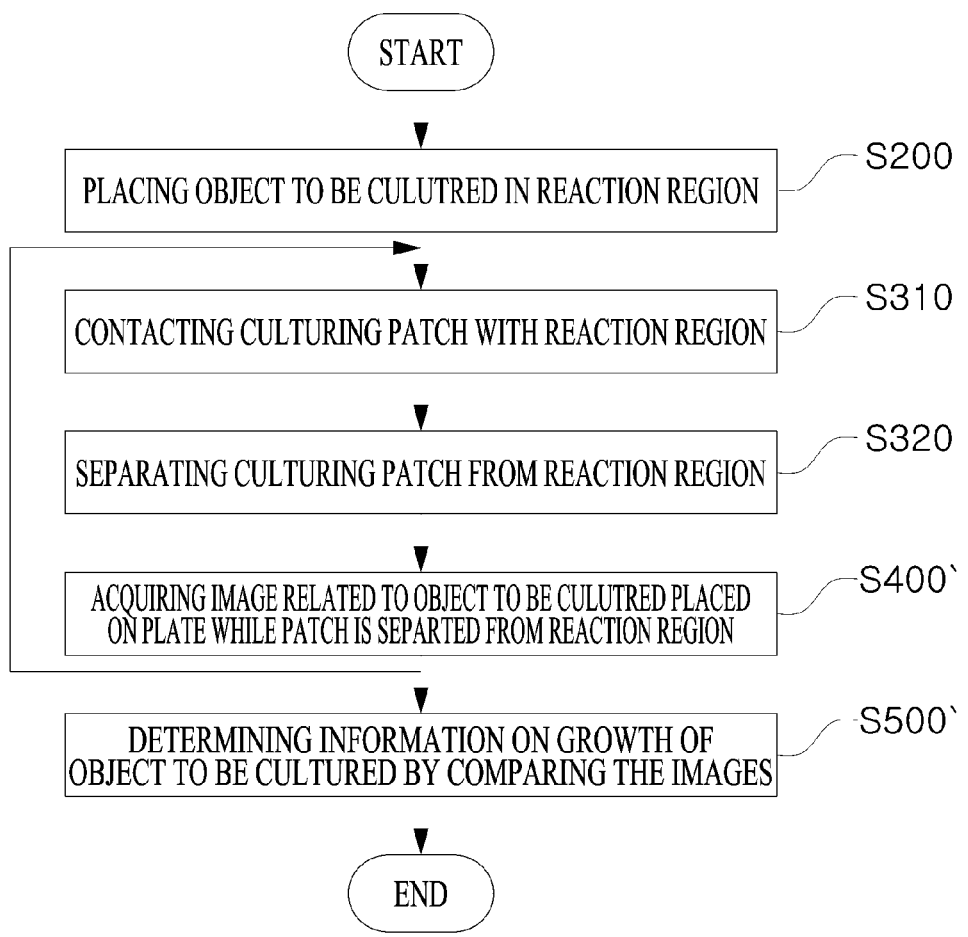
FIG. 45 is a flowchart of another modified example of the embodiment of the culture test method of the present application.

FIG. 45 is a flowchart of another modified example of the embodiment of the culture test method of the present application.

Referring to FIG. 45, in the other modified example of the embodiment of the culture test method of the present application, an image related to an object to be cultured placed on the plate PL may be acquired several times. The plurality of images may be images acquired at different time points after culture has begun. Accordingly, when determining the degree of culture, a comparative analysis may be performed on the plurality of images acquired at different time points, and the degree of growth of the object to be cultured may be determined.

Specifically, the other modified example of the embodiment of the culture test method of the present application may include placing an object to be cultured, which is test object, in a reaction region (S200), contacting the culturing patch PA with the object to be cultured (S310), separating the culturing patch PA from the reaction region (S320), acquiring images related to the object to be cultured on the plate in a state in which the patch PA is separated from the reaction region (S400'), and determining information on growth of the object to be cultured by comparing the plurality of images (S500"). In this case, after Step S400' ends, the process may return to Step S310, and Steps S310 to S400' may be repeated several times.

Steps S310 and S320 may be performed repeatedly using a single culturing patch PA. Alternatively, a plurality of culturing patches PA may be prepared, and Steps S310 and S320 may be performed by replacing the patches PA. Alternatively, the patch PA may be replaced after Steps S310 and S320 are repeated a predetermined number of times.

The acquiring of the images (S400') may be performed at different time points. For example, the acquiring of the images (S400') may be performed at predetermined intervals. For example, an image may be acquired every 20 minutes.

The determining of the growth information (S500) may include comparing the plurality of images acquired in the acquiring of the images (S400') and a degree of growth of object to be cultured with time may be determined. For example, by comparing a first image acquired at a first time point and a second image acquired at a second time, a degree of growth of object to be cultured occurred between the first time point and the second time point may be determined.

That is, the determining of the growth information by comparing images (S500') may include acquiring a plurality of images, acquiring numerical or morphological information of the object to be cultured from the images, calculating differences in the numerical or morphological information of an object to be cultured between the images, acquiring information on time points at which the plurality of images have been acquired, obtaining time differences between the time points at which the images have been acquired, and determining, in consideration of the time differences and the information differences, the degree of growth with time of the object to be cultured.

Alternatively, the determining of the growth information by comparing images (S500') may include acquiring a plurality of images, obtaining differences between images according to a difference operation or the like, acquiring information on time points at which the plurality of images have been acquired, calculating time differences between the time points at which the images have been acquired, and determining the degree of growth of the objects to be cultured with time in consideration of the time differences and the information differences.

It has been described above that Steps S310 to S400' are repeated and then Step S500 is performed in the other modified example of the embodiment of the culture test method of the present disclosure. According to the above description, after a desired number of images are acquired, information on growth of an object to be cultured may be determined by comparing the acquired images, and. However, instead, Steps S310 to S500' may be performed repeatedly. At this time, in Step S500, a comparative analysis may be performed on a most recently acquired image and an immediately-preceding image to determine information on growth of an object to be cultured. Here, by comparing a recent image and an immediately-preceding image in this way, a growth information may be periodically acquired in accordance with intervals at which Steps S310 to S500' are repeated. For example, when Steps S310 to S500' are repeated every 20 minutes, a degree of growth may be determined every 20 minutes.

Figure 46:
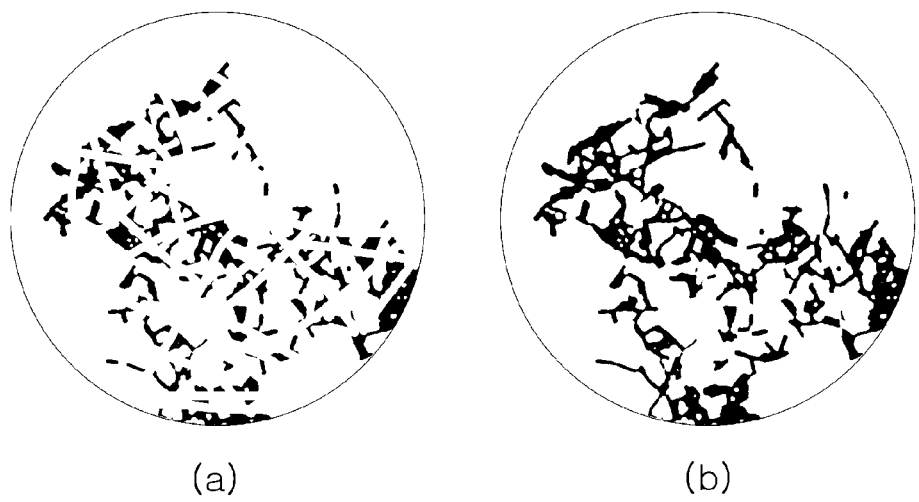
FIG. 46 is an example of an image of an object to be cultured according to the present application.

FIG. 46 is an example of an image of an object to be cultured according to the present application.

Images shown in FIG. 46 may be an image acquired in Step S400' which is performed for an n-th time and an image acquired in Step S400' which is performed for an (n+1))th time. Comparing the two images, it can be seen that bacteria have grown further in the (n+1))th image than in the n-th image. Here, n may be a natural number that is 1 or greater.

5.2 Culture Test Method—Second Embodiment

Figure 47:
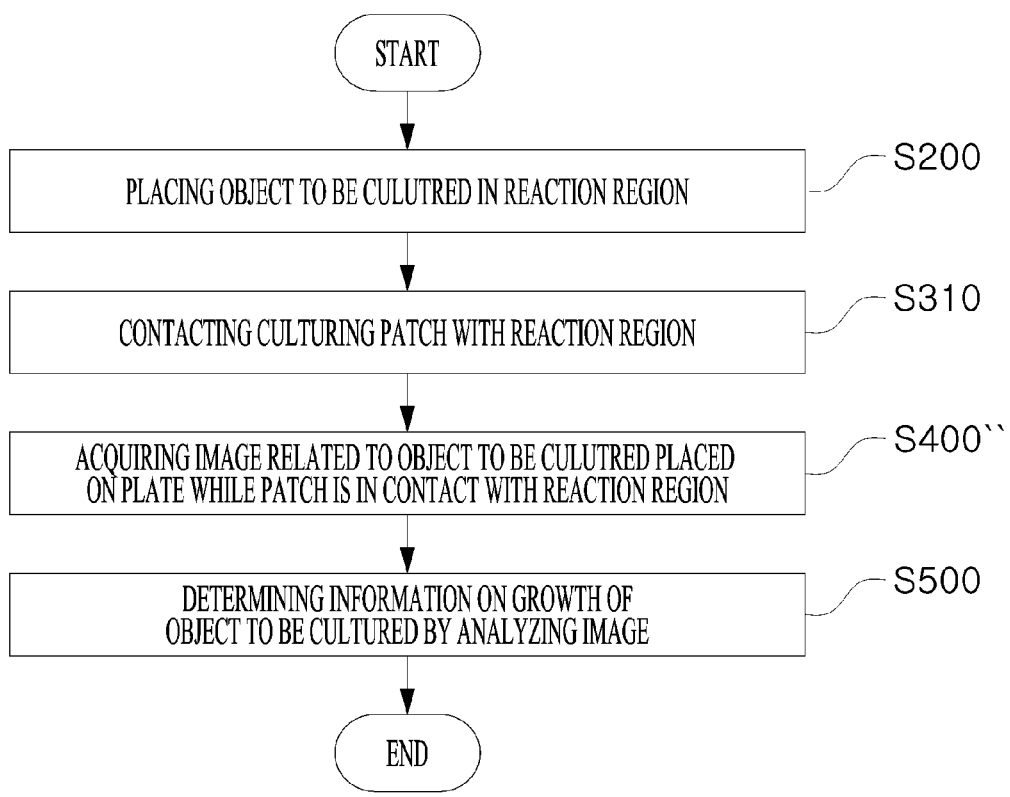
FIG. 47 is a flowchart of another embodiment of a culture test method of the present application.

FIG. 47 is a flowchart of another embodiment of a culture test method of the present application.

Referring to FIG. 47, a culture test method according to the other embodiment of the present application may include placing an object to be cultured, which is test object, in a reaction region (S200), contacting a culturing patch PA with the object to be cultured (S310), acquiring an image of the object to be cultured placed on a plate while the patch PA is in contact with the reaction region (S400"), and determining information on growth of the object to be cultured by analyzing the image (S500).

It has been described above with reference to the embodiment of the culture test method of the present application shown in FIG. 42 that an image is acquired after the culturing patch PA is separated from the reaction region. However, in the other embodiment of the culture test of the present application, an image may be acquired in a state in which the culturing patch PA is in contact with the reaction region.

Figure 48:
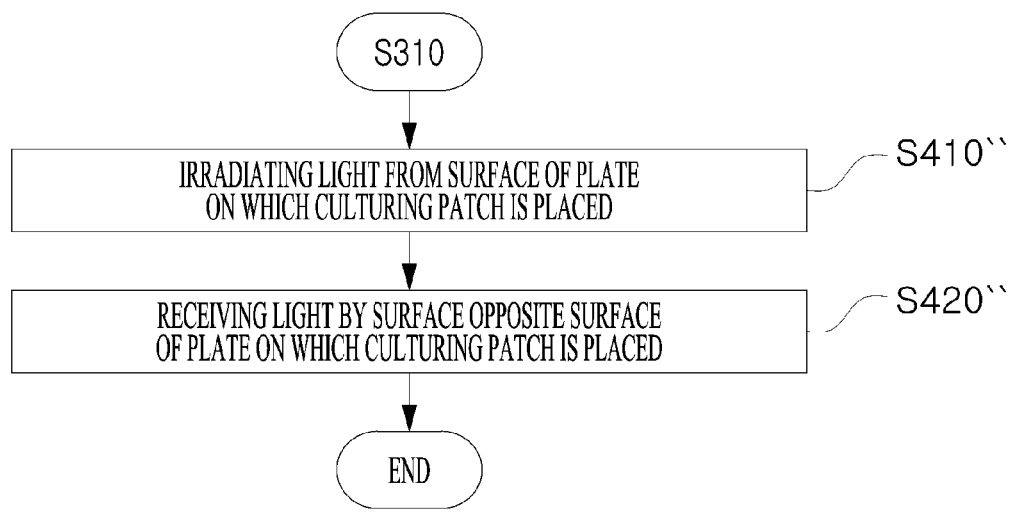
FIG. 48 is a flowchart of acquiring an image in the other embodiment of the culture test method according to the present application.
Figure 49:
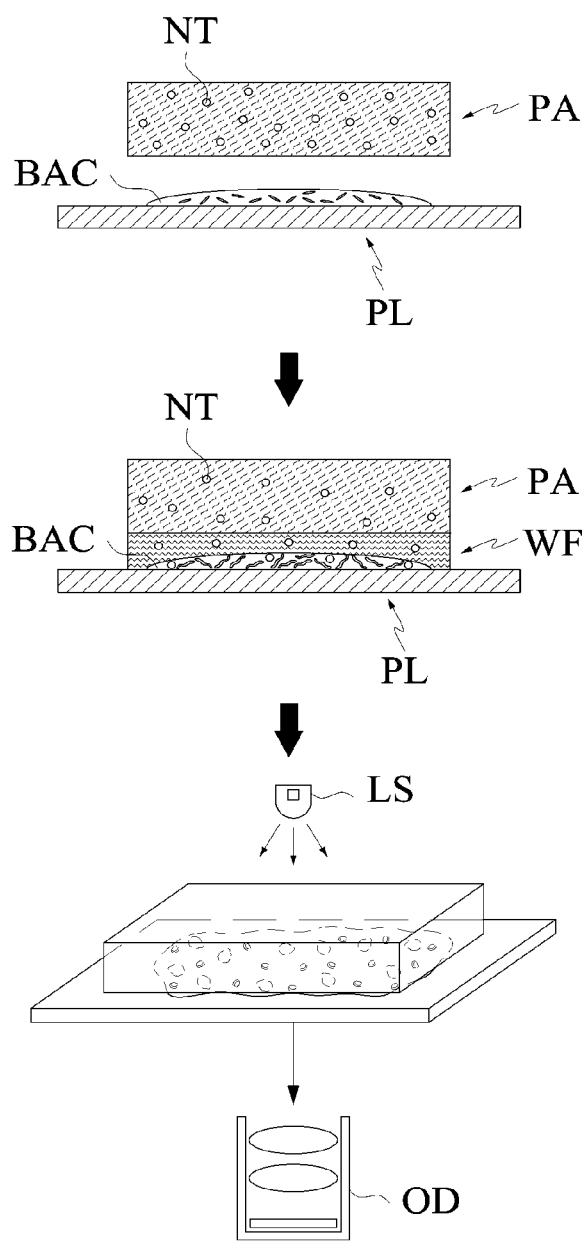
FIG. 49 is an operational view of the other embodiment of the culture test method of the present application.

FIG. 48 is a flowchart of acquiring an image in the other embodiment of the culture test method according to the present application, and FIG. 49 is an operational view of the other embodiment of the culture test method of the present application.

Referring to FIG. 48, in the other embodiment of the culture test method according to the present application, the acquiring of the image (S400") may include irradiating light from a surface on which the culturing patch PA is placed (that is, front surface) of a plate PL by a light source LS (S410") and receiving the light from a surface opposite the surface on which the culturing patch PA is placed (that is, rear surface) of the plate PL by the optical device OD (S420").

Referring to FIG. 49, in the present embodiment, the culturing patch PA continuously remains in contact with the reaction region even during the image acquisition. Consequently, according to the present embodiment, there is no inconvenience of having to separate the culturing patch PA. Also, according to the present embodiment, since a required nutrient component is provided from the culturing patch PA to the object to be cultured even during the image acquisition, there is an advantage in that the growth of the object to be cultured is not interrupted. Also, since the culturing patch PA is not separated and thus the reaction region is not exposed to air, there is an advantage in that the reaction region is not exposed to foreign substances including bacteria outside the reaction region.

In this case, it may be preferable that the optical device OD acquire an image of the object to be cultured placed in the reaction region from the rear surface of the plate PL for facilitating acquiring the images.

Figure 50:
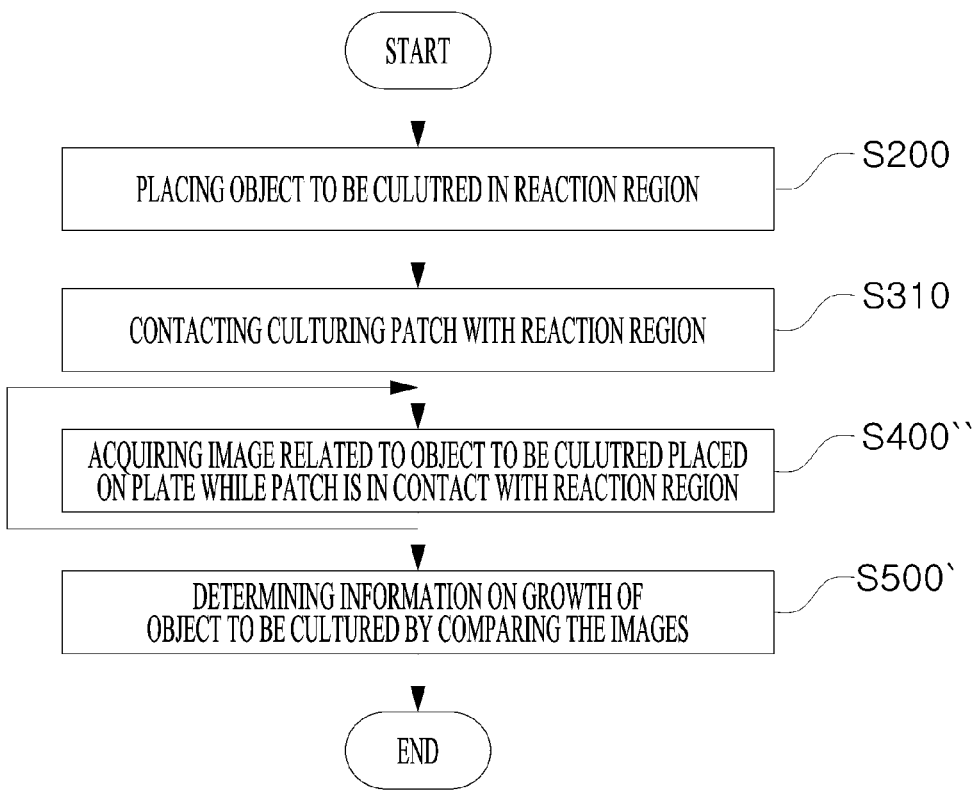
FIG. 50 is a modified example of the other embodiment of the culture test method of the present application.

FIG. 50 is a modified example of the other embodiment of the culture test method of the present application.

Referring to FIG. 50, in the modified example of the other embodiment of the culture test method of the present application, an image related to the object to be cultured placed on the plate PL may be acquired several times. The plurality of images may be images acquired at different time points after culture has begun. Accordingly, when determining the degree of culture, the degree of growth of the object to be cultured may be determined by comparing the plurality of images acquired at different time points.

Specifically, in the other modified example of the embodiment of the culture test method of the present application, the acquiring of the image related to the object to be cultured placed on the plate while the patch PA is in contact with the reaction region (S400") may be repeated. In this case, the acquiring of the image (S400") which is repeated may be performed at different time points. For example, the acquiring of the image (S400') may be performed at predetermined intervals. For example, an image may be acquired every 20 minutes. As another example, the acquiring of the image (S400") may including acquiring a video image with time.

In the determining of the growth information (S500), a degree of growth of an object to be cultured with time may be determined by comparing the plurality of images acquired in the acquiring of the image (S400"). For example, by comparing a first image acquired at a first time point and a second image acquired at a second time point, a degree of growth of an object to be cultured occurred between the first time point and the second time point may be determined.

It has been described above with reference to the modified example of the other embodiment of the culture test method of the present disclosure that Step S400" is repeated and then Step S500 is performed. However, instead, Steps S400' to S500' may be repeated.

Particularly, in the present modified example, since an image may be acquired while the patch PA is in contact with the reaction region without a process of separating the patch PA from the reaction region, there is an advantage in that, in addition to being able to periodically acquire images at predetermined intervals, a degree of growth may be analyzed in real time by acquiring a video or acquiring images in very short intervals.

6. Drug Test

A drug test method according to an embodiment of the present application will be described below.

The drug test method according to the present application refers to testing an effect of a drug.

A drug test may be utilized to determine an influence of a drug on an object to be cultured. For example, a drug test may be performed to determine an effect of an antibiotic on bacteria or sensitivity of bacteria to an antibiotic. As another example, a drug test may be utilized to determine an effect of a drug on various cells.

Of course, it should be noted that the drug test method according to the present application is not necessarily utilized for the purposes mentioned in the above-described examples.

The drug test method according to the present application may be used to test object to be cultured which have been cultured using various culturing methods unmentioned herein or an object to be cultured which have been directly collected from a patient or an animal without being cultured, as well as an influence of a drug on an object to be cultured which have been cultured with the above-described culturing method using the patch PA.

The drug test may be performed by acquiring an image of an object to be cultured placed in the reaction region on the plate PL and analyzing the acquired image. The acquisition of the image may be performed similarly as that in the above-described culture test.

A measurement of an effect of a drug according to the drug test (for example, a degree of bacterial inhibition or death due to an antibiotic) may be performed by acquiring numerical information or morphological information of various objects to be cultured from acquired images. In this case, the measurement of the effect of a drug may be performed similarly as the measurement of a degree of growth of an object to be cultured in the above-described culture test method.

6.1 Drug Test Method—First Embodiment

Figure 51:
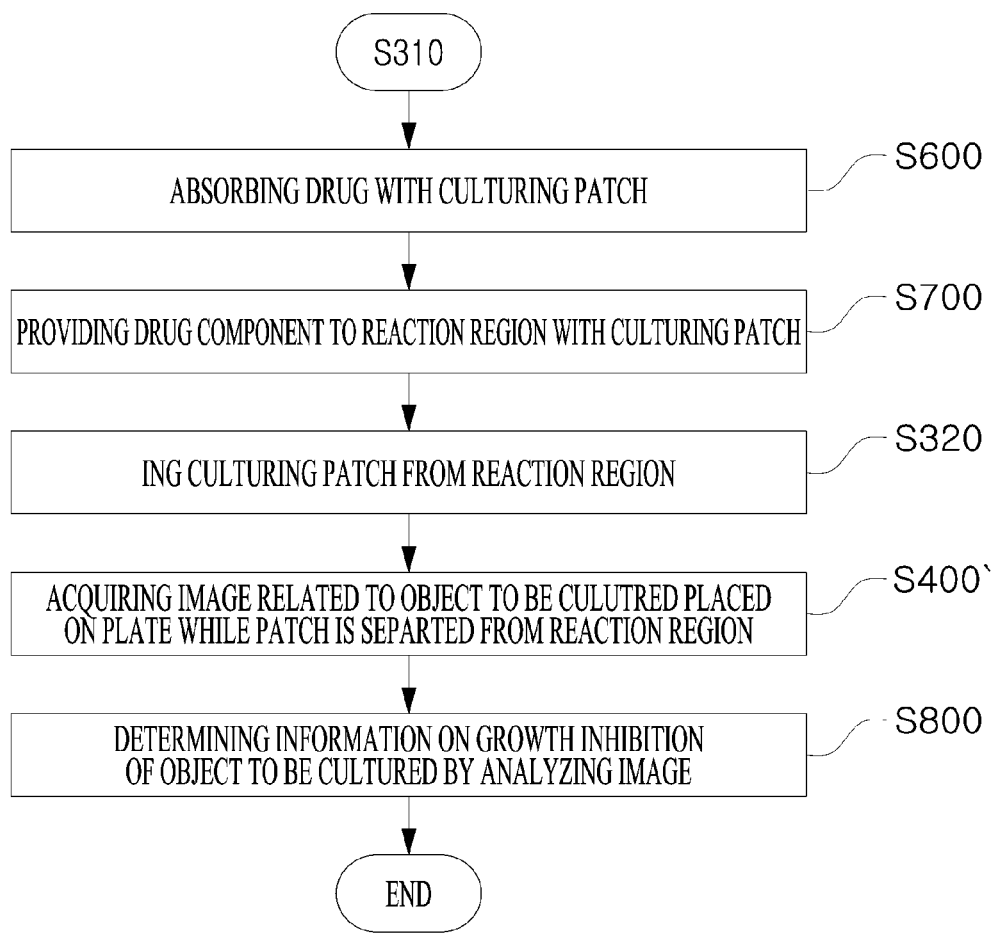
FIG. 51 is a flowchart of an embodiment of a drug test method of the present application.

FIG. 51 is a flowchart of an embodiment of a culture test method of the present application.

Referring to FIG. 51, a drug test method according to an embodiment of the present application may include in a state in which a culturing patch PA is in contact with a reaction region (S310), absorbing a drug by the culturing patch PA (S600), providing the drug to the reaction region by the culturing patch PA (S700), separating the culturing patch PA from the reaction region (S320), acquiring an image of an object to be cultured placed on the plate PL in a state in which the culturing patch PA is separated from the reaction region (S400'), and testing an influence of the drug on the object to be cultured by analyzing the image (S800).

Figure 52:
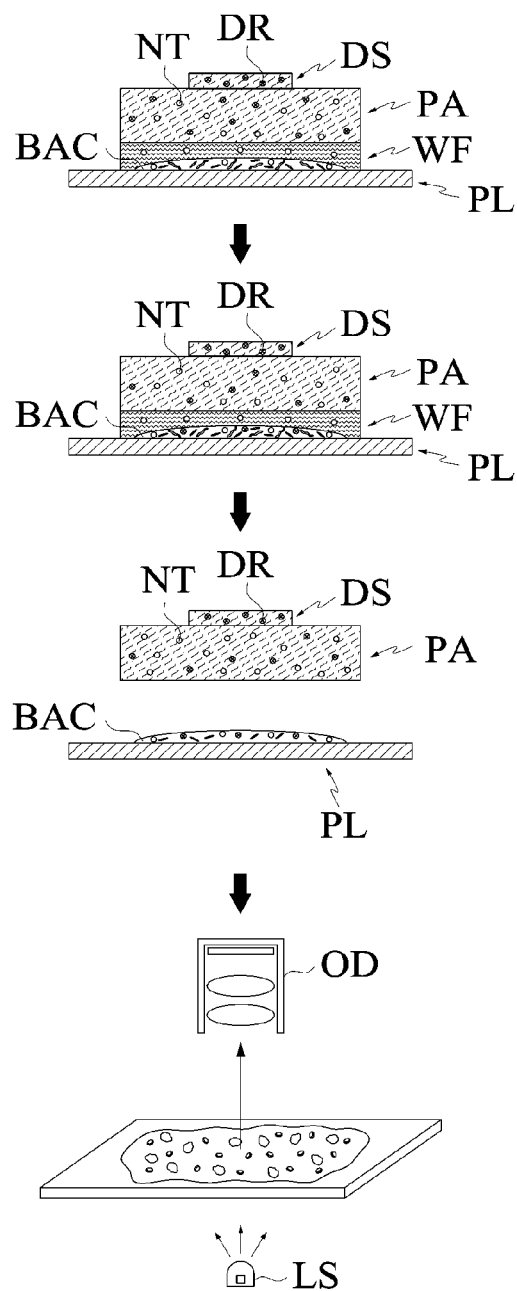
FIG. 52 is an operational view of the embodiment of the drug test method of the present application.

FIG. 52 is an operational view of the embodiment of the drug test method of the present application.

Referring to FIG. 52, in the embodiment of the drug test method of the present application, a drug test may be performed on an object to be cultured which have been cultured in accordance with the above-described culturing method of the present disclosure. Therefore, in the present embodiment, the drug test may begin in a state in which the culturing patch PA is in contact with the reaction region on the plate PL on which the object to be cultured is located.

In a state in which the culturing patch PA is in contact with the reaction region (S310), the culturing patch PA may absorb the drug (S600). For example, a drug sheet DS that contains a drug DR may be provided at an outer surface of the culturing patch PA. The culturing patch PA may absorb the drug DR from the drug sheet DS into the culturing patch PA.

When the drug is absorbed into the patch PA, the culturing patch PA may provide the drug to the reaction region through a water film WF between the plate PL and the patch PA while in contact with the plate PL. The object to be cultured placed in the reaction region receive the drug provided to the reaction region and are affected by the drug. For example, when the object to be cultured is bacteria and the drug is an antibiotic, the object to be cultured may be growth-inhibited or killed due to the antibiotic.

When a sufficient time has elapsed after the providing of the drug, the patch PA may be separated from the reaction region (S320), and an image of the reaction region on the plate PL may be acquired (S400').

When the image is acquired, numerical information and morphological information of the object to be cultured may be acquired from the image, and on the basis of the acquired information, an influence of the drug on the object to be cultured may be obtained (S800). For example, when an antibiotic is provided to bacteria, a degree of growth inhibition of bacteria and a degree of death of bacteria due to the antibiotic may be determined on the basis of changes in the size and number of bacteria due to the antibiotic. For example, when an activity accelerator is provided to cells, an effect of the accelerator may be determined in consideration of a degree of growth of the cells or an amount of substance secreted from the cells.

Since the determining of the influence of the drug may be performed similarly as the determining of the degree of growth of the object to be cultured in the culture test, detailed description thereof will be omitted.

In the present embodiment, for the image acquisition, Steps S310 to S400' may be repeated. Also, in the present embodiment, the determining of the effect of the drug may be periodically performed by repeating Steps S310 to S800. In addition, in the present embodiment, before Step S310 is performed, an initial image may be acquired before the drug is provided in a state in which the culturing patch PA is spaced apart from the plate PL before Step S310 is performed.

When an initial image has been acquired or an image has been acquired several times, comparing the plurality of images each other to determine an influence of the drug with time is also possible. Since the determining of the influence of the drug may be performed similarly as the description given above with respect to the culture test method of the present application expect that the type or concentration of the drug, instead of a required nutrient component, is taken into consideration, detailed description thereof will be omitted.

6.2 Drug Test Method—Second Embodiment

Figure 53:
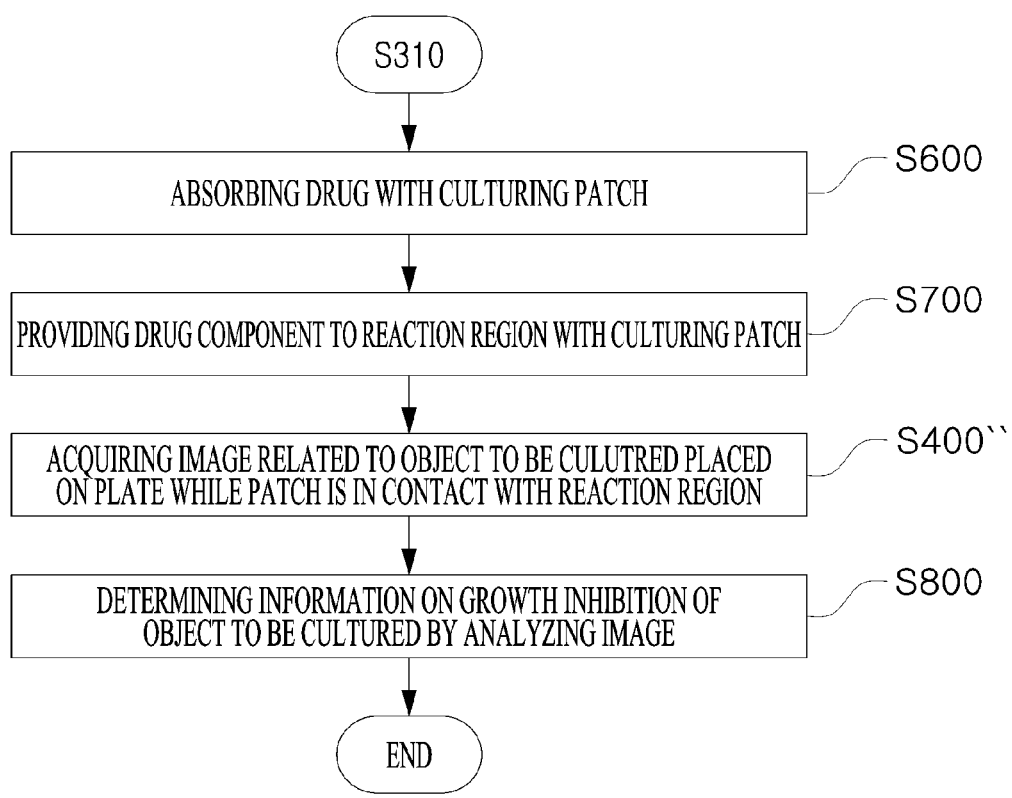
FIG. 53 is a flowchart of another embodiment of a drug test method of the present application.

FIG. 53 is a flowchart of another embodiment of a drug test method of the present application.

Referring to FIG. 53, the drug test method according to the other embodiment of the present application may include absorbing a drug by the culturing patch P (S600) in state in which the culturing patch PA is in contact with the reaction region (S310), delivering the drug to the reaction region by the culturing patch PA (S700), acquiring an image related to an object to be cultured placed on the plate PL in state in which the culturing patch PA is in contact with the reaction region (S400"), and testing an influence of the drug on the object to be cultured by analyzing the image (S800).

Figure 54:
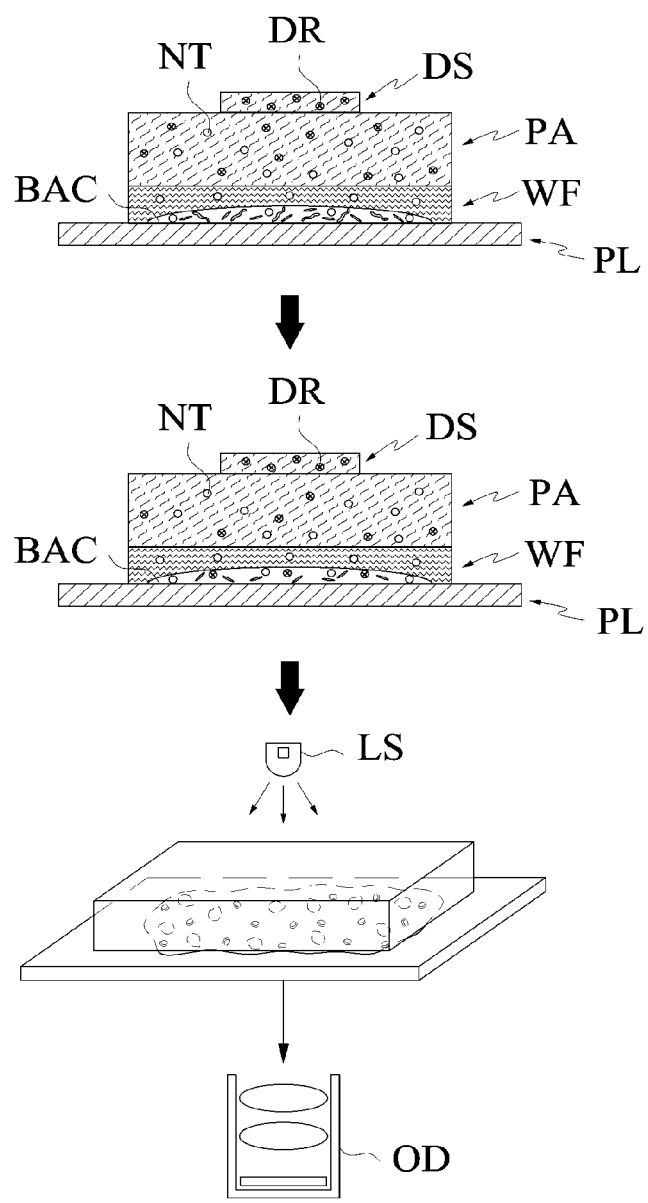
FIG. 54 is an operational view of the other embodiment of the drug test method of the present application.

FIG. 54 is an operational view of the other embodiment of the drug test method of the present application.

Referring to FIG. 54, in the other embodiment of the drug test method of the present application, a drug test may be performed on an object to be cultured which have been cultured in accordance with the above-described culturing method of the present application. Consequently, in the present embodiment, the drug test may begin in a state in which the culturing patch PA is in contact with the reaction region on the plate PL on which the object to be cultured is located.

In a state in which the culturing patch PA is in contact with the reaction region (S310), the culturing patch PA may absorb the drug (S600), and the providing of the drug to the reaction region by the culturing patch PA (S700) may be performed similarly as the description given above with respect to the previous embodiment of the drug test method of the present disclosure.

When a sufficient time has elapsed after the providing of the drug, an image of the reaction region on the plate PL may be acquired in a state in which the patch PA is in contact with the reaction region, that is, the patch PA is not separated from the reaction region (S400").

Since differences between acquiring an image in state in which the patch PA is in contact with the plate PL and acquiring an image while the contact is released have already been described with respect to the culture test method of the present application, detailed description thereof will be omitted.

When the image is acquired, on the basis of the acquired image, an influence of the drug may be determined. For example, the influence of the drug may be information on growth inhibition or the like. Since further details on the influence of the drug have already been described with respect to the previous embodiment of the drug test, detailed description thereof will also be omitted.

6.3 Drug Test Method—Third Embodiment

Figure 55:
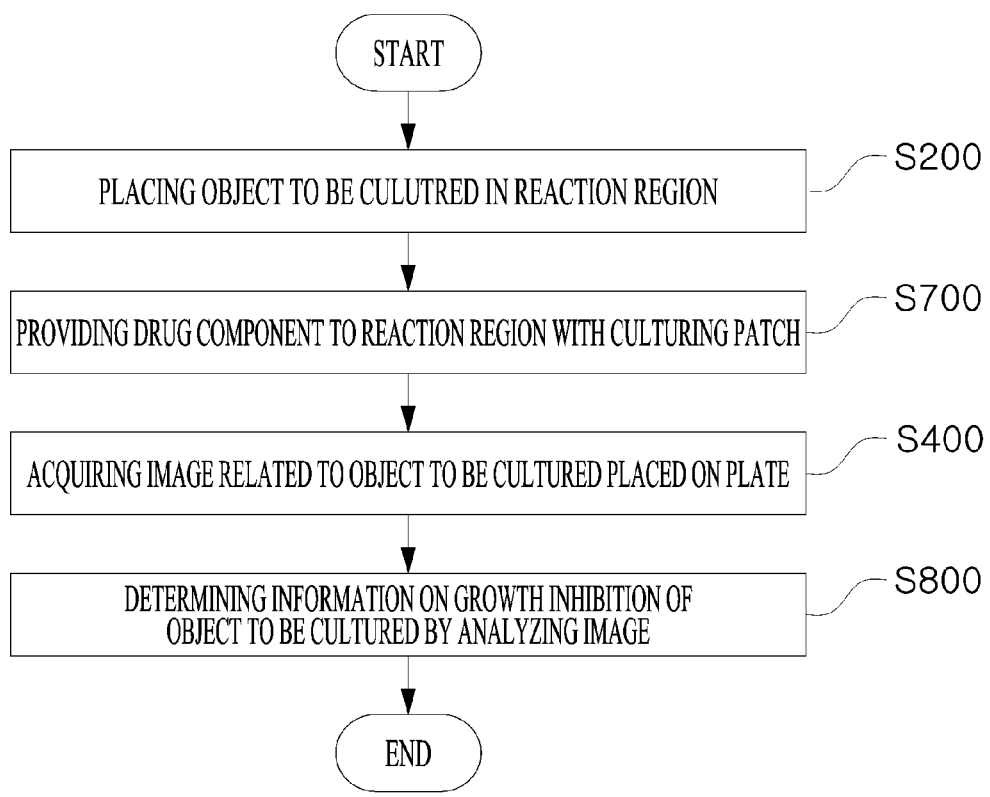
FIG. 55 is a flowchart of yet another embodiment of a drug test method of the present application.

FIG. 55 is a flowchart of yet another embodiment of a drug test method of the present application.

Referring to FIG. 55, the drug test method according to yet another embodiment of the present application may include placing an object to be cultured in a reaction region (S200), providing a drug to the reaction region by the culturing patch PA (S700), acquiring an image of the object to be cultured placed on the plate PL (S400), and testing an influence of the drug on the object to be cultured by analyzing the image (S800).

In the previous embodiments of the drug test method described above, the drug is provided to the object to be cultured by injecting the drug into the culturing patch PA through a drug sheet or the like in a state in which an object to be cultured is cultured using the culturing patch PA of the present disclosure.

However, in the present application, a drug test is not necessarily applied only to an object to be cultured using the culturing patch PA. In Step S200 of the present embodiment, the object to be cultured may also be cultured using a culturing method other than that of the present application. Also, although an object to be drug-tested is assumed as the object to be cultured in the present embodiment, the object to be drug-tested may also be directly-collected objects instead of the object to be cultured.

Therefore, the placing of the object to be cultured in the reaction region (S200) should be broadly interpreted as applying the object to be cultured according to the present application or other object to be drug-tested on the plate PL.

Figure 56:
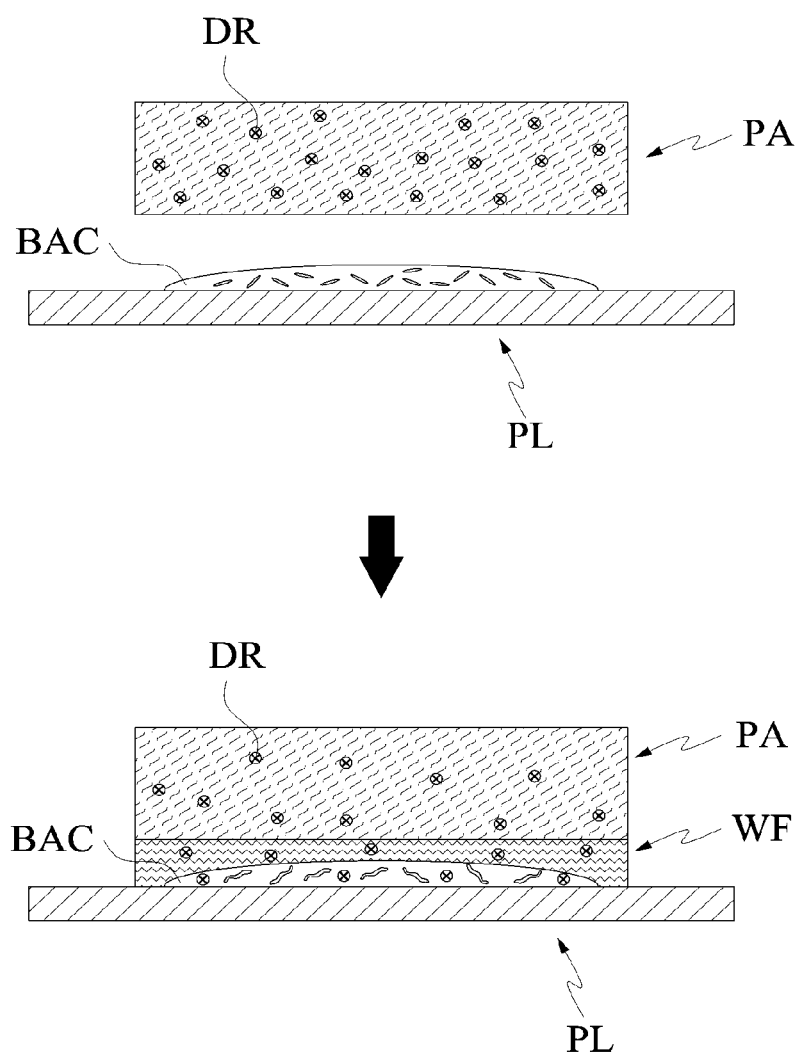
FIG. 56 is an operational view of the yet another embodiment of the drug test method of the present application.

FIG. 56 is an operational view of the yet another embodiment of the drug test method of the present application.

Referring to FIG. 56, the drug may be provided to the object to be drug-tested by contacting a patch PA with the reaction region on the plate PL (S700). In this case, the patch PA contains a drug to be tested. Such a drug patch PA may be a patch which additionally containing a drug to the culturing patch PA used in the culturing method of the present application. Alternatively, the drug patch PA may be a patch PA which is a different from the culturing patch PA used in the culturing method of the present application and contains a drug.

In addition to the drug, the drug patch PA may also contain a component required for growth required for basic growth of the object to be drug-tested.

When the drug is provided to the object to be cultured in this way, due to an influence of the drug, the growth of the object to be cultured may be inhibited, the object to be cultured may be killed, the object to be cultured may actively perform a specific reaction, or the growth of the object to be cultured may be accelerated.

Then, an image related to the object to be cultured placed on the plate PL may be acquired (S400), and an effect of the drug on the object to be cultured may be tested by analyzing the image (S800). In this case, in the present embodiment, Step S400 may be performed identically or similarly to Step S400' of the previous embodiment of the drug test method of the present application or Step S400" of the other previous embodiment. Also, Step S800 of the present embodiment may be performed identically or similarly to the above-described Step S800.

Figure 57:
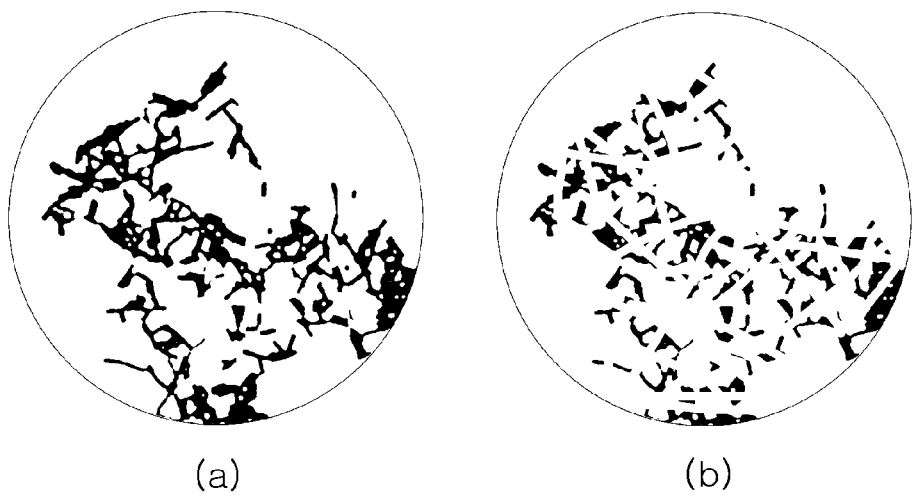
FIG. 57 is an example of an image of an object to be cultured according to the present application.

FIG. 57 is an example of an image of object to be cultured according to the present application.

Referring to FIG. 57, it can be observed that bacteria gradually die due to injection of the drug.

In the previously-described drug test method, a drug is provided to the object to be cultured placed on a single plate PL by using a single patch PA, and then an effect of the drug is detected.

However, instead, in the present application, different types of drugs or drugs having different concentrations may be simultaneously tested. For example, a reaction region on the plate PL may be divided, a first patch PA may be brought into contact with a region, a second patch PA may be brought into contact with another region, and then images of the region and the other region may be acquired to analyze reactions in the regions and compare effects of a drug contained in the first patch PA and a drug contained in the second patch PA. Alternatively, a drug test may also be performed by simultaneously using a plurality of different patches PA on a plurality of plates PL.

Instead, in the present application, drug tests on different objects to be cultured may also be simultaneously performed. For example, a first object to be cultured may be placed on a first plate PL, a second object to be cultured may be placed on a second plate, drugs may be provided to the first plate PL and the second plate PL using different patches PA, and then results thereof may be observed. In this case, when the patches PA are formed of the same components, reaction results of different objects to be cultured in response to the same drug may be compared.

7. Test Device

A test device for performing the culturing method, the culture test method, and the drug test method according to the present application will be described below.

Figure 58:
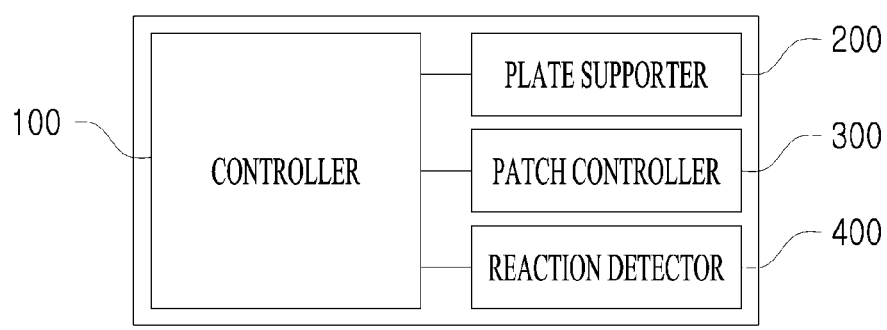
FIG. 58 illustrates an embodiment of a test device according to the present application.

FIG. 58 illustrates an embodiment of a test device according to the present application.

The test device according to the embodiment of the present application may include a plate supporter 200, a patch controller 300, and an imaging device 400. The test device according to the present embodiment may contact a patch, which includes a mesh structural body NS forming micro-cavities and contains a liquid substance SB in the micro-cavities, with the plate PL or separate the patch therefrom and acquire an image.

The plate supporter 200 may support a plate PL on which a sample SA to be diagnosed is placed in a reaction region.

The patch controller 300 may control a position of the patch PA relative to the reaction region so that a component required for growth is provided to the reaction region by one or more patches PA used in the culturing method or the testing method according to the embodiments of the present disclosure described above.

The imaging device 400 may acquire an image of the reaction region by imaging the reaction region.

Specifically, the imaging device 400 may include an image acquisition module. In this case, the image acquisition module may include a camera module.

Accordingly, the imaging device 400 may acquire partial images of the reaction region. Also, the imaging device 400 may combine the acquired partial images of the reaction region.

The test device may further include a controller 100.

The controller 100 may obtain numerical and morphological information of an object to be cultured by using an image analysis program, and in accordance with the extracted information, determine a degree of growth due to culture and a degree of growth inhibition, a degree of death, or the like due to injection of a drug.

Figure 59:
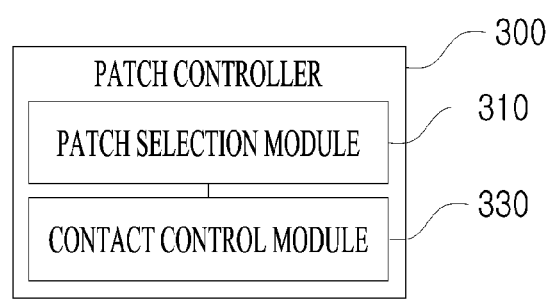
FIG. 59 illustrates an example of a patch controller in the embodiment of the test device according to the present application.

FIG. 59 illustrates an example of a patch controller in the embodiment of the test device according to the present application.

In a test device 10 according to the embodiment of the present application, the patch controller 300 may include a patch selection module 310 and a contact control module 330.

The patch selection module 310 may select a patch PA to be controlled. The selection of the patch PA to be controlled by the patch selector may include selecting a patch to be brought into contact with the reaction region among a plurality of patches PA.

The contact control module 330 may control a state of contact between a selected patch PA and the reaction region. The controlling of the contact state may include controlling a position of the patch PA relative to the reaction region.

The above description is merely illustrative of the technical spirit of the present disclosure, and those of ordinary skill in the art to which the present disclosure pertains should be able to make various modifications and changes within a scope not departing from essential characteristics of the present disclosure. Therefore, the above-described embodiments of the present disclosure may also be implemented separately or in combination.

The embodiments disclosed herein are for describing the technical spirit of the present disclosure instead of limiting the same, and the scope of the technical spirit of the present disclosure is not limited by such embodiments. The scope of the present disclosure should be interpreted on the basis of the claims below, and all technical spirits within the equivalent scope should be interpreted as belonging to the scope of the present disclosure.

The invention claimed is:

1. A drug patch comprising:
   a drug that affects growth or activity of an object to be drug-tested; and
   a mesh structural body provided in a mesh structure forming micro-cavities in which the drug is contained that is configured to come into contact with a reaction region comprising the object to be drug-tested and to provide the contained drug from the micro-cavities to the reaction region, wherein the mesh structural body is a continuously distributed solid structure having a plurality of micro-threads that are intertwined together.

2. The drug patch of claim 1, further comprising a component required for growth of the object to be drug-tested,
   wherein the component required for growth is contained in the mesh structure forming the micro-cavities.

3. The drug patch of claim 1, wherein the mesh structural body further comprises a nutrient component for growth of the object.

4. The drug patch of claim 3, wherein the nutrient component comprises at least one of bacteria or cells.

5. The drug patch of claim 1, wherein the object comprises at least one of bacteria, parasites, cells separated from a tissue, or primary cultured cells.

6. The drug patch of claim 1, wherein a liquid substance is contained within the micro-cavities.

7. The drug patch of claim 1, wherein the reaction region comprises at least one of another patch, a dried region, or a liquid region.

8. A drug patch comprising:
   a drug that affects growth or activity of an object to be drug-tested;
   a mesh structural body comprising micro-cavities containing antibodies, wherein the mesh structural body is configured to come into contact with a reaction region comprising the drug and to provide the drug to the reaction region, wherein the mesh structural body is a continuously distributed solid structure having a plurality of micro-threads that are intertwined together; and a water film between the mesh structural body and the reaction region, wherein the drug is provided to the reaction region through the water film.

9. The drug patch of claim 8, further comprising a component required for growth of the object to be drug-tested,
wherein the component required for growth is contained in the mesh structure forming the micro-cavities.

10. The drug patch of claim 8, wherein the mesh structural body further comprises a nutrient component for growth of the object.

11. The drug patch of claim 10, wherein the nutrient component comprises at least one of bacteria or cells.

12. The drug patch of claim 8, wherein the object comprises at least one of bacteria, parasites, cells separated from a tissue, or primary cultured cells.

13. The drug patch of claim 8, wherein a liquid substance is contained within the micro-cavities.

14. The drug patch of claim 8, wherein the reaction region comprises at least one of another patch, a dried region, or a liquid region.

15. A drug patch comprising:
a drug that affects growth or activity of an object to be drug-tested;
a buffer solution for facilitating an environmental condition for growth of the object; and
a mesh structural body comprising micro-cavities containing antibodies and an interruption solution, wherein the mesh structural body is configured to come into contact with an external reaction region and to provide the drug to the external reaction region, wherein the mesh structural body is a continuously distributed solid structure having a plurality of micro-threads that are intertwined together.

16. The drug patch of claim 15, wherein the buffer solution adjusts at least one of an acidity or an osmotic pressure.

17. The drug patch of claim 15, wherein the mesh structural body further comprises a nutrient component for growth of the object, the nutrient component comprising at least one of bacteria or cells.

18. The drug patch of claim 15, wherein the object comprises at least one of bacteria, parasites, cells separated from a tissue, or primary cultured cells.

19. The drug patch of claim 15, wherein a liquid substance is contained within the micro-cavities.

20. The drug patch of claim 1, wherein an external substance comprising the drug is absorbed from external region prior to being provided to the reaction region.

21. The drug patch of claim 1, wherein the drug is absorbed from an external substance prior to being provided to the reaction region, wherein the external substance comprises at least one of a liquid comprising the drug or a powder comprising the drug.

* * * * *